US008703977B2

(12) United States Patent
Boone et al.

(10) Patent No.: US 8,703,977 B2
(45) Date of Patent: Apr. 22, 2014

(54) COMPOUNDS, INTERMEDIATES, AND METHODS OF PREPARING THE SAME

(75) Inventors: Matthew A. Boone, Decatur, GA (US); Frank E. McDonald, Atlanta, GA (US)

(73) Assignee: Emory University, Atlanta, GA (US)

( * ) Notice: Subject to any disclaimer, the term of this patent is extended or adjusted under 35 U.S.C. 154(b) by 162 days.

(21) Appl. No.: 13/141,336

(22) PCT Filed: Dec. 30, 2009

(86) PCT No.: PCT/US2009/069777
§ 371 (c)(1),
(2), (4) Date: Jul. 22, 2011

(87) PCT Pub. No.: WO2010/078396
PCT Pub. Date: Jul. 8, 2010

(65) Prior Publication Data
US 2011/0275839 A1    Nov. 10, 2011

Related U.S. Application Data

(60) Provisional application No. 61/142,261, filed on Jan. 2, 2009.

(51) Int. Cl.
C07D 313/04 (2006.01)
C07D 493/04 (2006.01)
C07D 407/12 (2006.01)
C07D 317/20 (2006.01)

(52) U.S. Cl.
USPC .......................................... 549/346; 549/453

(58) Field of Classification Search
None
See application file for complete search history.

(56) References Cited

PUBLICATIONS

Fritz et al., 1934, caplus an 1934:917.*
Boone et al., Organic Letters, 2009, vol. 11, 851-854.*
Alcazar, et al. Synthesis of Seven-Membered Ring Glycals via endo-Selective Alkynol Cycloisomerization, Org. Lett., vol. 6, No. 21, 2004.
Boone et al., 1,5-r-D-Mannoseptanosides, Ring-Size Isomers That Are Impervious to r-Mannosidase-Catalyzed Hydrolysis, Org. Lett., vol. 11, No. 4, 2009.
BuUrgess, Enantioselective Esterifications of Unsaturated Alcohols Mediated by a Lipase Prepared from *Pseudomonas* sp., J. Am. Chem. Soc. 1991, 113, 6129-6139.
Fyvie et al., Synthesis of 2-iodo-2-deoxy septanosides from a D-xylose-based oxepine, Carbohydrate Research 339 (2004) 2363-2370.
Koo, Fischer Carbene Catalysis of Alkynol Cycloisomerization: Application to the Synthesis of the Altromycin B Disaccharide, Org. Lett., vol. 9, No. 9, 2007.
Markad, Stereoselectivity in the Epoxidation of Carbohydrate-Based Oxepines, J. Org. Chem. 2008, 73, 6341-6354.
McDonald et al., Stereoselective Glycosylations of a Family of 6-Deoxy-1,2-glycals Generated by Catalytic Alkynol Cycloisomerization, J. Am. Chem. Soc. 2000, 122, 4304-4309.

* cited by examiner

*Primary Examiner* — Sun Jae Yoo
(74) *Attorney, Agent, or Firm* — Emory Patent Group; James C. Mason; Susuanne Hollinger

(57) ABSTRACT

The present disclosure provides optionally substituted seven-membered ring isomers of naturally occurring carbohydrate compounds, methods of synthesizing these compounds, intermediate compounds, methods of synthesizing the intermediate compounds, and the like.

9 Claims, 1 Drawing Sheet

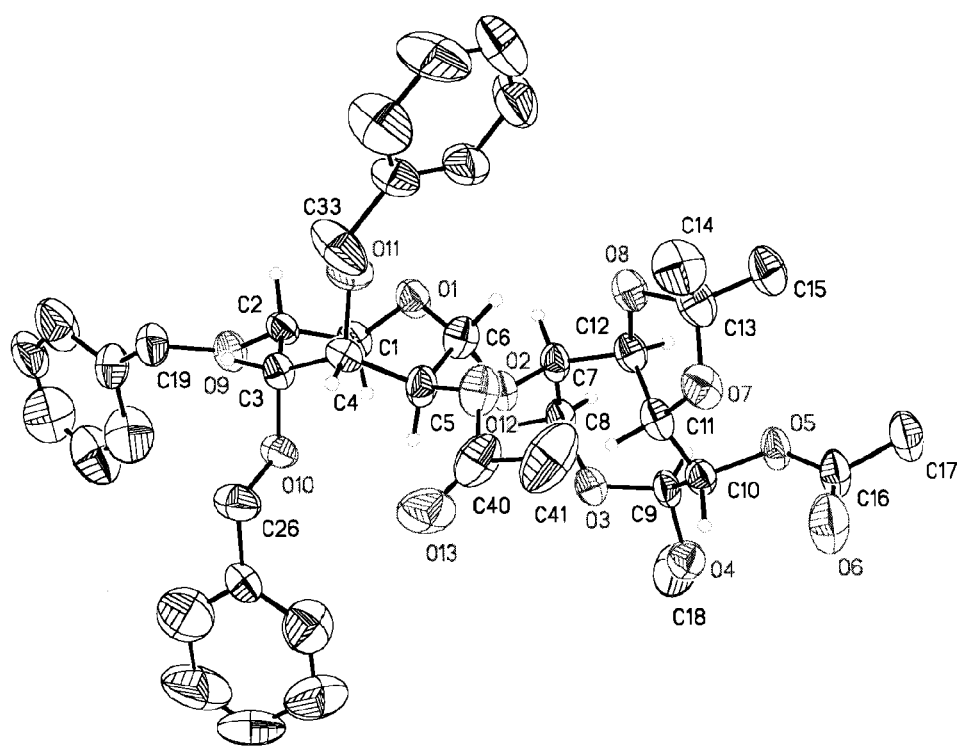

COMPOUNDS, INTERMEDIATES, AND METHODS OF PREPARING THE SAME

CROSS-REFERENCE TO RELATED APPLICATION

This application claims priority to U.S. provisional application entitled, "COMPOUNDS, INTERMEDIATES, AND METHODS OF PREPARING THE SAME," having Ser. No. 61/142,261, filed Jan. 2, 2009, which is entirely incorporated herein by reference.

BACKGROUND

Seven-membered ring (septanose) oligosaccharides are unknown in nature, since natural sugars have a thermodynamic preference of five- and six-membered rings, such as furanose and pyranose. Grindley et al. *J. Chem. Soc., Chem. Commun.* (1978) 1073. Though not naturally occurring, seven-membered ring sugar synthesis has been demonstrated via synthetic methods utilizing extensive protective group manipulations of secondary alcohols of hexose sugars or by rearrangements of appropriately protected furanoside derivatives. Stevens et al. *J. Chem. Soc., Chem. Commun.* (1969) 1140; Ng et al. *Carbohydr. Res.* (1996) 284:241; Tran et al. *Aust. J. Chem.* (2002) 55:171; Anet, E. F. L. J. *Carbohydr. Res.* (1968) 8:164; Micheel et al. *Justus Liebigs Ann. Chem.* (1933) 502:85; Ward et al. *Can. J. Chem.* (1994) 72:1429; McAuliffe et al. *Synlett.* (1998) 307; Contour et al. *Carbohydr. Res.* (1990) 201:150.

Additionally, the synthesis of septanose glycals has been described via tungsten-catalyzed cycloisomerization of terminal alkynyl alcohols. Alcázar et al. *Org. Lett.* (2004) 6:3877; Koo et al. *Org. Lett.* (2007) 9:1737. Recently, Peczuh et al. provided considerable insight into the preparation and functionalization of septanose carbohydrates. Peczuh et al. *Carbohydr. Res.* (2004) 339:1163; Fyvie et al. *Carbohydr. Res.* (2004) 339:2363; DeMatteo et al. *J. Org. Chem.* (2005) 70:24; Castro et al. *J. Org. Chem.* (2005) 70:3312; Castro et al. *Org. Lett.* (2005) 7:4709.

SUMMARY

Embodiments of the present disclosure provide for optionally substituted seven-membered ring isomers of naturally occurring carbohydrate compounds, methods of synthesizing these compounds, intermediate compounds, methods of synthesizing the intermediate compounds, and the like.

An embodiment includes a compound of formula I as described herein.

An embodiment includes a compound of formula II as described herein.

An embodiment includes a compound of formula VII as described herein.

An embodiment of a process for preparing a compound having formula I, including: (a) cycloisomerization of an alkynyl alcohol in the presence of a catalyst to provide a glycal alcohol; (b) cleavage and O-benzylation of the glycal alcohol of step (a) to provide a septanose glycal; (c) epoxidation of the septanose glycal of step (b) to provide a septanose epoxide intermediate; (d) nucleophilic ring opening of the septanose epoxide intermediate of step (c) to provide a protected septanoside; (e) deprotection of the protected septanoside of step (d) to provide a septanoside acceptor or donor synthon which may be further deprotected or glycosylated and deprotected to provide a compound of formula (I).

An embodiment of a process for preparing a compound having formula VII, including: (a) protecting an enediol with a protecting group and converting the enediol into an enynol; (b) catalyzed resolution of the enynol of step (a) to provide an acetate; (c) converting of the acetate of step (b) to provide an enynol; (d) epoxidation of the enynol of step (c) followed by conversion of the epoxidation reaction into an alkynyl diol; (e) protecting the alkynyl diol of step (d) to provide a compound of formula (VII).

An embodiment of a process for preparing a compound having formula II, including: (a) cycloisomerization of an alcohol in the presence of a catalyst to provide a glycal alcohol; (b) cleavage and O-benzylation of the glycal alcohol of step (a) to provide a septanose glycal; (c) epoxidation of the septanose glycal of step (b) to provide a septanose epoxide intermediate; (d) nucleophilic ring opening of the septanose epoxide intermediate of step (c) to provide a protected septanoside; (e) deprotection of the protected septanoside of step (d) to provide a septanoside acceptor or donor synthon which is glycosylated and deprotected to provide a compound of formula (II).

These embodiments, uses of these embodiments, and other uses, features and advantages of the present disclosure, will become more apparent to those of ordinary skill in the relevant art when the following detailed description of the preferred embodiments is read in conjunction with the appended figures.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of this disclosure.

FIG. 1 illustrates a thermal ellipsoid of compound 26.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Ratios, concentrations, amounts, and other numerical data may be expressed herein in a range format. Such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. For illustration purposes only, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

I. Definitions

Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, "acyl" means a hydrogen atom or a saturated or unsaturated $C_{1-6}$ chain hydrocarbon group bound to a carbonyl group. Examples of acyl groups include, but are not limited to, benzoyl, formyl, acetyl, propionyl, butyryl, isobutyryl, valeryl, isovaleryl, pivaloyl, hexanoyl, acryloyl, methacryloyl, crotonoyl groups, and the like.

As used herein unless otherwise specified, "alkyl" means an aliphatic hydrocarbon group that is a straight or branched chain, preferably having about 1 to 12 carbon atoms in the chain. Advantageous alkyl groups may include lower alkyl groups, which may contain from about 1 to 6 carbon atoms. "Branched" refers to one or more lower alkyl groups such as methyl, ethyl or propyl which are themselves attached to a linear alkyl chain. Unless otherwise specified, the alkyl group may be unsubstituted or independently substituted by one or more groups, such as, but not limited to halo, carboxy, formyl, sulfo, sulfino, carbamoyl, amino and imino. Whenever a range of carbon atoms is referred to, it independently and separately includes every member of the range. As a non-limiting example, the term "$C_{1-4}$alkyl" includes methyl, ethyl, propyl, isopropyl, i-butyl, n-butyl, s-butyl, t-butyl, and the like.

As used herein, "alkenyl" means an aliphatic hydrocarbon group containing a carbon-carbon double bond and which may be straight or branched chained having from about 2 to about 10 carbon atoms in the chain. "Branched" means that one or more lower alkyl or lower alkenyl groups are attached to a linear alkenyl chain. Unless otherwise specified, the alkenyl group may be unsubstituted or independently substituted by one or more groups, including but not limited to, carboxy, formyl, sulfo, sulfino, carbamoyl, amino, imino, and the like. Whenever a range of carbon atoms is referred to, it independently and separately includes every member of the range. For example, the term "$C_{2-4}$alkenyl" includes, but is not limited to, ethene, propene, butene, and the like.

As used herein, "alkynyl" means an aliphatic hydrocarbon group containing a carbon-carbon triple bond and which may be straight or branched having about 2 to 10 carbon atoms in the chain. "Branched" means that one or more lower alkyl, alkenyl or alkynyl groups are attached to a linear alkynyl chain. Whenever a range of carbon atoms is referred to, it independently and separately includes every member of the range. As a non-limiting example, the term "$C_{2-4}$alkyl" includes ethyne, propyne, butyne, and the like.

As used herein, "alkoxy" means an O-alkyl group in which the alkyl group is as previously described.

As used herein, "alkylcarbonyl" refers to a carbonyl group attached to an alkyl group.

As used herein, "cycloalkyl" refers to saturated cyclic carbon rings.

As used herein, "carbonyl" means a group of the structure —C(=O).

As used herein, "halo" means F, Cl, Br, and I.

In an embodiment, "cycloisomerization" refers to a chemical process by which a molecule is transformed into another molecule which has the same number of atoms but rearranged to form a ring.

In an embodiment, "cleavage" refers to a chemical process by which a molecular bond is broken or a process by which a complex molecule is split into simpler molecules.

In an embodiment, "benzylation" refers to a chemical process by which a benzyl moiety is added to a molecule.

In an embodiment, "epoxidation" refers to a chemical process by which an epoxy compound is produced.

In an embodiment, "nucleophilic ring opening" refers to a chemical process by which a cyclic molecule is opened or made into a branched or linear chain compound.

In an embodiment, "deprotection" refers to a chemical process by which a protecting group is removed.

II. Abbreviations

Camphorsulfonic acid (CSA); 1,4-diazabicyclo[2.2.2]octane (DABCO); diisopropyl azodicarboxylate (DIAD); diisobutylaluminium hydride (DIBAL); diisopropyl tartrate (DIPT); dimethyldioxirane (DMDO); dimethylformamide (DMF); 1,3-dimethyl-3,4,5,6-tetrahydro-2(1H)-pyrimidinone (DMPU); dimethyl sulfoxide (DMSO); high resolution mass spectrometry (HRMS); N-Iodosuccinimide (NIS); 2-(trimethylsilyl)ethoxymethyl chloride (SEMCl); tetra-n-butylammonium iodide (TBAI); tetra-n-butylammonium fluoride (TBAF); tert-butyldimethylsilyl (TBS); trifluoroacetic acid (TFA); triisopropylchlorosilane (TIPSCl); trimethylsilyl (TMS); thin layer chromatography (TLC); toluenesulfonic acid (p-TSA); and tetrahydrofuran (THF).

III. Embodiments of the Present Disclosure

The present disclosure provides optionally substituted seven-membered ring isomers of naturally occurring carbohydrate compounds, methods of synthesizing these compounds, intermediate compounds, methods of synthesizing the intermediate compounds, and the like.

In addition, embodiments of the present disclosure include optionally substituted seven-membered ring compounds, such as septanose saccharide compounds, for instance septanose monosaccharide, disaccharide, trisaccharide, oligosaccharide, and polysaccharide compounds, methods of synthesizing these compounds, and the like.

An aspect of the present disclosure provides an optionally substituted septanose saccharide compound, e.g., a monosaccharide, disaccharide, trisaccharide, oligosaccharide, or polysaccharide, as well as methods of preparing these compounds.

An embodiment of the present disclosure includes an optionally substituted septanose monosaccharide compound and methods of preparing these compounds.

An embodiment of the present disclosure includes an optionally substituted septanose disaccharide compound and methods of preparing these compounds.

An embodiment of the present disclosure includes an optionally substituted septanose trisaccharide compound and methods of preparing these compounds.

An embodiment of the present disclosure includes an optionally substituted septanose oligosaccharide compound and methods of preparing these compounds.

An embodiment of the present disclosure includes an optionally substituted septanose polysaccharide compound and methods of preparing these compounds.

In each of the embodiments noted above, the method of preparation may include using an acetonide or benzylidene acetal intermediate compound. Accordingly, an embodiment of the present disclosure includes methods of synthesizing these intermediate compounds.

An aspect of the present disclosure provides compounds according to formula (I):

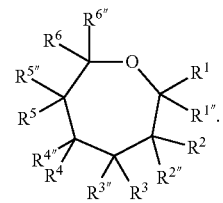

$R^1$ and $R^{1'''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, $CH_2N_3$, and

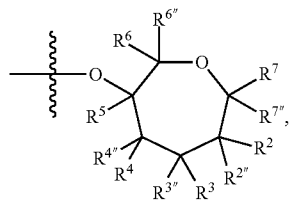

with the proviso that one of $R^1$ and $R^{1'''}$, but not both, is alkoxy or

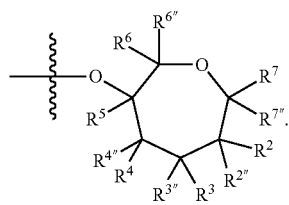

R is selected from the group consisting of: H; $C_{1-6}$alkyl, $C_{2-6}$alkenyl, or $C_{2-6}$alkynyl, each of which is optionally substituted; CN, $N_3$, halo, OH, $CONH_2$, $NH_2$, and amidino.

$R^2$-$R^5$ and $R^{2'''}$-$R^{5'''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$.

It should be noted that reference to a grouping of "$R^2$-$R^5$ and $R^{2'''}$-$R^{5'''}$" (or a similar type of grouping that may have different R# groups) includes $R^2$, $R^3$, $R^4$, $R^5$, $R^{2''}$, $R^{3''}$, $R^{4''}$, or $R^{5''}$, and each of these are each independently selected from the group described thereafter.

$R^6$ and $R^{6''}$ are independently selected from the group consisting of: H and alkyl.

$R^7$ and $R^{7''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, $CH_2N_3$, and

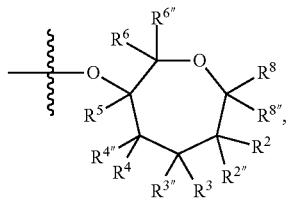

with the proviso that one of $R^7$ and $R^{7''}$, but not both, is alkoxy or

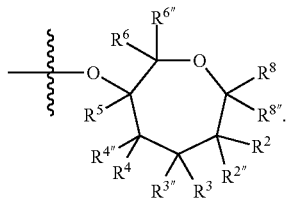

$R^8$ and $R^{8''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$-alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$.

An embodiment of the present disclosure includes a compound according to formula (I), wherein R, $R^2$-$R^5$, $R^{2''}$-$R^{5''}$, $R^7$, $R^{7''}$, $R^8$, and $R^{8''}$ are as defined above, and $R^1$ or $R^{1''}$, but not both, is alkoxy; and $R^6$ and $R^{6''}$ are H.

An embodiment of the present disclosure includes a compound according to formula (I), wherein R, $R^2$-$R^5$, $R^{2''}$-$R^{5''}$, $R^7$, $R^{7''}$, $R^8$, and $R^{8''}$ are as defined above, and $R^1$ or $R^{1''}$, but not both, is alkoxy; and $R^6$ and $R^{6''}$ are H.

An embodiment of the present disclosure includes a compound according to formula (I), wherein R, $R^7$, $R^{7''}$, $R^8$, and $R^{8''}$ are defined above; $R^1$ or $R^{1''}$, but not both, is alkoxy; $R^6$ and $R^{6''}$ are H; $R^2$-$R^5$ and $R^{2''}$-$R^{5''}$ are each independently H, OH, $C_{1-6}$alkyl, or alkoxy.

An embodiment of the present disclosure includes a compound according to formula (I), wherein R, $R^7$, $R^{7''}$, $R^8$, and $R^{8''}$ are defined above; $R^{1''}$ is H; $R^6$ and $R^{6''}$ are H; $R^2$-$R^5$ are OH; $R^{2''}$-$R^{5''}$ are H.

An embodiment of the present disclosure includes a compound according to formula (I), wherein R, $R^7$, $R^{7''}$, $R^8$, and $R^{8''}$ are defined above; $R^1$ is methoxy; $R^{1''}$ is H; $R^6$ and $R^{6''}$ are H; $R^2$-$R^5$ are OH; $R^{2''}$-$R^{5''}$ are H.

An embodiment of the present disclosure includes a compound according to formula (I), wherein $R^1$ and $R^{1''}$ are independently H or

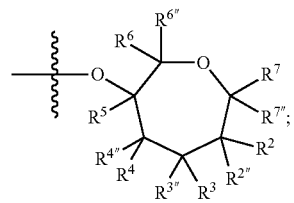

$R^2$-$R^4$ are OH; $R^5$ is H; $R^6$ is H; $R^{2''}$-$R^{4''}$, $R^{6''}$, and $R^{7''}$ are H; $R^{5''}$ is OH; and $R^7$ is alkoxy.

An embodiment of the present disclosure includes a compound according to formula (I), wherein $R^1$ is

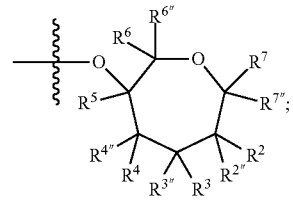

$R^{1''}$ is H; $R^2$-$R^4$ are OH; $R^5$ is H; $R^6$ is H; $R^{2''}$-$R^{4'}$, $R^{6''}$, and $R^{7''}$ are H; $R^{5''}$ is OH; and $R^7$ is methoxy.

An embodiment of the present disclosure includes a compound according to formula (I), wherein $R^1$ is

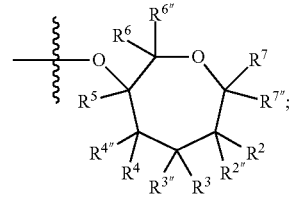

$R^{1''}$ is H; $R^2$-$R^4$ are OH; $R^5$ is H; $R^6$ is H; $R^{2''}$-$R^{4'}$, $R^{6''}$, and $R^{7''}$ are H; $R^{5''}$ is OH; $R^7$ is

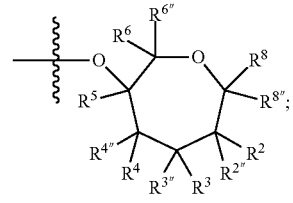

$R^8$ is alkoxy; and $R^{8''}$ is H.

An embodiment of the present disclosure includes a compound according to formula (I), wherein $R^1$ is

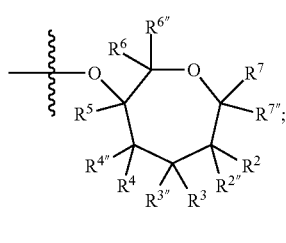

$R^{1''}$ is H; $R^2$-$R^4$ are OH; $R^5$ is H; $R^6$ is H; $R^{2''}$-$R^{4''}$, $R^{6''}$, and $R^{7''}$ are H; $R^{5''}$ is OH; $R^7$ is

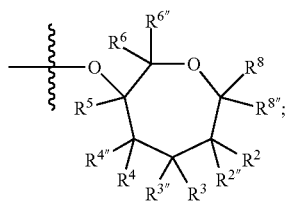

$R^8$ is methoxy; and $R^{8''}$ is H.

An embodiment of the present disclosure includes a compound of formula (II):

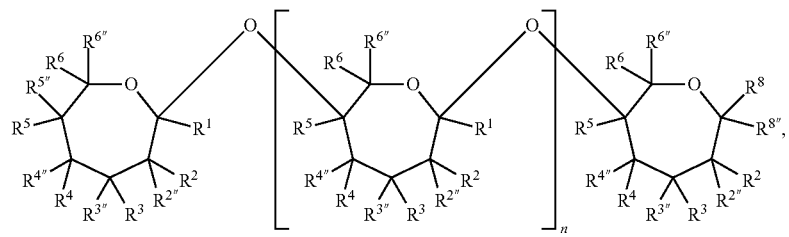

wherein:

$R^1$ is independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$.

$R^8$ and $R^{8''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$.

$R^2$-$R^5$ and $R^{2''}$-$R^{5''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$.

$R^6$ and $R^{6''}$ are independently selected from the group consisting of H and alkyl; and n is 0 to 10,000 or 1 to 10,000 and any integer combination between these numbers.

An embodiment of the present disclosure includes a compound according to formula (II), wherein n can be selected from the group of ranges consisting of: 0 to 10,000; 0 to 1000; 0 to 100; 0 to 10; 0 to 1; 1 to 10; 10 to 100; 100 to 200; 200 to 2,000; 50 to 1000, 1 to 10,000, 1 to 1000, and 1 to 100.

An embodiment of the present disclosure includes a compound according to formula (II), wherein: $R^2$-$R^4$ are OH; $R^5$ is H; $R^6$ is H; $R^8$ is alkoxy; $R^{2''}$-$R^{4''}$, $R^{6''}$, and $R^{7''}$ are H; $R^{5''}$ is OH; $R^8$ is alkoxy; and $R^{8''}$ is H; and n can be selected from the group of ranges consisting of: 0 to 10,000; 0 to 1000; 0 to 100; 0 to 10; 0 to 1; 1 to 10; 10 to 100; 100 to 200; 200 to 2,000; 50 to 1000, 1 to 10,000, 1 to 1000, and 1 to 100.

An embodiment of the present disclosure includes a compound according to formula (III):

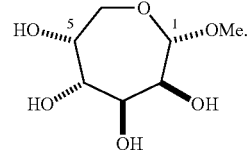

An embodiment of the present disclosure includes a compound according to formula (IV):

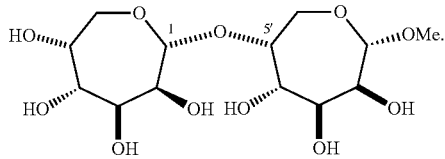 [SMILES: CO[C@H]1OC[C@@H](O[C@H]2OC[C@@H](O)[C@@H](O)[C@H](O)[C@@H]2O)[C@@H](O)[C@H](O)[C@@H]1O]

An embodiment of the present disclosure includes a compound according to formula (V):

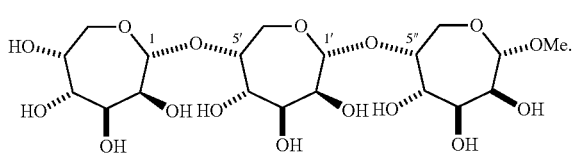 [SMILES: CO[C@H]1OC[C@@H](O[C@H]2OC[C@@H](O[C@H]3OC[C@@H](O)[C@@H](O)[C@H](O)[C@@H]3O)[C@@H](O)[C@H](O)[C@@H]2O)[C@@H](O)[C@H](O)[C@@H]1O]

An embodiment of the present disclosure includes a compound according to formula (VI):

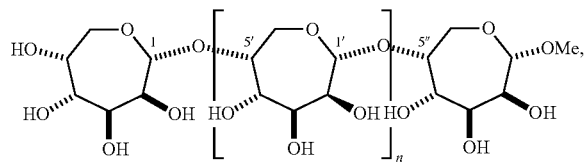

where n can be selected from the group of ranges consisting of: 0 to 10,000; 0 to 1000; 0 to 100; 0 to 10; 0 to 1; 1 to 10; 10 to 100; 100 to 200; 200 to 2,000; 50 to 1000, 1 to 10,000, 1 to 1000, and 1 to 100.

An aspect of the present disclosure provides an acetonide or benzylidene acetal intermediate compound. For example, an embodiment of the present disclosure provides a compound of the formula (VII):

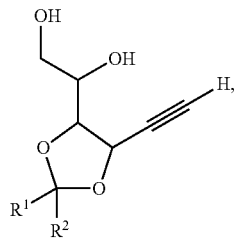

wherein $R^1$ and $R^2$ are selected from the group consisting of: H, alkyl, and phenyl, such as

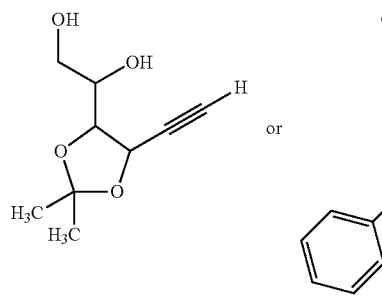

IV. Synthesis of the Embodiments of the Present Disclosure

An aspect of the present disclosure provides a method for preparing septanose saccharides. In an embodiment, the method includes using an acetonide or benzylidene acetal intermediate compound.

An aspect of the present disclosure provides methods for preparing compounds of formulae (I)-(IX). The following schemes depict exemplary chemistry available for synthesizing the disclosed compounds.

An aspect of the present disclosure provides a method of synthesis of compounds according to formula (I), comprising:

(a) cycloisomerization of an alcohol (e.g., an alkynyl alcohol) in the presence of a catalyst to provide a glycal alcohol;

(b) cleavage and O-benzylation of the glycal alcohol of step (a) to provide a septanose glycal;

(c) epoxidation of the septanose glycal of step (b) to provide a septanose epoxide intermediate;

(d) nucleophilic ring opening of the septanose epoxide intermediate of step (c) to provide a protected septanoside; and (e) deprotection of the protected septanoside of step (d) to provide a septanoside acceptor or donor synthon which may be further deprotected or glycosylated and deprotected to provide a compound of formula (I) or (II).

In an embodiment, the alcohol of step (a) can be an alkynyl alcohol, for instance a terminal alkynyl alcohol, which may be an alkynyl diol, such as

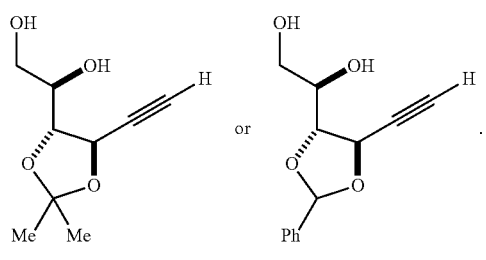

The cycloisomerization can occur in the presence of a catalyst such as a transition metal catalyst, for example tungsten, to provide a glycal alcohol, such as

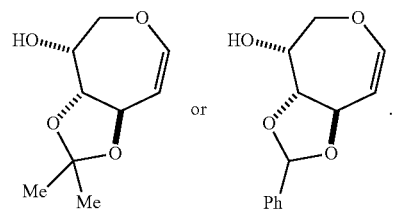

In an embodiment, the glycal alcohol produced in step (a) is cleaved, for example by reductive cleavage, and protected, for example by O-benzylation to provide a septanose glycal, such as

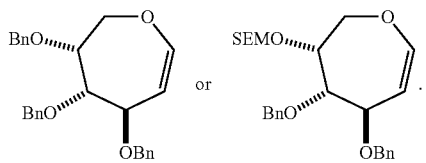

In an embodiment, the septanose glycal produced in step (b) undergoes epoxidation, for example DMDO epoxidation, to provide a septanose epoxide intermediate, such as

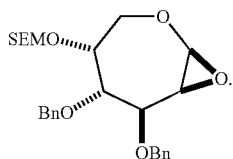

In an embodiment, the septanose epoxide intermediate produced in step (c) undergoes nucleophilic ring opening, for example with sodium methoxide or lithium thiophenoxide to provide a protected septanoside, for example a D-mannoseptanoside, such as

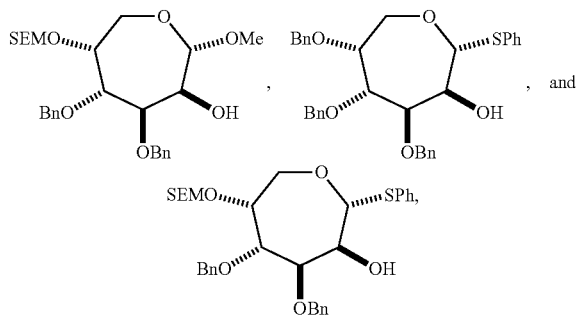

In an embodiment, the protected septanoside of step (d) may be deprotected to provide a septanoside acceptor or donor synthon, for example a mannoseptanoside acceptor or donor synthons such as

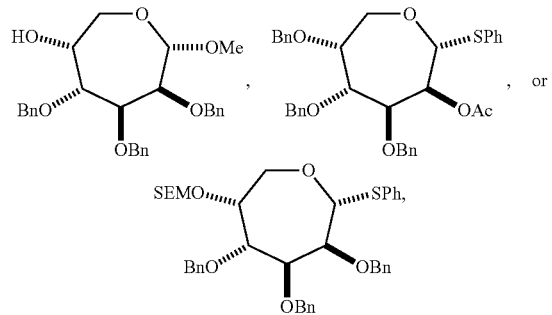

which may be further deprotected to provide a compound of formula (I) or glycosylated and deprotected to provide a compound of formula (II), such as

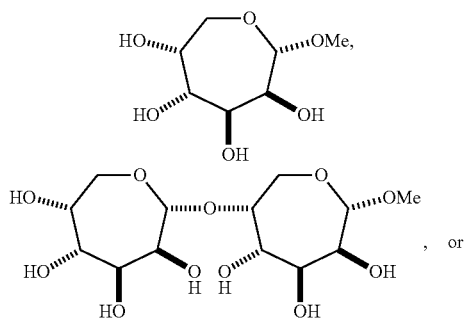

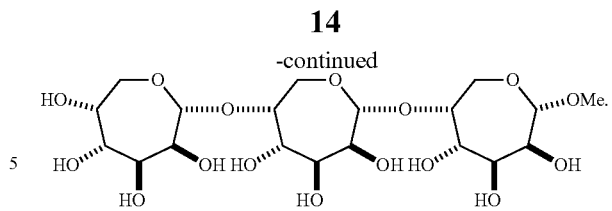

The following schemes depict exemplary chemistry available for synthesizing the disclosed compounds.

An embodiment of the present disclosure provides a method of synthesis of a compound according to formula (VII),

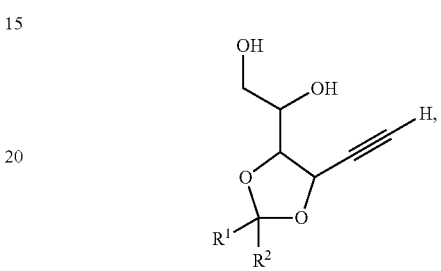

comprising:
(a) protecting an enediol with a protecting group and converting the enediol into an enynol;
(b) catalyzed resolution of the enynol of step (a) to provide an acetate ester;
(c) converting of the acetate ester of step (b) to provide an enynol;
(d) epoxidation of the enynol of step (c) followed by conversion into an alkynyl diol; and
(e) protecting the alkynyl diol of step (d) to provide a compound of formula (VII).

In an embodiment, the enediol of step (a), e.g., (1,4-cis-2-buten-ol) is protected, for example by adding a protecting group, e.g., TIPSCl, and the protected enediol is converted into an enynol, e.g.,

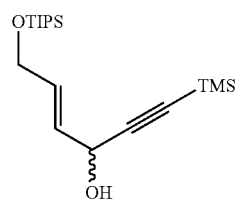

via an aldehyde intermediate, e.g.,

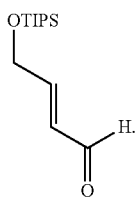

In an embodiment, the lipase catalyzed resolution of the enynol of step (a) is catalyzed, e.g., with Lipase AK and an acetate such as vinyl acetate, to provide an acetate ester, e.g.,

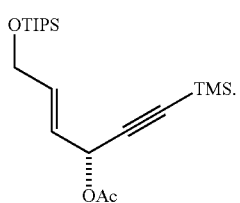

In an embodiment, the acetate ester of step (b) is converted into an enynol, e.g.,

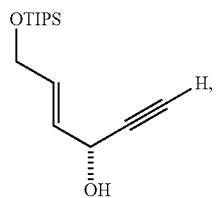

for instance by Sharpless kinetic resolution of the acetate ester.

In an embodiment, the enynol of step (c) undergoes epoxidation, e.g., Sharpless epoxidation, to produce an epoxy alcohol, e.g.,

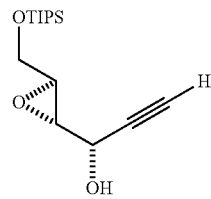

followed by conversion into an alkynyl diol, e.g.,

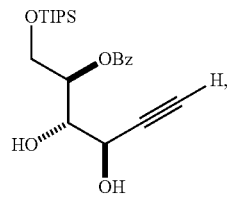

for instance by Mitsunobu inversion and Ti(O-i-Pr$_4$)-promoted regioselective addition of benzoic acid.

In an embodiment, the alkynyl diol of step (d) is converted into a cyclic acetal, e.g.,

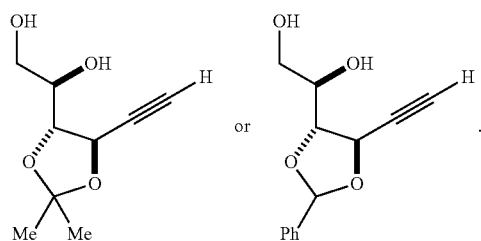

Although preferred embodiments of the present disclosure have been described using specific terms, devices, and methods, such description is for illustrative purposes only. The words used are words of description rather than words of limitation. Changes and variations may be made by those of ordinary skill in the art without departing from the spirit or the scope of the present disclosure, which is set forth in the appended claims. In addition, aspects of the various embodiments may be interchanged both in whole or in part. The present disclosure is further illustrated by the following examples, which are provided by way of illustration and are not meant to be construed as limiting. The contents of all references, published patents, and patents cited throughout the present application are also hereby incorporated by reference in their entireties.

Despite the differences in hydroxyl positions for septanosides, it is anticipated that the biocompatibility of these compounds will be quite high, as potential enzymatic or non-enzymatic glycosidic hydrolysis will yield the biologically innocuous hexose sugar. Furthermore, the absence of primary hydroxyl groups and conformational differences for the seven-membered ring isomer may result in novel enzymatic reactivity or stability, potentially harnessed in applications of septanose oligosaccharides as biomaterials or components for drug delivery.

Enzymatic or non-enzymatic glycosidic hydrolysis of septanosides is expected to yield a biologically innocuous hexose sugar, such as D-mannopyranose. Thus, biocompatibility of these substrates is anticipated to be quite high, similar to their six-membered oligosaccharide isomers.

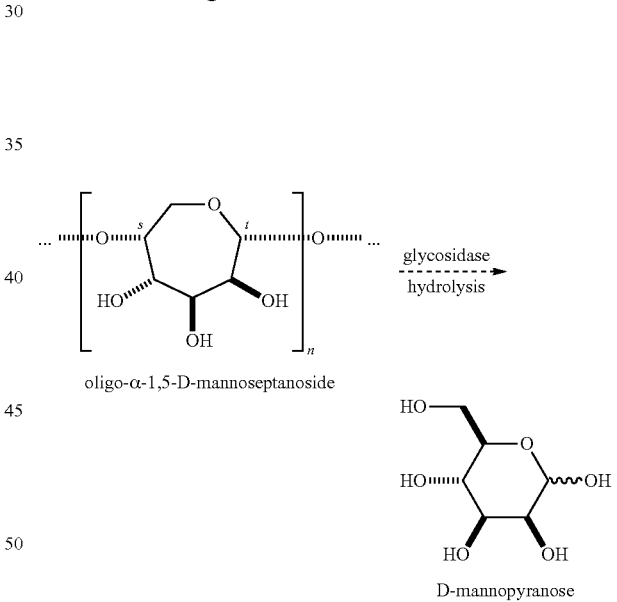

In an embodiment, sepatanose sugars can be used to replace desosamine and/or cladinose in naturally occurring sugars, which may project hydroxyl and/or amino functional groups in appropriate positions, but the septanosides may be more hydrolytically and/or enzymatically stable when compared with desosamine and/or cladinose glycosides.

EXAMPLES

Example 1

A. Synthesis of D-Arabinoseptanose Glycals 9-13

1. Preparation of Enynol (±)-2

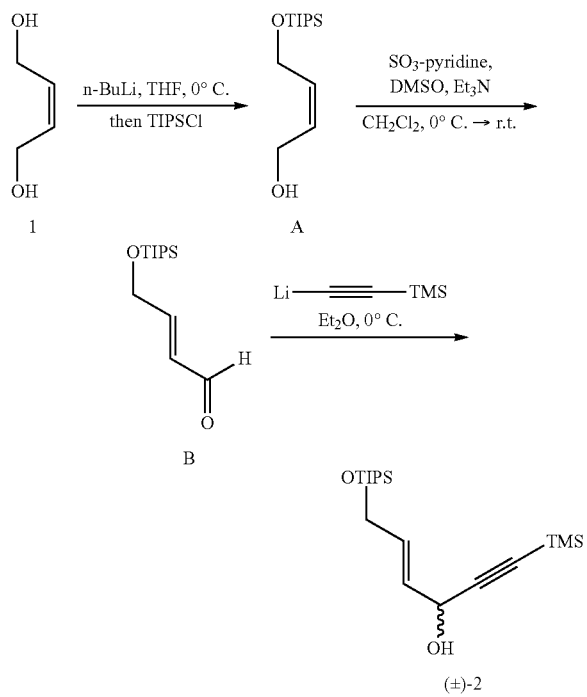

Commercially available 1,4-cis-2-buten-ol (1) (20 g, 19 mL, 230 mmol) was added to THF (0.50 M, 500 mL). The solution was cooled to 0° C., and n-BuLi (2.5 M in hexanes, 100 mL, 250 mmol) was slowly added over a 20 minute period. The reaction was stirred for 30 minutes at 0° C., at which point TIPSCl (43 mL, 225 mmol) was added dropwise over a 5 minute period. The reaction was allowed to warm to room temperature over a 2 hour period. The reaction was then quenched by the addition of a saturated solution of $NH_4Cl$ (300 mL). The aqueous layer was extracted with EtOAc (2×100 mL). The combined organics were dried with $MgSO_4$, filtered, and concentrated under reduced pressure. Chromatography (20:1→1:1 hexanes:EtOAc) afforded TIPS-protected compound A as a colorless oil (47 g, 85%).

$^1$H NMR (600 MHz, $CDCl_3$) δ 5.72 (m, 2H), 4.34 (d, J=4.2 Hz, 2H), 4.22 (d, J=4.8 Hz, 2H), 1.08 (m, 21H); $^{13}$C NMR (100 MHz, $CDCl_3$) δ 131.7, 130.1, 60.1, 59.3, 18.2, 12.1; IR (KBr) 3351, 2943, 2867, 1463, 1097, 883, 682 cm$^{-1}$; HRMS (ESI) [M+H] Calcd. for $C_{23}H_{29}O_2Si_1$, 245.19314, found 245.19300.

Compound A (11.5 g, 47 mmol) was dissolved in $CH_2Cl_2$ (0.50M, 100 mL). DMSO (6.7 mL, 94 mmol) and $Et_3N$ (13 mL, 94 mmol) were added sequentially to the stirring solution, which was then cooled to 0° C. $SO_3$-pyridine (15 g, 94 mmol) was then added to the solution all at once. The reaction was allowed to warm to r.t. and was stirred for 3 hours. The reaction was quenched by the addition of $H_2O$ (150 mL). The aqueous layer was extracted with $CH_2Cl_2$ (2×50 mL). The organics were combined and dried over $MgSO_4$. After filtration and concentration under reduced pressure, the crude mixture was purified via chromatography (20:1→9:1 hexanes:EtOAc) to give aldehyde B as a pale yellow oil (8.5 g, 75%). This procedure was optimal at the reported scale, thus the oxidation was repeated twice to provide sufficient material for the subsequent step.

$^1$H NMR (400 MHz, $CDCl_3$) δ 9.63 (d, J=8.0 Hz, 1H), 6.9 (dt, J=3.2, 15.2 Hz, 1H), 6.48 (qt, J=2.0, 8.0, 15.2 Hz, 1H), 4.56 (dd, J=2.0, 3.2 Hz), 1.08 (m, 21H); $^{13}$C NMR (100 MHz, $CDCl_3$) δ 180, 156.9, 130.7, 62.8, 18.1, 12.1; IR (KBr) 2943, 2867, 2722, 1692, 1463, 1149, 1116, 966, 883, 684 cm$^{-1}$; HRMS (ESI) [M+H] Calcd. for $C_{13}H_{27}O_2Si_1$, 243.17749, found 243.17764.

To a stirring solution of TMS acetylene (16 mL, 114 mmol) in THF (0.50 M, 190 mL) at 0° C. was slowly added n-BuLi (2.5 M in hexanes, 42 mL, 105 mmol) over a period of 30 minutes. Upon completion of the addition, the solution was allowed to stir for an additional 30 minutes at 0° C. Then aldehyde B (23 g, 95 mmol) was slowly added via syringe over a 10 minute period. The reaction was stirred for 1 hour upon addition of B. The reaction was quenched by the addition of a saturated solution of $NH_4Cl$ (100 mL), followed by extraction of the aqueous layer with EtOAc (1×100 mL). The organic extracts were combined and dried with $MgSO_4$. After filtration and concentration, (±)-2 was obtained as a yellow oil (32 g, 95%).

$^1$H NMR (400 MHz, $CDCl_3$) δ 6.01 (dtd, J=1.2, 4.0, 15.2 Hz, 1H), 5.91 (ddt, J=1.6, 6.0, 15.2 Hz, 1H), 4.91 (ddd, J=1.2, 5.2, 6.6 Hz, 1H), 4.31 (m, 2H), 1.83 (d, J=6.4 Hz, 1H) 1.09 (m, 21H), 0.19 (s, 9H); $^{13}$C NMR (100 MHz, $CDCl_3$) δ 132.6, 128.2, 104.7, 91.1, 63.1, 63.0, 18.2, 12.2, 0.024; IR (KBr) 3368, 2944, 2867, 2173, 1463, 1383, 1131, 1100, 963, 845, 761 683 cm$^{-1}$; HRMS (APCI) [M+H] Calcd. for $C_{18}H_{37}O_2Si_2$ 341.23266, found 341.23226.

2. Synthesis of Acetate 3 Via Lipase-Catalyzed Resolution

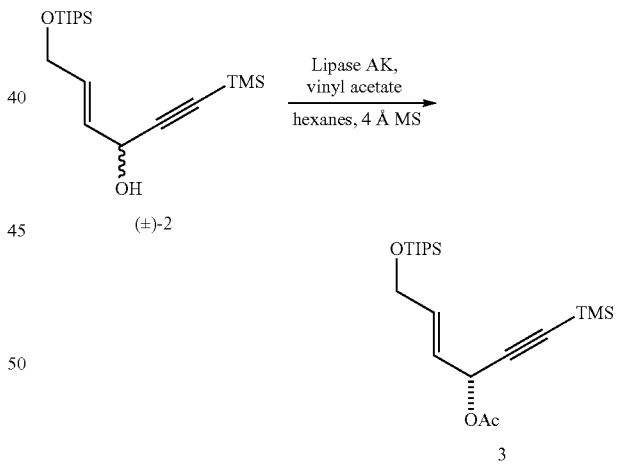

The racemic alcohol (±)-2 (42 g, 120 mmol) was dissolved in hexanes (0.50 M, 240 mL) and 4 Å MS (42 g, powdered) were added. Then Lipase AK (Amano) (21 g) was added all at once, followed by the addition of vinyl acetate (84 mL). The solution was vigorously stirred at room temperature for 72 hours, after which time the mixture was filtered through celite. The volatiles were evaporated under reduced pressure. Chromatography (25:1→20:1→10:1 hexanes:EtOAc) yielded 3 as a pale yellow oil (20 g, 48%).

$[α]_D^{23}$=−1.4° (c=1.00, $CHCl_3$); $^1$H NMR (400 MHz, $CDCl_3$) δ 6.08 (dtd, J=0.80, 4.0, 15.2 Hz, 1H), 5.94 (dd, J=0.80, 6.0, 1H), 5.83 (ddt, J=1.6, 6.0, 15.2 Hz, 1H), 4.31 (m, 2H), 2.09 (s, 3H) 1.08 (m, 21H), 0.19 (s, 9H); $^{13}$C NMR (100 MHz, CDCl$_3$) δ 169.9, 135.2, 124.2, 100.9, 92.2, 64.3, 62.9, 21.4, 18.2, 12.2, −0.044; IR (KBr) 2944, 2867, 2181, 1746, 1464, 1370, 1227, 1130, 1014, 847, 761, 683 cm$^{-1}$; HRMS (ESI) [M+H] Calcd. for C$_{20}$H$_{39}$O$_3$Si$_2$ 383.24323, found 383.24339.

3. Synthesis of Enynol (−)-4

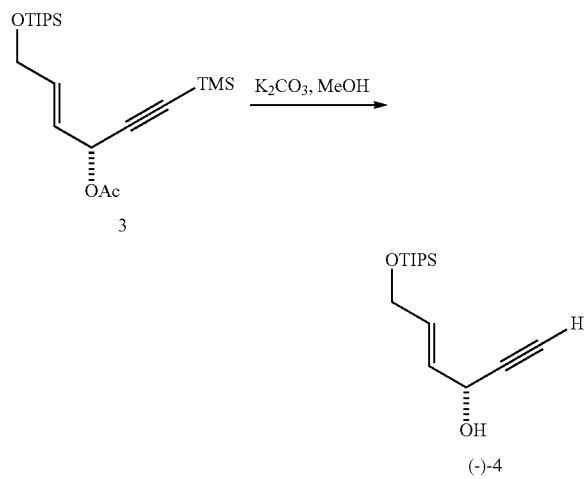

To a stirring solution of acetate ester 3 (20 g, 52 mmol) in MeOH (0.50 M, 100 mL) was added K$_2$CO$_3$ (11 g, 78 mmol) all at once. After stirring for 30 minutes at room temperature, the reaction was diluted with Et$_2$O (100 mL) and quenched with a saturated solution of NH$_4$Cl (150 mL). The aqueous layer was extracted with Et$_2$O (2×50 mL). The organics were combined, dried with MgSO$_4$, and filtered. The volatiles were evaporated under reduced pressure to provide enynol (−)-4 (14 g, Quant.).

[α]$_D^{23}$=−10.9° (c=1.00, CHCl$_3$); $^1$H NMR (400 MHz, CDCl$_3$) δ 6.05 (dtd, J=1.2, 4.0, 15.2 Hz, 1H), 5.93 (ddt, J=2.0, 5.2, 15.2 Hz, 1H), 4.93 (m, 1H), 4.31 (m, 2H), 2.58 (d, J=2.0 Hz, 1H), 1.85 (d, J=6.4 Hz, 1H), 1.09 (m, 21H); $^{13}$C NMR (100 MHz, CDCl$_3$) δ 132.9, 127.7, 83.1, 74.4, 62.9, 62.6, 18.2, 12.2; IR (KBr) 3311, 2943, 2868, 1463, 1383, 1248, 1131, 1014, 965, 883, 682 cm$^{-1}$; HRMS (ESI) [M+H] Calcd. for C$_{15}$H$_{29}$O$_2$Si$_1$ 269.19314, found 269.19288.

TABLE 1

| | Mosher ester data for enynol (−)-4 | | |
|---|---|---|---|
| H | 4 (CDCl$_3$) | (R) Mosher Ester (CDCl$_3$) | (S) Mosher Ester (CDCl$_3$) |
| 1 | 2.58 (d) | 2.65 (d) | 2.60 (d) |
| 2 | 5.93 (ddt) | 5.82 (ddt) | 5.92 (ddt) |
| 3 | 6.05 (m) | 6.09 (m) | 6.17 (m) |
| 4 | 4.31 (m) | 4.26 (m) | 4.30 (m) |

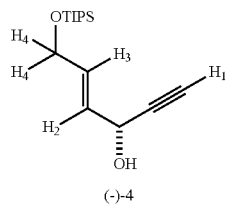

(−)-4

TABLE 1-continued

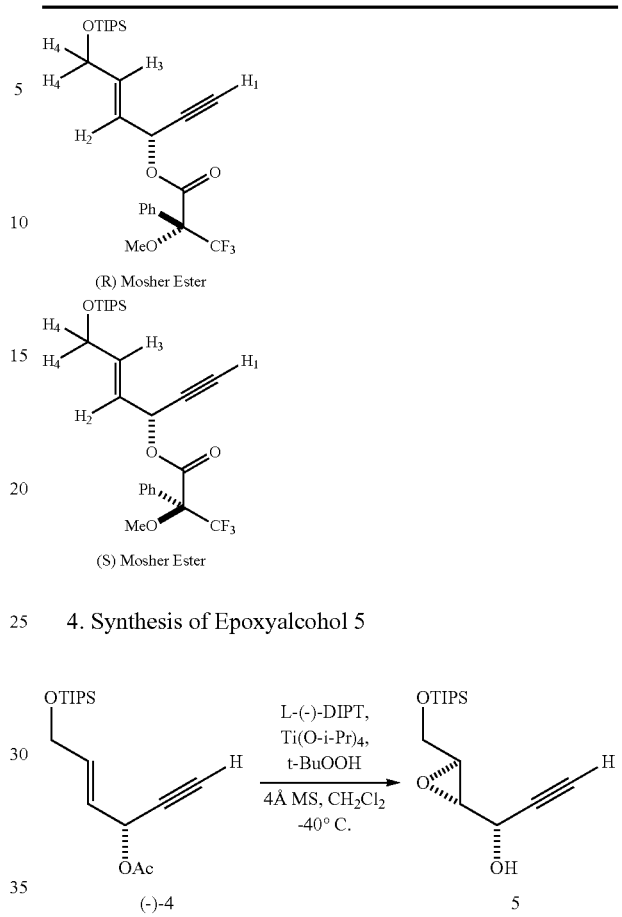

4. Synthesis of Epoxyalcohol 5

Enynol (−)-4 (13.5 g, 50 mmol) was dissolved in CH$_2$Cl$_2$ and 4 Å MS (14 g, powdered) was added to the solution. L-(−)-DIPT (4.2 mL, 20 mmol) was added to the solution, which was then cooled to −40° C. and stirred for 20 minutes. Then Ti(O-i-Pr)$_4$ (4.4 mL, 15 mmol) was added all at once, and the solution was stirred for 20 additional minutes at −40° C. Then t-BuOOH (5.5 M in decane, 18 mL, 100 mmol) was added dropwise via syringe pump over a 3 hour period. After the addition was complete, the reaction was transferred to a −20° C. freezer for 16 hours. The reaction was then warmed to 0° C. A solution of citric acid (3.2 g, 15 mmol) in Et$_2$O: acetone (1:1, 200 mL) was then added to the solution all at once and stirred for 30 minutes. After filtration through celite with a thin top layer of silica gel, the volatiles were evaporated. Chromatography (20:1→10:1→4:1 hexanes:EtOAc) yielded epoxyalcohol 5 as a colorless oil (13.3 g, 94%).

[α]$_D^{23}$=−7.8° (c=1.00, CHCl$_3$); $^1$H NMR (400 MHz, CDCl$_3$) δ 4.68 (m, 1H), 4.03 (dd, J=2.4, 12.0 Hz, 1H), 3.84 (dd, J=4.0, 12.0 Hz, 1H), 3.33 (m, 2H), 2.52 (d, J=2.0 Hz, 1H), 2.16 (d, J=5.6 Hz, 1H), 1.08 (m, 21H); $^{13}$C NMR (100 MHz, CDCl$_3$) δ 80.2, 75.0, 62.3, 60.8, 56.6, 56.4, 18.1, 12.1; IR (KBr) 3413, 3311, 2944, 2867, 2121, 1463, 1385, 1248, 1121, 1014, 883, 783, 683 cm$^{-1}$; HRMS (ESI) [M+H] Calcd. for C$_{15}$H$_{29}$O$_3$Si$_1$ 285.18805, found 285.18817.

TABLE 2

Mosher ester data for epoxyalcohol 5

| H | 5 (CDCl₃) | (R) Mosher Ester | (S) Mosher Ester |
|---|---|---|---|
| 1 | 2.52 (d) | 2.62 (d) | 2.56 (d) |
| 2 | 4.03 (dd) | 3.90 (dd) | 3.94 (dd) |
| 3 | 3.84 (dd) | 3.74 (dd) | 3.78 (dd) |

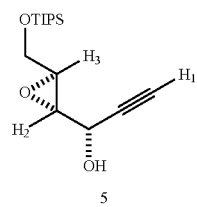

5

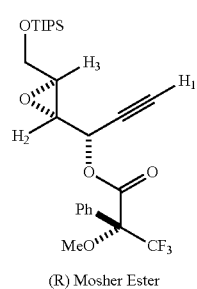

(R) Mosher Ester

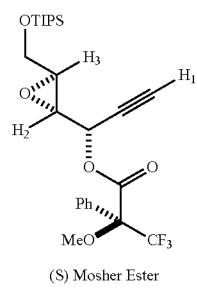

(S) Mosher Ester

5. Preparation of Diol 6

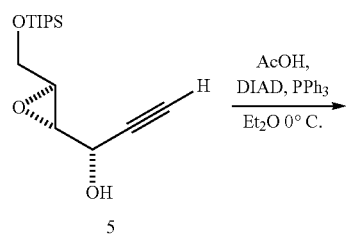

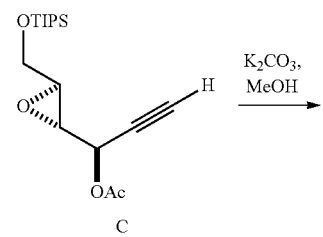

C

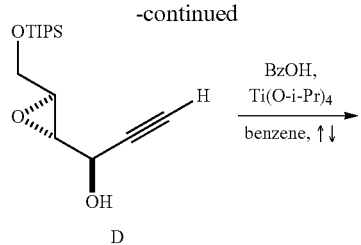

D

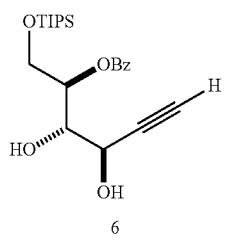

6

Epoxyalcohol 5 (13.3 g, 47 mmol) was dissolved in Et₂O (0.50 M, 100 mL). PPh₃ (13 g, 51 mmol) was then added all at once, and the solution was cooled to 0° C. DIAD (9.8 mL, 51 mmol) was then added all at once, which resulted in the immediate formation of a white precipitate. The reaction was stirred for 15 minutes, at which point Et₂O (100 mL) was added, and the mixture was filtered through celite. The volatiles were evaporated. Chromatography (10:1 hexanes: EtOAc) yielded epoxyacetate C as a yellow oil (15 g, 98%).

$[\alpha]_D^{23}$=−29.6° (c=1.00, CHCl₃); ¹H NMR (400 MHz, CDCl₃) δ 5.25 (dd, J=2.4, 6.4 Hz, 1H), 3.99 (dd, J=2.8, 12.0 Hz, 1H), 3.85 (dd, J=4.0, 12.0 Hz, 1H), 3.32 (dd, J=2.0, 6.4 Hz, 1H), 3.21 (m, 1H), 2.53 (d, J=2.4 Hz, 1H), 2.15 (s, 3H), 1.08 (m, 21H); ¹³C NMR (100 MHz, CDCl₃) δ 169.7, 77.3, 75.5, 64.5, 62.2, 56.9, 54.9, 21.0, 18.1, 12.1; IR (KBr) 3276, 2943, 2867, 1750, 1464, 1371, 1227, 1139, 1024, 883, 684 cm⁻¹; HRMS (ESI) [M+H] Calcd. for C₁₇H₃₁O₄Si₁ 327.19861, found 327.19826.

Epoxyacetate C (15 g, 46 mmol) was dissolved in MeOH (0.50 M, 100 mL). K₂CO₃ (7.9 g, 57 mmol) was added all at once. The reaction was complete after 30 minutes of stirring at room temperature. The reaction contents was diluted with Et₂O (100 mL) and quenched with a saturated solution of NH₄Cl (150 mL). The aqueous layer was extracted with Et₂O (2×50 mL). The organic layers were combined and dried with MgSO₄. Following filtration and removal of the volatiles under reduced pressure, epoxyalcohol D was isolated as a colorless oil without further purification (11 g, 84%).

$[\alpha]_D^{23}$=−8.3° (c=1.27, CHCl₃); ¹H NMR (600 MHz, CDCl₃) δ 4.40 (ddd, J=2.4, 4.2, 7.8 Hz, 1H), 3.99 (dd, J=3.0, 12.0 Hz, 1H), 3.82 (dd, J=2.4, 12.0 Hz, 1H), 3.27 (dd, J=2.4, 4.8 Hz, 1H), 2.53 (d, J=2.4 Hz, 1H), 2.23 (d, J=7.8 Hz, 1H), 1.07 (m, 21H); ¹³C NMR (150 MHz, CDCl₃) δ 81.2, 74.2, 62.5, 61.7, 57.5, 56.7, 18.1, 12.1; IR (KBr) 3431, 3293, 2946, 2870, 1463, 1385, 1247, 1124, 1016, 883, 782, 682 cm⁻¹; HRMS (ESI) [M+H] Calcd. for C₁₅H₂₉O₃Si₁ 285.18805, found 285.18807.

TABLE 3

Mosher ester data for epoxyalcohol D

| H | D (CDCl₃) | (R) Mosher Ester | (S) Mosher Ester |
|---|---|---|---|
| 1 | 2.53 (d) | 2.58 (d) | 2.63 (d) |
| 2 | 3.82 (dd) | 3.81 (dd) | 3.78 (dd) |
| 3 | 3.99 (dd) | 3.94 (dd) | 3.91 (dd) |

TABLE 3-continued

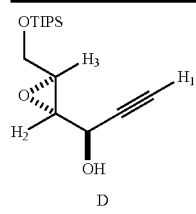

D

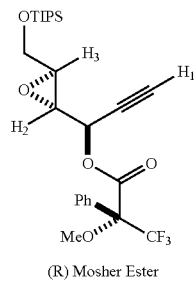

(R) Mosher Ester

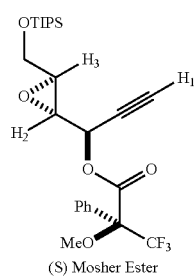

(S) Mosher Ester

Epoxyalcohol D (11 g, 37 mmol) was dissolved in benzene (3.0 M, 12 mL). Benzoic acid (6.8 g, 56 mmol) was added to the solution, and the flask was equipped with a reflux condenser. The reaction was then heated to 75° C., at which point all of the benzoic acid had dissolved. Ti(O-i-Pr)$_4$ (13.3 mL, 45 mmol) was then carefully added to the flask all at once. The reaction was heated at reflux for 2 hours, at which point Et$_2$O (100 mL) was added. Then H$_2$SO$_4$ (5% aqueous solution, 100 mL) was added to the solution, and the biphasic mixture was stirred until each layer was transparent (typically 2 hours). The aqueous layer was extracted with EtOAc (1×100 mL). The organic extracts were combined and dried with MgSO$_4$. After filtration and evaporation of the volatiles, chromatography (9:1→4:1→2:1 hexanes:EtOAc) provided diol 6 as a yellow oil (11.5 g, 77%).

$[\alpha]_D^{23}$=−4.7° (c=1.12, CHCl$_3$); $^1$H NMR (400 MHz, CDCl$_3$) δ 8.09 (m, 2H), 7.59 (m, 1H), 7.47 (m, 2H), 5.23 (ddd, J=3.5, 4.0, 6.4 Hz, 1H), 4.52 (dd, J=2.4, 3.6 Hz, 1H), 4.20 (dd, J=4.0, 11.2 Hz, 1H), 4.14 (m, 3H), 2.51 (d, J=2.4 Hz, 1H), 1.07 (m, 21H); $^{13}$C NMR (100 MHz, CDCl$_3$) δ 166.2, 133.9, 133.6, 130.4, 130.1, 129.7, 128.7, 82.0, 75.0, 74.4, 72.7, 63.5, 63.0, 18.1, 11.9; IR (KBr) 3434, 3298, 2956, 2866, 1715, 1603, 1454, 1258, 1119, 1069, 882, 687 cm$^{−1}$; HRMS (ESI) [M+H] Calcd. for C$_{22}$H$_{35}$O$_5$Si$_1$ 407.22483, found 407.22446.

6. Preparation of Acetonide 7

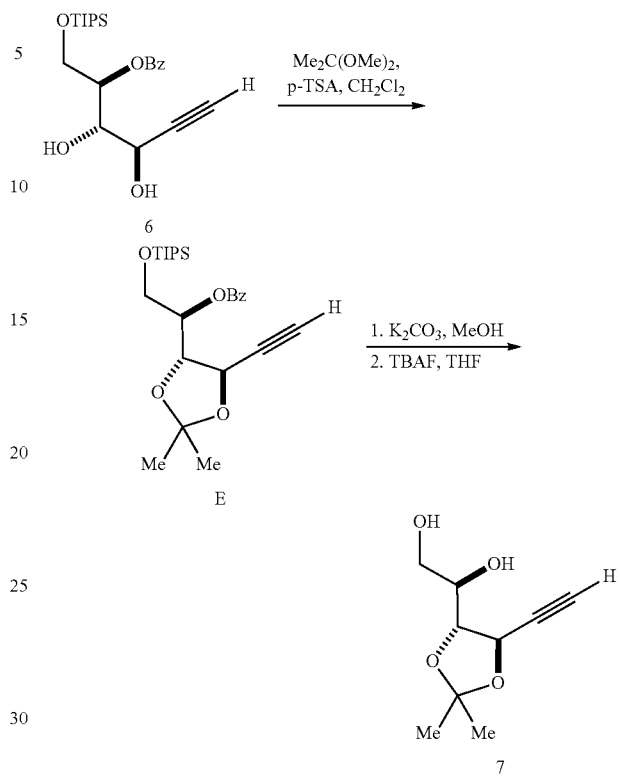

Diol 6 (9.6 g, 24 mmol) was dissolved in 2,2-dimethoxypropane (0.50 M, 48 mL) and then p-TSA (450 mg, 2.4 mmol) was added to the solution all at once. The reaction was stirred for one hour at r.t. and then diluted with CH$_2$Cl$_2$ (100 mL). The reaction was quenched by the addition of a saturated solution of NaHCO$_3$ (50 mL). The aqueous layer was extracted with CH$_2$Cl$_2$ (2×50 mL). The organic extracts were combined and dried with MgSO$_4$. After filtration, the volatiles were evaporated under reduced pressure. Chromatography (4:1 hexanes:EtOAc) gave acetonide E as a pale yellow oil (8.4 g, 79%).

$[\alpha]_D^{23}$=+2.7 (c 1.2, CHCl$_3$); $^1$H NMR (400 MHz, CDCl$_3$) δ 8.07 (m, 2H), 7.57 (m, 1H), 7.44 (m, 2H), 5.34 (dd, J=4.8, 10.4 Hz, 1H), 4.83 (dd, J=2.0, 6.8 Hz, 1H), 4.52 (dd, J=6.0, 6.8 Hz, 1H), 4.07 (dd, J=4.4, 10.8 Hz, 1H), 4.01 (dd, J=4.4, 10.8 Hz, 1H), 2.48 (d, J=2.0 Hz, 1H), 1.52 (s, 3H), 1.38 (s, 3H), 1.04 (m, 21H); $^{13}$C NMR (100 MHz, CHCl$_3$) δ 165.9, 133.3, 130.1, 130.0, 128.5, 111.1, 81.6, 80.2, 74.8, 74.1, 67.5, 62.4; IR (KBr) 3310, 2943, 2868, 1724, 1464, 1383, 1269, 1109, 1068, 881 cm$^{−1}$; HRMS (ESI) [M+H] Calcd. for C$_{25}$H$_{39}$O$_5$Si$_1$ 447.25613, found 447.25568.

Acetonide E (8.4 g, 19 mmol) was dissolved in MeOH (0.50 M, 40 mL). K$_2$CO$_3$ (2.7 g, 19 mmol) was added all at once, and the reaction was stirred for 1 hour at r.t. The reaction was diluted with Et$_2$O (100 mL) and quenched with a saturated solution of NH$_4$Cl (150 mL). The aqueous layer was extracted with Et$_2$O (2×50 mL). The organic layers were combined and dried with MgSO$_4$. After filtration, the volatiles were evaporated under reduced pressure, and the crude oil was then re-dissolved in THF (0.50 M, xmL). TBAF (1.0 M in THF, 19 mL, 19 mmol) was then added to the solution all at once, and the reaction was stirred at r.t. for 2 hours. The reaction was then diluted with EtOAc (100 mL) and quenched with H$_2$O (100 mL). The aqueous layer was extracted with EtOAc (2×100 mL). The organic extracts were combined and dried with MgSO$_4$. Chromatography (4:1→0:1 hexanes:EtOAc) provided 7 as a pale yellow oil (5.1 g, 80%).

$[\alpha]_D^{23}$=+9.6 (c 1.10, CHCl$_3$); $^1$H NMR (400 MHz, CDCl$_3$) δ 4.70 (dd, J=2.0, 7.2 Hz, 1H), 4.15 (dd, J=5.2, 7.2 Hz, 1H), 3.92 (m, 1H), 3.81 (m, 1H), 3.72 (m, 1H), 2.57 (d, J=2.0 Hz, 1H), 1.51 (s, 3H), 1.44 (s, 3H); $^{13}$C NMR (100 MHz, CDCl$_3$) δ 110.9, 82.1, 81.6, 74.9, 71.5, 66.6, 63.3, 27.0, 26.1; IR (KBr) 3417, 3292, 2989, 2918, 1383, 1215, 1065 cm$^{-1}$; HRMS (ESI) [M+H] Calcd. for C$_9$H$_{15}$O$_4$ 187.09649, found 187.09593.

7. Preparation of Benzylidene Acetal 8

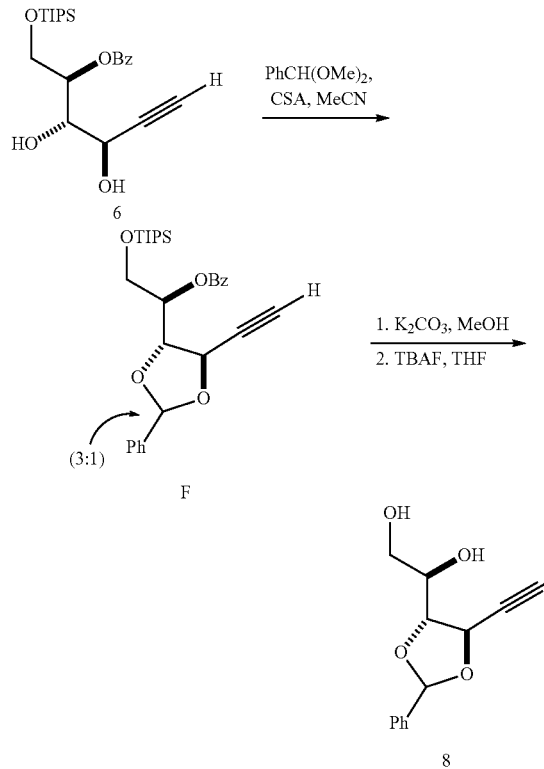

Diol 6 (10.6 g, 26 mmol) was dissolved in MeCN (0.25 M, 100 mL). Benzylidene dimethyl acetal (4.4 mL, 29 mmol) was added all at once, followed by the addition of CSA (300 mg, 1.3 mmol). The reaction was stirred at r.t. for three hours. The reaction was then diluted with CH$_2$Cl$_2$ (100 mL) and quenched by the addition of a saturated solution of NaHCO$_3$. The aqueous layer was extracted with EtOAc (100 mL). The organic extracts were combined and dried with MgSO$_4$. After filtration and evaporation of the volatiles, chromatography (20:1 hexanes:EtOAc) afforded benzylidene acetal F (3:1 mixture of diastereomers) as a colorless oil (10.0 g, 78%).

$[\alpha]_D^{23}$=−32.6 (c 1.00, CHCl$_3$); $^1$H NMR (400 MHz, CDCl$_3$) δ 8.08 (m, 2H), 7.29-7.26 (m, 9H), 6.04 (s, 1H), 5.39 (dd, J=4.0, 8.8 Hz, 1H), 5.14 (dd, J=2.0, 4.8 Hz, 1H), 4.66 (t, J=4.8 Hz, 1H), 4.09 (m, 2H), 2.59 (d, J=2.0 Hz, 1H), 1.05 (m, 21H); $^{13}$C NMR (100 MHz, CDCl$_3$) δ 165.9, 136.0, 133.5, 133.4, 130.0, 129.8, 129.7, 128.6, 128.5, 128.5, 128.4, 127.1, 126.9, 105.2, 103.8, 81.9, 81.4, 80.2, 75.3, 74.2, 74.1, 68.9, 67.7, 62.4, 62.3, 18.1, 12.1; IR (KBr) 3305, 3068, 2926, 2121, 1724, 1603, 1454, 1267, 1066, 883, 636 cm$^{-1}$; HRMS (ESI) [M+H] Calcd. for C$_{29}$H$_{39}$O$_5$Si$_1$ 495.25613, found 495.25551.

Benzylidene acetal F (10.0 g, 20 mmol) was dissolved in MeOH (0.50 M, 40 mL). K$_2$CO$_3$ (4.2 g, 30 mmol) was added all at once and the reaction was stirred for 1 hour at r.t. The reaction was diluted with Et$_2$O (100 mL) and quenched with a saturated solution of NH$_4$Cl (150 mL). The aqueous layer was extracted with Et$_2$O (2×50 mL). The organic layers were combined and dried with MgSO$_4$. After filtration, the volatiles were evaporated under reduced pressure, and the crude oil was then re-dissolved in THF (0.50 M, 40 mL). TBAF (1.0 M in THF, 40 mL, 40 mmol) was then added to the solution all at once, and the reaction was stirred at r.t. for 2 hours. The reaction was then diluted with EtOAc (100 mL) and quenched with H$_2$O (100 mL). The aqueous layer was extracted with EtOAc (2×100 mL). The organic extracts were combined and dried with MgSO$_4$. After filtration and evaporation of the volatiles under reduced pressure, the resulting semi-solid was re-dissolved in a minimal amount of acetone and purified via chromatography on a short plug of silica gel (4:1→0:1 hexanes:EtOAc) to give alkynyl diol 8 as a white solid (3.5 g, 75%).

$[\alpha]_D^{23}$=−12.1 (c 1.30, MeOH); $^1$H NMR (400 MHz, CDCl$_3$) δ 7.60 (m, 5H), 6.03 (s, 1H), 4.98 (dd, J=2.0, 5.2 Hz, 1H), 4.25 (dd, J=5.2, 10.4 Hz, 1H), 3.92 (m, 1H), 3.84 (m, 1H), 3.77 (m, 1H), 2.64 (d, J=2.0 Hz, 1H), 2.48 (d, J=4.8 Hz, 1H), 1.91 (m, 1H); $^{13}$C NMR (100 MHz, CD$_3$OD) δ 137.8, 130.8, 130.6, 129.5, 129.4, 128.3, 128.2, 106.1, 105.1, 84.6, 83.7, 82.7, 76.7, 76.3, 73.8, 72.9, 69.4, 64.4; IR (KBr) 3348, 2927, 2348, 1643, 1090, 1068, 758 cm$^{-1}$; HRMS (ESI) [M+H] Calcd. for C$_{13}$H$_{15}$O$_4$ 235.09649, found 235.09669.

8. Cycloisomerization of 7 to Glycal 9 and Protection as Silyl Ether 11

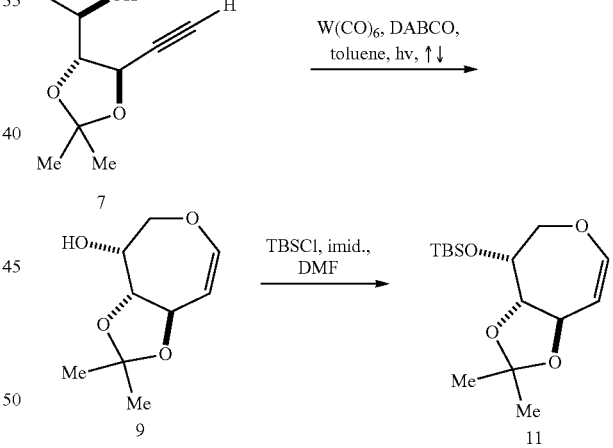

Alkynyl diol 7 (1.7 g, 9.3 mmol) was dissolved in toluene (0.20 M, 47 mL). DABCO (2.1 g, 19 mmol) and W(CO)$_6$ (980 mg, 2.8 mmol) were sequentially added to the solution. The round bottom flask was equipped with a reflux condenser, placed into a Rayonet photoreactor, and irradiated at 350 nm (without cooling) for 12 hours. The volatiles were then evaporated, and the crude mixture containing glycal alcohol 9 was dissolved in DMF (1.0 M, 9.3 mL). TBSCl (2.1 g, 14 mmol) was added to the solution, followed by the addition of imidazole (1.3 g, 19 mmol). The reaction was stirred for 2 hours. The reaction was then diluted with CH$_2$Cl$_2$ (100 mL) and quenched with H$_2$O (100 mL). The aqueous layer was extracted with CH$_2$Cl$_2$ (2×50 mL). The organic extracts were combined and dried with MgSO$_4$. After filtration, the volatiles were evaporated under reduced pressure. Chromatography (4:1 hexanes:EtOAc) afforded glycal 11 as a colorless oil (2.2 g, 80%)

$[\alpha]_D^{23}$=−46.9 (c 1.50, CHCl$_3$); $^1$H NMR (400 MHz, CDCl$_3$) δ 6.36 (ddd, J=1.2, 3.2, 6.4 Hz, 1H), 5.16 (ddd, J=1.6, 2.8, 6.4 Hz, 1H), 4.89 (m, 1H), 4.37 (m, 1H), 4.09 (ddd, J=0.80, 4.8, 12.0 Hz, 1H), 4.82 (ddd, J=0.80, 3.6, 9.6 Hz, 1H), 3.64 (ddd, J=0.80, 7.6, 12.4 Hz, 1H), 1.45 (s, 3H), 1.42 (s, 3H), 0.91 (s, 9H), 0.11 (s, 3H), 0.093 (s, 3H); $^{13}$C NMR (100 MHz, CDCl$_3$) δ 148.5, 109.9, 109.4, 80.4, 74.5, 71.9, 67.3, 27.5, 26.9, 25.9, 18.4, −4.25, −4.89; IR (KBr) 2933, 2858, 1639, 1464, 1371, 1246, 1171, 1088, 951, 835, 779 cm$^{-1}$; HRMS (ESI) [M+H−H$_2$] Calcd. for C$_{15}$H$_{27}$O$_4$Si$_1$ 299.16731, found 299.16706.

9. Cycloisomerization of 8 to Glycal 10 and Protection as Benzyl Ether 12

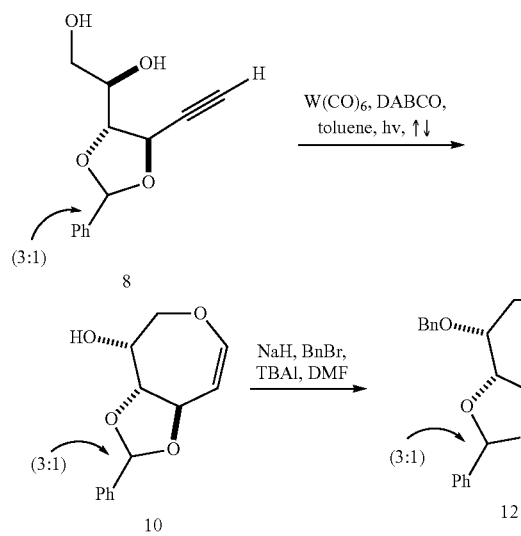

Alkynyl diol 8 (850 mg, 3.6 mmol) was dissolved in toluene (0.20 M, 18 mL). DABCO (810 mg, 7.3 mmol) and W(CO)$_6$ (190 mg, 0.54 mmol) were sequentially added to the solution. The round bottom flask was equipped with a reflux condenser, placed into a Rayonet photoreactor, and irradiated at 350 nm (without cooling) for 16 hours. The volatiles were then evaporated, and the crude mixture was dissolved in CH$_2$Cl$_2$ (100 mL). The organic layer was then washed with a saturated solution of NH$_4$Cl (75 mL). The aqueous layer was extracted with CH$_2$Cl$_2$ (75 mL). The organic extracts were combined and dried with MgSO$_4$. After filtration, the volatiles were evaporated under reduced pressure. The crude mixture containing glycal alcohol 10 was then dissolved in DMF (0.20 M, 18 mL). The solution was cooled to 0° C., and NaH (60% dispersion in mineral oil, 220 mg, 5.5 mmol) was added. The reaction was stirred for 20 minutes. Then BnBr (0.65 mL, 5.5 mmol) was added all at once, followed by the addition of TBAI (10 mg). The reaction was warmed to r.t. and stirred overnight. The reaction was then diluted with Et$_2$O (25 mL) and quenched by the addition of a saturated solution of NH$_4$Cl (25 mL). The aqueous layer was then extracted with EtOAc (1×50 mL). The organic layers were combined and dried with MgSO$_4$. After filtration, the volatiles were evaporated under reduced pressure, and chromatography (25:1→20:1 hexanes:EtOAc) provided glycal 12 (3:1 mixture of diastereomers) as a yellow oil (1.2 g, Quant.).

$[\alpha]_D^{23}$=+24.3 (c 1.10, CHCl$_3$); $^1$H NMR (400 MHz, CDCl$_3$) δ 7.29-7.57 (m, 10H), 6.39 (dd, J=2.0, 6.4 Hz, 1H), 6.13 (s, 1H), 5.26 (dd, J=2.0, 6.8 Hz, 1H), 5.09 (m, 1H), 4.95 (d, J=11.6 Hz, 1H), 4.68 (d, J=11.6 Hz, 1H), 4.39 (m, 1H), 4.15 (m, 2H), 3.80 (m, 1H); $^{13}$C NMR (100 MHz, CDCl$_3$) δ 149.1, 148.6, 139.2, 138.7, 138.3, 129.7, 129.4, 128.7, 128.6, 128.6, 128.1, 127.9, 127.8, 126.8, 126.8, 109.6, 108.7, 104.7, 83.2, 81.8, 74.9, 73.9, 73.8, 73.4, 72.9, 72.3, 72.2, 72.0; IR (KBr) 3292, 3153, 2927, 1460, 1406, 1068, 966, 912, 758, 698 cm$^{-1}$; HRMS (ESI) [M+H] Calcd. for C$_{20}$H$_{21}$O$_4$ 325.14344, found 325.14352.

10. Protection of Glycal Alcohol 10 as Trimethylsilylethoxymethyl Ether 13

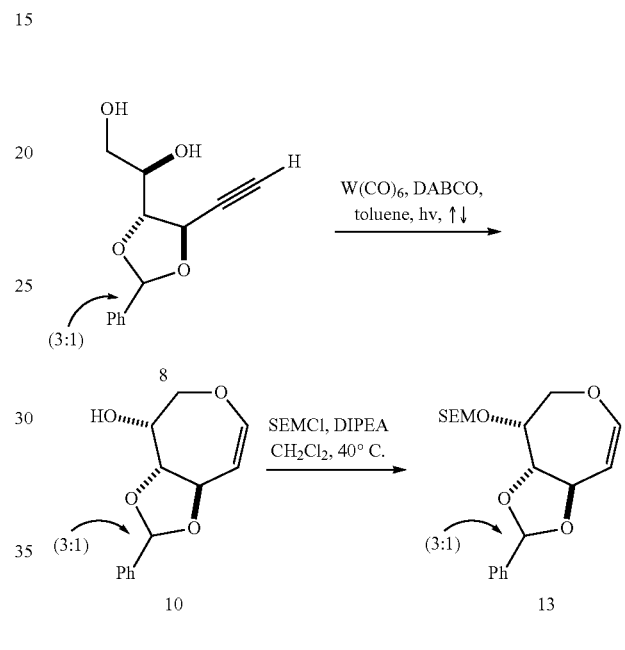

The glycal alcohol 10 was prepared as described above by the irradiation of alkynyl diol 7 (2.0 g, 8.5 mmol) in toluene (0.20 M, 43 mL) with DABCO (1.9 g, 17 mmol) and W(CO)$_6$ (750 mg, 2.1 mmol) for 20 hours. The crude mixture containing 10 was then dissolved in CH$_2$Cl$_2$ (1.0 M, 8.5 mL), and DIPEA (7.4 mL, 43 mmol) was added to the solution all at once. Then SEMCl (3.0 mL, 17 mmol) was carefully added to the reaction. The reaction was stirred at 40° C. for 3 hours. The reaction was then diluted with EtOAc (100 mL) and washed with H$_2$O (3×50 mL). The organic layer was dried with MgSO$_4$. After filtration, the volatiles were evaporated under reduced pressure, and chromatography (9:1 hexanes:EtOAc) provided glycal 13 (3:1 mixture of benzylidene acetal diastereomers) as a yellow oil (2.3 g, 75%).

$[\alpha]_D^{23}$=+49.8 (c 1.00, CHCl$_3$); $^1$H NMR (400 MHz, CDCl$_3$) δ 7.36-7.53 (m, 5H), 6.41 (dd, J=2.0, 6.4 Hz, 1H), 6.09 (s, 1H), 5.29 (dd, J=1.6, 6.4 Hz, 1H), 5.00 (m, 1H), 4.92 (d, J=7.2 Hz, 1H), 4.79 (d, J=6.8 Hz, 1H), 4.56 (m, 1H), 4.19 (dd, J=4.8, 12.8 Hz, 1H), 4.05 (dd, J=3.6, 9.6 Hz, 1H), 3.83 (dd, J=7.6, 12.4 Hz, 1H), 3.73 (m, 1H), 3.55 (m, 1H), 0.93 (m, 2H), −0.002 (s, 9H); $^{13}$C NMR (100 MHz, CDCl$_3$) δ 148.6, 139.3, 129.4, 128.6, 126.7, 110.5, 104.7, 95.4, 82.4, 72.6, 72.2, 70.8, 65.7, 18.4, −1.19; IR (KBr) 2953, 2892, 1639, 1247, 1116, 1055, 837, 697 cm$^{-1}$; HRMS (ESI) [M+NH$_4^+$] Calcd. for C$_{19}$H$_{32}$O$_5$N$_1$Si$_1$ 382.20443, found 382.20462.

Example 2

B. Preparation of Various D-Mannoseptanoside Derivatives 21-25

1. Epoxidation of Glycal 11 and Conversion to 14 and 15

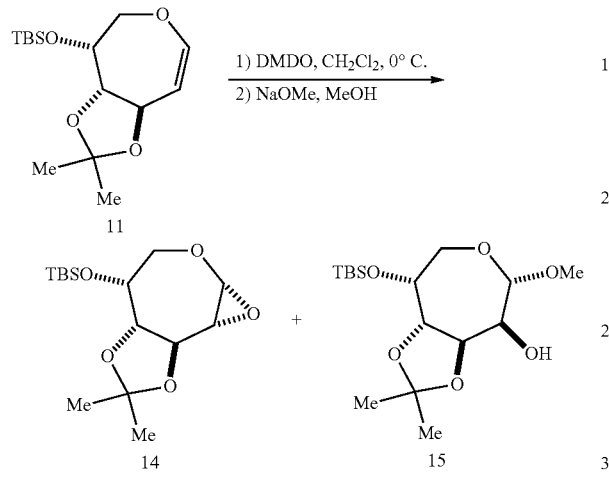

Glycal 11 (500 mg, 1.7 mmol) was dissolved in CH$_2$Cl$_2$ (0.10 M, 10 mL) and cooled to 0° C. Then dimethyldioxirane (DMDO, 34 mL, 3.4 mmol) was added to the solution, and the reaction was stirred at 0° C. for 30 minutes. The volatiles were then evaporated under reduced pressure. The crude epoxide was then dissolved in MeOH (0.10 M, 10 mL). NaOMe (0.50 M solution in MeOH, 6.8 mL, 3.4 mmol) was added all at once. The reaction was allowed to stir for 16 hours at r.t. Then the reaction was diluted with CH$_2$Cl$_2$ (100 mL) and quenched with a saturated solution of NH$_4$Cl (50 mL). The aqueous layer was extracted with CH$_2$Cl$_2$ (1×50 mL). The organic were combined and dried with MgSO$_4$. After filtration and evaporation of the volatiles under reduced pressure, chromatography (4:1→2:1 hexanes EtOAc) gave epoxide 14 (220 mg, 40%) and methyl glycoside 15 (230 mg, 38%).

14: [α]$_D^{23}$=−66.4 (c 0.50, CHCl$_3$); $^1$H NMR (400 MHz, CDCl$_3$) δ 4.75 (d, J=2.0 Hz, 1H), 4.32 (dd, J=4.4, 9.6 Hz, 1H), 4.18 (m, 1H), 3.82 (dd, J=2.4, 10.0 Hz, 1H), 3.77 (dd, J=3.2, 13.2 Hz, 1H), 3.68 (dd, J=1.6, 13.6 Hz, 1H), 3.02 (dd, J=2.4, 4.4 Hz, 1H), 1.46 (s, 3H), 1.41 (s, 3H), 0.91 (s, 9H), 0.088 (s, 3H), 0.080 (s, 3H); $^{13}$C NMR (100 MHz, CDCl$_3$) δ 111.2, 79.1, 77.8, 74.8, 68.6, 67.4, 56.3, 27.4, 27.1, 25.9, 18.4, −4.25, −4.89; IR (KBr) 3458, 2931, 1452, 1381, 1252, 1032, 831, 688 cm$^{-1}$; HRMS (ESI) [M+H] Calcd. for C$_{15}$H$_{29}$O$_5$Si$_1$ 317.17788, found 317.17751.

15: [α]$_D^{23}$=−38.2 (c 0.50, CHCl$_3$); $^1$H NMR (400 MHz, CDCl$_3$) δ 4.49 (dd, J=4.8, 9.2 Hz, 1H), 4.16 (d, J=6.0 Hz, 1H), 4.14 (m, 1H), 4.12 (d, J=1.6 Hz, 1H), 4.09 (m, 1H), 4.02 (dd, J=2.0, 9.6 Hz, 1H), 3.59 (dd, J=2.0, 13.6 Hz, 1H), 3.46 (s, 3H), 1.45 (s, 3H), 1.44 (s, 3H), 0.926 (s, 9H), 0.102 (s, 3H), 0.093 (s, 3H); $^{13}$C NMR (100 MHz, CDCl$_3$) δ 111.8, 109.7, 76.3, 74.9, 73.3, 70.2, 70.0, 56.3, 27.4, 27.1, 26.1, 18.4, −4.19, −4.74; IR (KBr) 3456, 2931, 1464, 1369, 1252, 1041 cm$^{-1}$; HRMS (ESI) [M+H] Calcd. for C$_{16}$H$_{33}$O$_6$Si$_1$ 349.20409, found 349.20425.

2. Preparation of D-Mannoseptanoside Acceptor Synthon 16

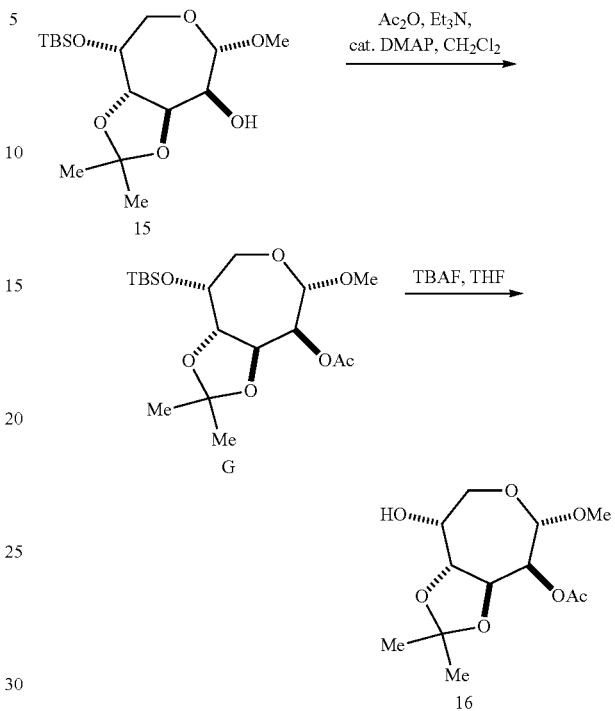

Methyl glycoside 15 (200 mg, 0.57 mmol) was dissolved in CH$_2$Cl$_2$ (0.10 M, 5.7 mL). Ac$_2$O (0.10 mL, 1.1 mmol) and Et$_3$N (0.20 mL, 1.1 mmol) were sequentially added to the solution, followed by DMAP (10 mg). The reaction was stirred for 1 hour at r.t. The reaction was diluted with CH$_2$Cl$_2$ (50 mL) and quenched by the addition of H$_2$O (50 mL). The aqueous layer was extracted with CH$_2$Cl$_2$ (1×50 mL). The organic extracts were combined and dried with MgSO$_4$. After filtration and evaporation of the volatiles under reduced pressure, chromatography (9:1→4:1 hexanes:EtOAc) to give acetate G (220 mg, Quant.).

[α]$_D^{23}$=−17.9 (c 0.50, CHCl$_3$); $^1$H NMR (400 MHz, CDCl$_3$) δ 5.39 (t, J=5.2 Hz, 1H), 4.56 (dd, J=4.4, 9.2 Hz, 1H), 4.29 (d, J=5.2 Hz, 1H), 4.18 (m, 1H), 4.09 (dd, J=2.4, 9.2 Hz, 1H), 4.03 (dd, J=2.8, 13.2 Hz, 1H), 3.64 (dd, J=2.4, 12.8 Hz, 1H), 3.39 (s, 3H), 2.11 (s, 3H), 1.41 (s, 3H), 1.35 (s, 3H), 0.916 (s, 9H), 0.094 (s, 3H), 0.085 (s, 3H); $^{13}$C NMR (100 MHz, CDCl$_3$) δ 169.8, 109.9, 108.5, 76.8, 73.2, 72.3, 71.4, 69.3, 56.3, 27.3, 26.9, 26.1, 21.2, 18.4, −4.19, −4.74; IR (KBr) 2931, 2858, 1753, 1369, 1232, 1086, 1034, 829 cm$^{-1}$; HRMS (ESI) [M+H] Calcd. for C$_{18}$H$_{35}$O$_7$Si$_1$ 391.21466, found 391.21394.

Acetate G (220 mg, 0.57 mmol) was dissolved in THF (0.20 M, 3.0 mL). TBAF (1.0 M solution in THF, 0.63 mL, 0.63 mmol) was then added all at once. The reaction was stirred at r.t. for 3 hours. The reaction was diluted with EtOAc (100 mL) and quenched by the addition of H$_2$O (100 mL). The aqueous layer was extracted with EtOAc (1×100 mL). The organic extracts were combined and dried with MgSO$_4$. After filtration and evaporation of the volatiles under reduced pressure, chromatography (2:1→1:1 hexanes:EtOAc) afforded alcohol 16 as a colorless oil (100 mg, 64%).

[α]$_D^{23}$=−11.3 (c 1.50, CHCl$_3$); $^1$H NMR (400 MHz, CDCl$_3$) δ 5.42 (t, J=4.0 Hz, 1H), 4.46 (dd, J=5.2, 8.8 Hz, 1H), 4.36 (d, J=4.0 Hz, 1H), 4.21 (m, 1H), 4.17 (d, J=3.2 Hz, 1H), 4.14 (dd, J=3.2, 13.2 Hz, 1H), 3.73 (dd, J=3.2, 13.2 Hz, 1H), 3.39 (s, 3H), 2.48 (2, 1H), 2.12 (s, 3H), 1.44 (s, 3H), 1.38 (s, 3H); $^{13}$C NMR (100 MHz, CDCl$_3$) δ 169.7, 109.9, 107.3, 76.1, 72.2, 71.4, 69.0, 67.5, 56.3, 27.1, 26.9, 21.2; IR (KBr) 3533, 3435, 2966, 2918, 1730, 1443, 1373, 1234, 1171, 1078, 877 cm$^{-1}$; HRMS (ESI) [M+H] Calcd. for $C_{12}H_{21}O_7$ 277.12818, found 277.12809.

3. Reductive Opening of Benzylidene Acetal 12 and Protection as Benzyl Ether 17

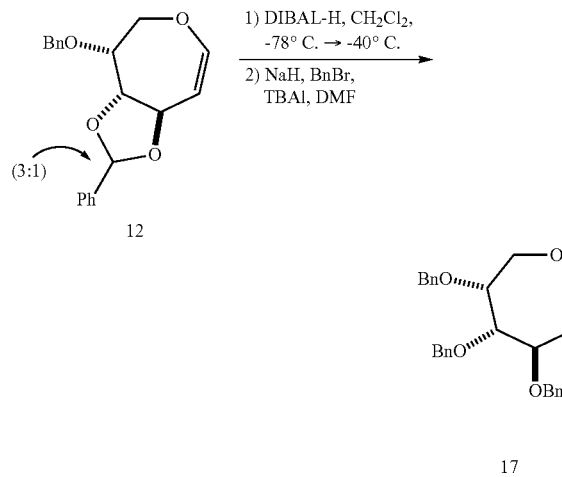

Glycal 12 (1.2 g, 3.4 mmol) was dissolved in CH$_2$Cl$_2$ (0.20 M, 7.0 mL). The solution was cooled to −78° C. and DIBAL-H (1.0 M solution in CH$_2$Cl$_2$, 30 mL, 30 mmol) was added over a period of 5 minutes. The reaction was slowly warmed to −40° C. and allowed to stir for 2 hours. Then the reaction was diluted with EtOAc (100 mL) and quenched by the addition of a saturated solution of Rochelle's salt (100 mL). The resulting gelatinous mixture was allowed to stir for 2 hours until each layer was transparent and could be easily separated. The aqueous layer was extracted with EtOAc (2×50 mL). The organic extracts were combined and dried with MgSO$_4$. After filtration, the volatiles were evaporated under reduced pressure. The crude mixture was then dissolved in DMF (0.20 M, 20 mL) was added to the solution. The solution was cooled to 0° C., and NaH (60% dispersion in mineral oil, 200 mg, 4.8 mmol) was added all at once. The reaction was allowed to stir for 20 minutes. Then BnBr (0.57 mL, 4.8 mmol) was added all at once, followed by the addition of TBAI (10 mg). The reaction was allowed to warm to r.t. and stirred for 2 hours. After diluting with Et$_2$O (50 mL), a saturated solution of NH$_4$Cl (25 mL) was slowly added to quench the reaction. The aqueous layer was then extracted with EtOAc (2×20 mL). The organic extracts were combined and dried with MgSO$_4$. After filtration and evaporation of the volatiles under reduced pressure, chromatography (20:1→9:1 hexanes:EtOAc) gave 17 as a colorless oil (810 mg, 58%).

$[α]_D^{23}$=−59.7 (c 1.00, CHCl$_3$); $^1$H NMR (400 MHz, CDCl$_3$) δ 7.33 (m, 15H), 6.32 (dd, J=0.80, 7.6 Hz, 1H), 4.76 (dd, J=4.8, 7.6 Hz, 1H), 4.72 (s, 2H), 4.69 (d, J=6.4 Hz, 2H), 4.68 (d, J=11.6 Hz, 1H), 4.56 (d, J=12.0 Hz, 1H), 4.21 (m, 2H), 3.99 (m, 1H), 3.86 (m, 1H); $^1$H NMR (400 MHz, C$_6$D$_6$ [for better resolution of chemical shift and coupling constant values]) 7.33-7.07 (m, 15H), 6.29 (dd, J=0.80, 8.0 Hz, 1H), 4.69 (dd, J=4.8, 8.0 Hz, 1H), 4.61-4.38 (m, 6H), 4.29 (ddd, J=0.80, 4.8, 6.4 Hz, 1H), 4.24 (dd, J=8.4, 12.0 Hz, 1H), 3.94 (ddd, J=2.4, 4.4, 7.6 Hz, 1H), 3.85 (dd, J=2.0, 6.4 Hz, 1H), 3.74 (dd, J=1.6, 12.0 Hz, 1H); $^{13}$C NMR (100 MHz, CDCl$_3$) δ 147.2, 138.8, 138.7, 138.4, 128.6, 128.5, 128.5, 127.9, 127.9, 127.9, 127.8, 127.8, 106.3, 80.6, 76.4, 74.5, 73.4, 72.1, 71.9, 68.6; IR (KBr) 3031, 2872, 1650, 1496, 1454, 1295, 1070, 732, 698 cm$^{-1}$; HRMS (ESI) [M+H] Calcd. for $C_{27}H_{29}O_4$ 417.20604, found 417.20567.

4. Reductive Opening of Benzylidene Acetal 13 and Protection as Benzyl Ether 18

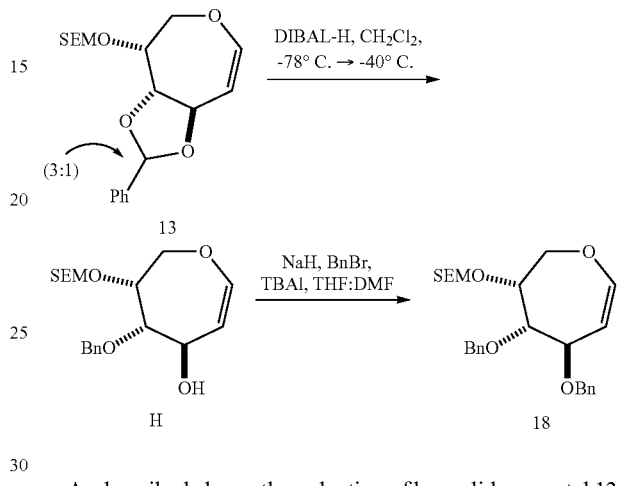

As described above, the reduction of benzylidene acetal 13 (1.3 g, 3.6 mmol) in CH$_2$Cl$_2$ (1.0 M, 4.0 mL) with DIBAL-H (1.0 M solution in CH$_2$Cl$_2$, 18 mL, 18 mmol) provided a single alcohol H, which was purified by chromatography (9:1→4:1 hexanes:EtOAc) to give a colorless oil (1.3 g, Quant.).

$[α]_D^{23}$=−74.4 (c 1.30, CHCl$_3$); $^1$H NMR (400 MHz, CDCl$_3$) δ 7.36 (m, 5H), 6.38 (dd, J=1.6, 7.2 Hz, 1H), 4.86 (m, 3H), 4.73 (d, J=11.2 Hz, 1H), 4.58 (d, J=11.2 Hz, 1H), 4.34 (ddd, J=1.6, 3.2, 8.4 Hz, 1H), 4.12 (m, 2H), 3.97 (dd, J=2.0, 12.4 Hz, 1H), 3.90 (dd, 3H), 3.69 (m, 2H), 2.99 (d, J=3.6 Hz, 1H), 0.96 (m, 2H), 0.029 (s, 9H); $^{13}$C NMR (100 MHz, CDCl$_3$) δ 147.9, 138.2, 128.7, 128.1, 108.1, 95.4, 76.3, 76.1, 73.7, 71.7, 71.6, 65.8, 18.3, −1.21; IR (KBr) 3468, 2952, 2892, 1651, 1250, 1028, 837 cm$^{-1}$; HRMS (ESI) [M+NH$_4^+$] Calcd. for $C_{19}H_{34}O_5N_1Si_1$ 384.22008, found 384.22010.

The glycal alcohol H (800 mg, 2.2 mmol) was dissolved in THF (1.0 M, 2.2 mL). Then DMF (0.10 mL) was added as a co-solvent. The solution was cooled to 0° C. NaH (60% in mineral oil, 96 mg, 2.4 mmol) was added to the solution all at once and stirred for 20 minutes. Then BnBr (0.39 mL, 3.3 mmol) was added to the solution all at once, followed by the addition of TBAI (41 mg, 0.11 mmol). The reaction was allowed to warm to r.t. and stirred overnight. After diluting with Et$_2$O (20 mL), a saturated solution of NH$_4$Cl (10 mL) was slowly added to quench the reaction. The aqueous layer was then extracted with EtOAc (2×10 mL). The organic extracts were combined and dried with MgSO$_4$. After filtration and evaporation of the volatiles under reduced pressure, chromatography (20:1→9:1 hexanes:EtOAc) gave dibenzyl ether 18 as a colorless oil (700 mg, 70%).

$[α]_D^{23}$=−43.4 (c 1.30, CHCl$_3$); $^1$H NMR (400 MHz, CDCl$_3$) δ 7.33 (m, 10H), 6.30 (dd, J=1.2, 7.6 Hz, 1H), 4.82 (m, 2H), 4.74 (m, 3H), 4.65 (s, 2H), 4.27 (m, 1H), 4.18 (m, 2H), 3.84 (m, 1H), 3.72 (m, 2H), 3.62 (m, 1H), 0.939 (m, 2H), 0.013 (s, 9H); $^{13}$C NMR (100 MHz, CDCl$_3$) δ 146.7, 138.8, 138.7, 128.6, 127.9, 127.9, 127.8, 127.7, 106.9, 94.8, 81.7, 75.3, 74.4, 73.4, 72.3, 69.7, 65.6, 18.3, −1.22; IR (KBr) 3033, 2951, 2889, 1651, 1454, 1249, 1029, 836, 738, 697 cm$^{-1}$; HRMS (ESI) [M+Na$^+$] Calcd. for $C_{26}H_{36}O_5Na_1Si_1$ 479.22242, found 479.22230.

5. Synthesis of Methyl Glycoside 20

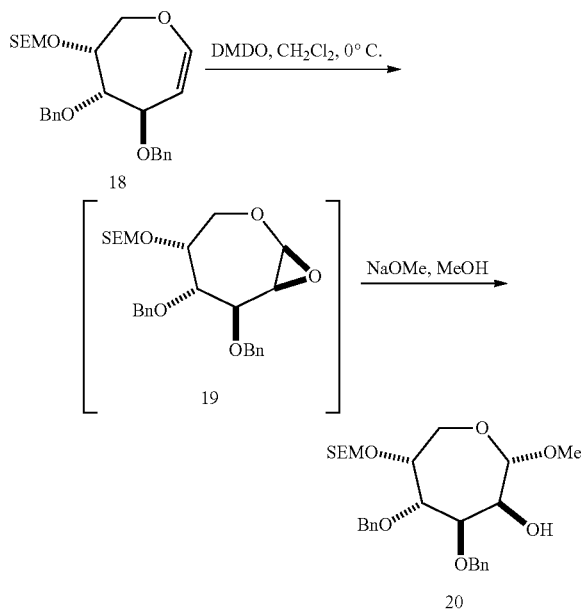

6. Preparation of D-Mannoseptanoside Acceptor Synthon 21

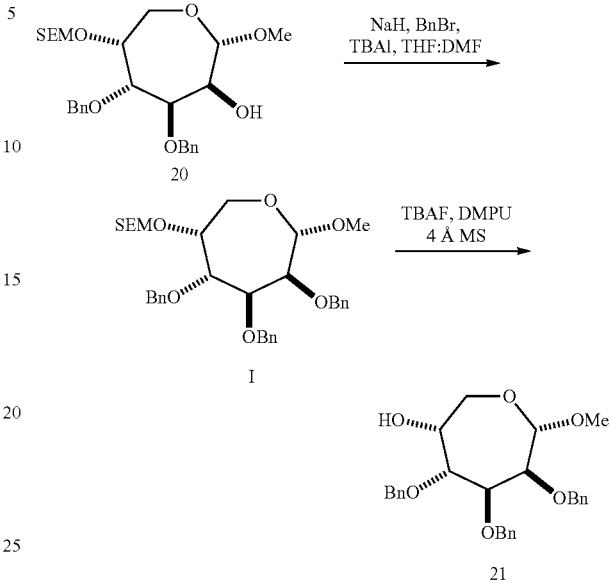

Glycal 18 (200 mg, 0.44 mmol) was dissolved in $CH_2Cl_2$ (0.10 M, 4.4 mL) and cooled to 0° C. A freshly prepared solution of DMDO (13 mL, 1.3 mmol) was then added to the solution. After 30 minutes, the volatiles were evaporated under reduced pressure with a rotary evaporator, and placed on a high vacuum for 10 minutes to provide epoxide 19 as an oil. Epoxide intermediate 19 was dissolved in MeOH (0.10 M, 4.4 mL), and then NaOMe (0.50 M solution in MeOH, 4.4 mL, 2.2 mmol) was added all at once. The reaction was stirred at r.t. overnight. The reaction was then diluted with $CH_2Cl_2$ (20 mL) and quenched by the addition of a saturated solution of $NH_4Cl$ (20 mL). The aqueous layer was extracted with EtOAc (1×20 mL). The organic extracts were combined and dried with $MgSO_4$. After filtration and evaporation of the volatiles under reduced pressure, chromatography (4:1→2:1 hexanes:EtOAc) gave methyl glycoside alcohol 20 as a colorless oil (160 mg, 72%).

$[\alpha]_D^{23}$=+18.3 (c 1.10, $CHCl_3$); $^1H$ NMR (400 MHz, $CDCl_3$) δ 7.31 (m, 10H), 4.64-4.74 (m, 5H), 4.51 (m, 2H), 4.21 (m, 1H), 4.10 (m, 1H), 4.00 (dd, J=9.2, 12.8 Hz, 1H), 3.88 (dd, J=2.0, 6.0 Hz, 1H), 3.82 (m, 1H), 3.62 (m, 3H), 3.42 (s, 3H), 2.14 (d, J=5.2 Hz, 1H), 0.934 (m, 2H), 0.018 (s, 9H); $^{13}C$ NMR (100 MHz, $CDCl_3$) δ 138.5, 128.7, 128.5, 127.9, 127.9, 127.8, 103.7, 94.3, 79.6, 76.8, 75.5, 74.2, 73.6, 72.8, 65.5, 62.3, 55.6, 18.3, −1.19; IR (KBr) 3460, 2953, 2895, 1454, 1248, 1093, 1028, 835, 698 cm$^{-1}$; HRMS (ESI) [M+NH$_4^+$] Calcd. for $C_{27}H_{44}O_7N_1Si_1$ 522.28816, found 522.28806.

Methyl glycoside alcohol 20 (160 mg, 0.32 mmol) was dissolved in THF (0.32 M, 1.0 mL). Then DMF (0.10 mL) was added as a co-solvent. The solution was cooled to 0° C., and NaH (60% dispersion in mineral oil, 19 mg, 0.48 mmol) was added all at once and stirred for 20 minutes. BnBr (0.060 mL, 0.48 mmol) was then added all at once, followed by the addition of TBAI (10 mg). The reaction was allowed to warm to r.t. and stirred overnight. After diluting with $Et_2O$ (20 mL), a saturated solution of $NH_4Cl$ (10 mL) was slowly added to quench the reaction. The aqueous layer was extracted with EtOAc (2×10 mL). The organic extracts were combined and dried with $MgSO_4$. After filtration and evaporation of the volatiles under reduced pressure, chromatography (20:1→4:1 hexanes:EtOAc) gave benzyl ether I as a colorless oil (160 mg, 84%).

$[\alpha]_D^{23}$=+6.8 (c 0.53, $CHCl_3$); $^1H$ NMR (400 MHz, $CDCl_3$) δ 7.15-7.35 (m, 15H), 4.77 (d, J=12.8 Hz, 1H), 4.56-4.69 (m, 6H), 4.43 (d, J=12.0 Hz, 1H), 4.36 (d, J=12.0 Hz, 1H), 4.02 (m, 3H), 3.83 (d, J=6.0 Hz, 1H), 3.72 (m, 1H), 3.61 (m, 2H), 3.49 (m, 1H), 3.43 (s, 3H), 0.940 (m, 2H), 0.020 (s, 9H); $^{13}C$ NMR (100 MHz, $CDCl_3$) δ 138.9, 138.7, 128.5, 128.5, 128.0, 127.9, 127.9, 127.8, 127.7, 103.7, 94.1, 80.1, 78.3, 76.2, 75.6, 73.7, 73.3, 65.5, 60.4, 55.4, 18.3, −1.16; IR (KBr) 3031, 2936, 1454, 1249, 1059, 837, 697 cm$^{-1}$; HRMS (ESI) [M+NH$_4^+$] Calcd. for $C_{34}H_{50}O_7N_1Si_1$ 612.33511, found 612.33490.

SEM-protected I (270 mg, 0.52 mmol) was dissolved in DMPU (0.50 M, 1.0 mL) and freshly activated 4 Å MS (750 mg, powdered) were added. Then TBAF (1.0 M in THF, 1.6 mL, 1.6 mmol) was added all at once. The reaction was stirred for 3 hours at r.t. Then the reaction was diluted with EtOAc (100 mL) and quenched by the addition of $H_2O$ (50 mL). The aqueous layer was extracted with EtOAc (2×50 mL). The organic layers were combined and dried with $MgSO_4$. After filtration and evaporation of the volatiles under reduced pressure, chromatography (4:1→2:1 hexanes:EtOAc) afforded methyl glycoside alcohol 21 as a colorless oil (190 mg, 79%).

$[\alpha]_D^{23}$=−8.9 (c 0.50, $CHCl_3$); $^1H$ NMR (400 MHz, $CDCl_3$) δ 7.25-7.34 (m, 12H), 7.07 (m, 2H), 4.81 (d, J=12.4 Hz, 1H), 4.69 (d, J=6.8 Hz, 1H), 4.64 (d, J=11.6 Hz, 1H), 4.43 (d, J=12.0 Hz, 1H), 4.29 (d, J=11.6 Hz, 1H), 4.20 (d, J=11.6 Hz, 1H), 3.99 (m, 1H), 3.92 (dd, J=6.0, 18.4 Hz, 1H), 3.73 (t, J=12.4 Hz, 1H), 3.67 (t, J=4.4 Hz, 1H), 3.41 (s, 3H), 2.29 (d, J=10.8 Hz, 1H); $^{13}$C NMR (100 MHz, CDCl$_3$) δ 138.8, 138.5, 137.5, 128.8, 128.6, 128.6, 128.4, 128.2, 128.2, 127.9, 127.8, 103.6, 79.5, 77.9, 77.5, 73.7, 73.4, 69.2, 62.2, 55.4; IR (KBr) 3460, 2927, 1454, 1066, 739, 698 cm$^{-1}$; HRMS (ESI) [M+NH$_4^+$] Calcd. for C$_{28}$H$_{36}$O$_6$N$_1$ 482.25371, found 482.25372.

7. Synthesis of Thioglycoside 22

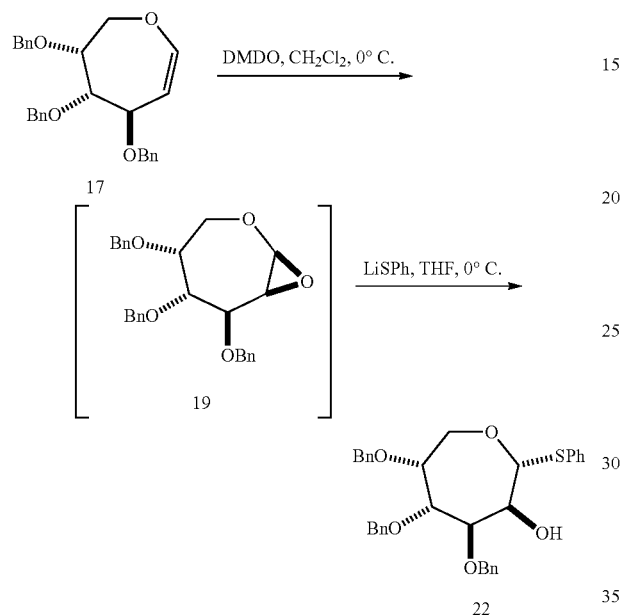

8. Synthesis of Thioglycoside 23

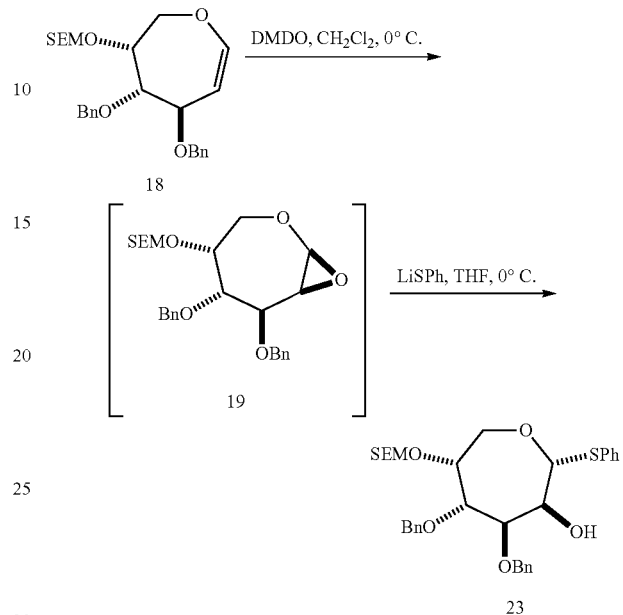

Glycal 17 (310 mg, 0.74 mmol) was dissolved in CH$_2$Cl$_2$ (0.10 M, 7.0 mL), and the solution was then cooled to 0° C. Then DMDO (15 mL, 1.5 mmol) was slowly added, and the reaction was stirred for 30 minutes at 0° C. Then the volatiles were evaporated under reduced pressure and the crude epoxide 19 was used directly in the next step. In a separate flask, thiophenol (0.70 mL, 7.4 mmol) was dissolved in THF (0.10 M, 7.0 mL), and the solution was cooled to 0° C. n-BuLi (2.5 M solution in hexanes, 2.9 mL, 7.3 mmol) was added dropwise and subsequently stirred for 10 minutes. Then the crude epoxide 19 was dissolved in THF (2.0 mL) and slowly added to the freshly prepared lithium thiophenoxide solution at 0° C. After 30 minutes, the reaction was quenched by the addition of H$_2$O (20 mL). The aqueous layer was extracted with EtOAc (1×20 mL). The organic extracts were combined and dried with MgSO$_4$. After filtration and evaporation of the volatiles under reduced pressure, chromatography (9:1→4:1 hexanes:EtOAc) gave thioglycoside 22 as a pale yellow oil (240 mg, 59%).

[α]$_D^{23}$=+87.1 (c 0.50, CHCl$_3$); $^1$H NMR (400 MHz, CDCl$_3$) δ 7.54 (m, 2H), 7.30 (m, 16H), 7.21 (m, 2H), 5.18 (d, J=8.8 Hz, 1H), 4.73 (d, J=11.6 Hz, 1H), 4.66 (d, J=12.0 Hz, 1H), 4.58 (m, 3H), 4.49 (d, J=12.0 Hz, 1H), 4.32 (ddd, J=1.6, 5.2, 6.0 Hz, 1H), 4.14 (dd, J=9.2, 12.8 Hz, 1H), 3.96 (dd, J=1.6, 6.0 Hz, 1H), 3.90 (m, 1H), 3.82 (m, 1H), 3.65 (dd, J=3.2, 12.4 Hz, 1H), 2.25 (d, J=5.6 Hz, 1H); $^{13}$C NMR (100 MHz, CDCl$_3$) δ 138.5, 138.4, 138.4, 134.5, 132.1, 129.1, 128.7, 128.6, 128.1, 128.1, 127.9, 127.8, 127.6, 91.4, 80.3, 75.8, 74.4, 73.7, 72.1, 71.6, 62.2; IR (KBr) 3465, 3062, 3030, 2873, 1583, 1496, 1439, 1074, 739, 696 cm$^{-1}$; HRMS (ESI) [M+Na$^+$] Calcd. for C$_{33}$H$_{34}$O$_5$Na$_1$S$_1$ 565.20192, found 565.20178.

As described above, reaction of the glycal 18 (300 mg, 0.66 mmol) in CH$_2$Cl$_2$ (0.10 M, 6.6 mL) with DMDO (15 mL, 1.5 mmol) provided an epoxide 19 which was dissolved in THF (2.0 mL) and added to lithium thiophenoxide prepared from thiophenol (0.68 mL, 6.6 mmol) and n-BuLi (2.5 M solution in hexanes, 2.6 mL, 6.5 mmol) in THF (0.10 M, 6.6 mL), to provide thioglycoside 23 as a colorless oil (170 mg, 45%). This procedure was repeated to give sufficient material for the subsequent glycosylations.

[α]$_D^{23}$=+78.9 (c 1.10, CHCl$_3$); $^1$H NMR (400 MHz, CDCl$_3$) δ 7.53 (m, 2H), 7.31 (m, 13H), 5.18 (d, J=9.2 Hz, 1H), 4.67 (m, 5H), 4.55 (d, J=12.0 Hz, 1H), 4.29 (ddd, J=2.0, 5.6, 9.2, 1H), 4.13 (m, 2H), 3.98 (dd, J=2.0, 6.0, 1H), 3.85 (m, 1H), 3.63 (m, 4H), 2.29 (d, J=5.2 Hz, 1H), 0.930 (t, J=8.8 Hz, 2H), 0.018 (s, 9H); $^{13}$C NMR (100 MHz, CDCl$_3$) δ 138.4, 138.3, 134.5, 129.1, 128.7, 128.6, 128.1, 128.0, 127.6, 94.5, 91.2, 80.2, 75.4, 74.4, 73.6, 71.6, 65.6, 63.4, 18.3, −1.17 18.3; IR (KBr) 3458, 3062, 3030, 2951, 2360, 1585, 1454, 1248, 1072, 918, 858, 740, 696 cm$^{-1}$; HRMS (ESI) [M+NH$_4^+$] Calcd. for C$_{32}$H$_{46}$O$_6$N$_1$S$_1$Si$_1$ 600.28097, found 600.28102.

9. Preparation of D-Mannoseptanoside Donor Synthon 24

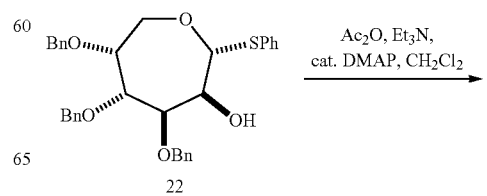

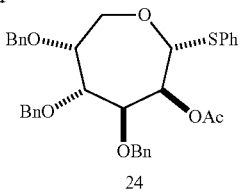

Thioglycoside 22 (240 mg, 0.56 mmol) was dissolved in $CH_2Cl_2$ (0.10 M, 5.6 mL). Pyridine (0.20 mL, 1.1 mmol) was added, followed by DMAP (10 mg) and acetic anhydride (0.10 mL, 1.1 mmol). The reaction was stirred for 30 minutes at r.t. The reaction was diluted with $CH_2Cl_2$ (20 mL) and quenched by the addition of $H_2O$ (10 mL). The aqueous layer was extracted with $CH_2Cl_2$ (1×10 mL). The organic extracts were combined and filtered with $MgSO_4$. After filtration and evaporation of the volatiles under reduced pressure, chromatography (9:1 hexanes:EtOAc) gave acetate 24 as a colorless oil (180 mg, 55%).

$[\alpha]_D^{23}$=+54.4 (c 1.00, $CHCl_3$); $^1H$ NMR (400 MHz, $CDCl_3$) δ 7.50 (m, 2H), 7.30 (m, 16H), 7.15 (m, 2H), 5.68 (d, J=9.2 Hz, 1H), 5.33 (d, J=9.6 Hz, 1H), 4.72 (d, J=12.0 Hz, 1H), 4.66 (d, J=12.8 Hz, 1H), 4.59 (d, J=12.0 Hz, 1H), 4.48 (m, 2H), 4.26 (dd, J=9.6, 12.4 Hz, 1H), 3.90 (m, 1H), 3.78 (m, 2H), 3.65 (dd, J=2.8, 12.4 Hz, 1H), 2.01 (s, 3H); $^{13}C$ NMR (100 MHz, $CDCl_3$) δ 169.7, 138.4, 138.3, 137.8, 135.0, 131.7, 129.0, 128.6, 128.5, 128.3, 128.2, 128.1, 127.9, 127.9, 127.8, 127.3, 87.3, 78.5, 74.2, 73.7, 73.4, 72.7, 71.9, 60.9; IR (KBr) 3062, 3030, 2893, 1745, 1454, 1369, 1228, 1076, 739, 698 $cm^{-1}$; HRMS (ESI) $[M+NH_4^+]$ Calcd. for $C_{35}H_{40}O_6N_1S_1$ 602.25709, found 602.25767.

10. Preparation of D-Mannoseptanoside Donor Synthon 25

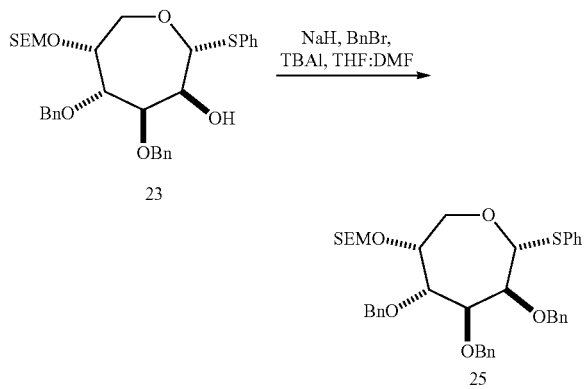

Thioglycoside alcohol 23 (520 mg, 0.89 mmol) was dissolved in THF (0.10 M, 8.9 mL). Then DMF (0.10 mL) was added as a co-solvent. The solution was cooled to 0° C., and NaH (60% dispersion in mineral oil, 52 mg, 0.48 mmol) was added all at once and stirred for 20 minutes. BnBr (0.15 mL, 1.3 mmol) was then added all at once, followed by the addition of TBAI (10 mg). The reaction was allowed to warm to r.t. and stirred overnight. After diluting with $Et_2O$ (20 mL), a saturated solution of $NH_4Cl$ (10 mL) was slowly added to quench the reaction. The aqueous layer was extracted with EtOAc (2×15 mL). The organic extracts were combined and dried with $MgSO_4$. After filtration and evaporation of the volatiles under reduced pressure, chromatography (20:1→4:1 hexanes:EtOAc) gave 25 as a colorless oil (480 mg, 80%).

$[\alpha]_D^{23}$=+55.4 (c 0.60, $CHCl_3$); $^1H$ NMR (400 MHz, $CDCl_3$) δ 7.53 (m, 2H), 7.29 (m, 18H), 5.38 (d, J=8.8 Hz, 1H), 4.75 (d, J=12.4 Hz, 1H), 4.64 (m, 5H), 4.41 (dd, J=8.0, 12.0 Hz, 1H), 4.13 (m, 3H), 3.88 (d, J=6.0, 1H), 3.77 (m, 1H), 3.61 (m, 3H), 0.930 (dd, J=7.2, 10.0 Hz, 2H), 0.031 (s, 9H); $^{13}C$ NMR (100 MHz, $CDCl_3$) δ 138.6, 138.5, 138.2, 135.4, 131.8, 128.9, 128.6, 128.5, 128.5, 128.1, 128.0, 127.9, 127.9, 127.8, 127.0, 94.2, 89.0, 80.2, 77.8, 76.4, 75.6, 74.0, 73.8, 73.6, 65.6, 61.6, 18.3, −1.16; IR (KBr) 3030, 2951, 2889, 1583, 1454, 1365, 1248, 1074, 837, 741, 698 $cm^{-1}$; HRMS (ESI) $[M+NH_4^+]$ Calcd. for $C_{39}H_{52}O_6N_1S_1Si_1$ 690.32792, found 690.32855.

The stereochemistry of mannoseptanoside 25 was confirmed by conversion into the known mannopyranoside J:

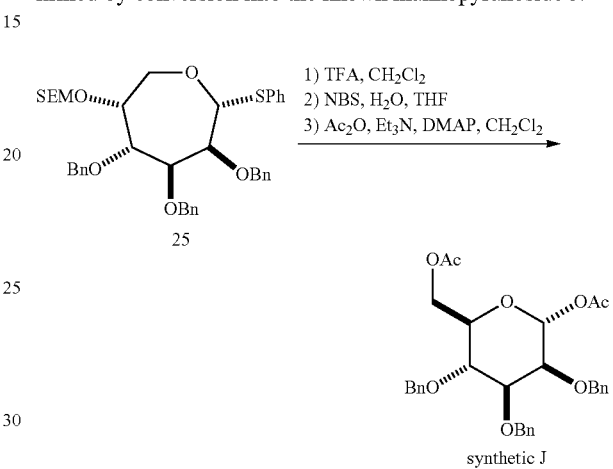

synthetic J

Thioglycoside 25 (130 mg, 0.19 mmol) was dissolved in $CH_2Cl_2$ (0.10 M, 2.0 mL). TFA (0.10 mL, 1.3 mmol) was added all at once. The reaction was stirred for 20 min. at r.t, at which point TLC indicated consumption of the starting material. A saturated solution of $NaHCO_3$ (2 mL) was added, and the mixture was stirred until elution of $CO_2$ stopped. The aqueous layer was then extracted with $Et_2O$ (3×2 mL). The combined organic layers were dried with $MgSO_4$ and filtered. After removal of the volatiles under reduced pressure, the crude material was dissolved in a mixture of $THF:H_2O$ (1:1, 0.10 M, 2.0 mL) with vigorous stirring. and NBS (21 mg, 0.12 mmol) was added all at once. The solution immediately turned orange-brown in color. After 5 minutes, reaction mixture was colorless, and TLC indicated consumption of the starting material. The reaction was diluted with $H_2O$ (2 mL) and EtOAc (2 mL). After the layers were separated, the aqueous layer was extracted with EtOAc (1×2 mL). The organic extracts were combined and dried with $MgSO_4$. After filtration, the volatiles were removed under reduced pressure. The crude material was then dissolved in $CH_2Cl_2$ (1.0 mL). $Et_3N$ (0.04 mL, 0.29 mmol and $Ac_2O$ (0.03 mL, 0.29 mmol) were sequentially added to the reaction mixture. DMAP (1 mg) was then added. After 10 minutes of stirring, TLC indicated the consumption of the starting material. The reaction was diluted with $CH_2Cl_2$ (2 mL) and quenched by the addition of a saturated solution of $NH_4Cl$ (2 mL). After separation of the layers, the aqueous layer was extracted with $CH_2Cl_2$ (2×2 mL). The organic extracts were combined and dried with $MgSO_4$. After filtration, the volatiles were removed under reduced pressure. The crude material was loaded onto a prep TLC plate. The plate was developed using 1:1 hexanes:EtOAc. Synthetic J, α-1,6-diacetyl-2,3,4-tri-O-benzyl-D-mannopyranose, was isolated as a white solid (21 mg, 21%), for spectroscopic comparison with literature spectra for α-1, 6-diacetyl-2,3,4-tri-O-benzyl-D-mannopyranose (J), as well as α- and β-anomers of 1,6-diacetyl-2,3,4-tri-O-benzyl-D-glucopyranose (K and L).

Example 3

C. Synthesis and Crystal Structure of Disaccharide 26

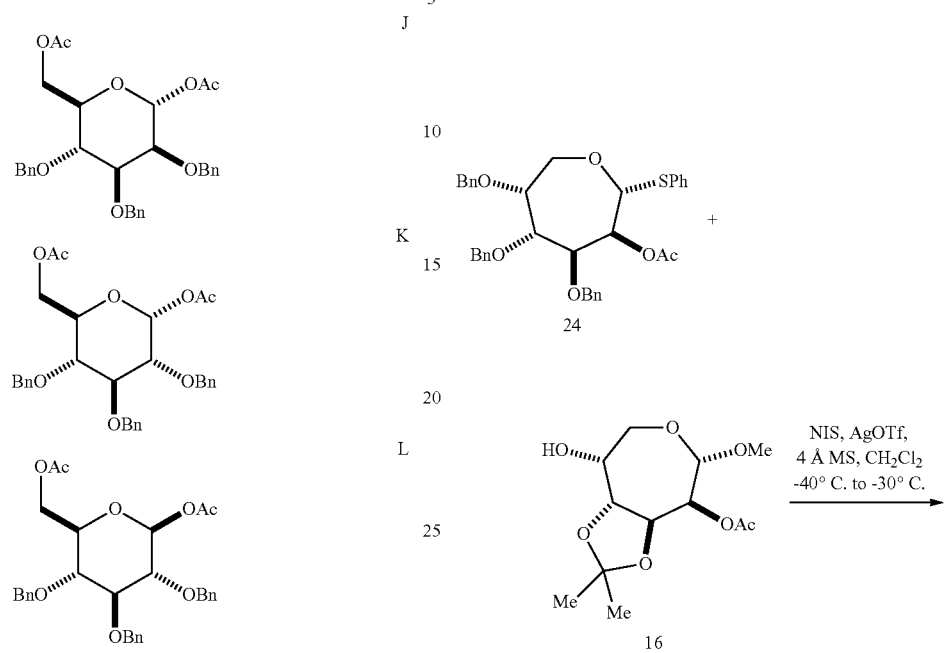

TABLE 4

| | Spectroscopic comparison of Synthetic J with literature spectra for J, K, and L | | | |
|---|---|---|---|---|
| | Synthetic J | J (ref. 2) | K (ref. 3) | L (ref. 3) |
| $[\alpha]_D^{23}$ | +29.5 (c 1.05, CHCl$_3$) | +31.3 (c 1.0, CHCl$_3$) | +58.2 (c 0.89, CHCl$_3$) | +25.3 (c 0.225, CHCl$_3$) |
| H | (ppm) | (ppm) | (ppm) | (ppm) |
| 1 | 6.19 (d, J = 1.6 Hz, 1H) | 6.19 (d, J = 2.0 Hz, 1H) | 6.25 (d, J = 3.6 Hz, 1H) | 5.85 (d, J = 8.1 Hz, 1H) |
| 2 | 3.75 (dd, J = 2.4 Hz, 1H) | 3.75 (dd, J = 2.9 Hz, 1H) | 3.60 (dd, J = 3.6, 9.5 Hz, 1H) | 3.50 (dd, J = 8.1, 9.0 Hz, 1H) |
| 3 | 3.88 (m, 2H) | 3.88 (m, 2H) | 3.90 (dd, J = 9.0, 9.5 Hz, 1H) | 3.68 (dd, J = 8.8, 9.0 Hz, 1H) |
| 4 | 3.99 (a-t, J = 9.6 Hz, 1H) | 3.99 (a-t, J = 9.5 Hz, 1H) | 3.50 (dd, J = 9.0, 10.0 Hz, 1H) | 3.49 (dd, J = 8.8, 9.8 Hz, 1H) |
| 5 | 3.88 (m, 2H) | 3.88 (m, 2H) | 3.85 (ddd, J = 2.4, 3.9, 10.0 Hz, 1H) | 3.58 (ddd, J = 2.2, 4.4, 9.8 Hz, 1H) |
| 6 | 4.33 (m, 2H) | 4.33 (m, 2H) | 4.17 (dd, J = 2.4, 12.2 Hz, 1H) | 4.16 (dd, J = 4.4, 12.2 Hz, 1H) |
| 6' | 4.33 (m, 2H) | 4.33 (m, 2H) | 4.21 (dd, J = 3.9, 12.2 Hz, 1H) | 4.21 (dd, J = 2.2, 12.2 Hz, 1H) |
| CH$_2$Ph | 4.61 (m, 3H) | 4.60 (m, 3H) | 4.50 (d, J = 11.0 Hz, 1H) | 4.49 (d, J = 10.8 Hz, 1H) |
| CH$_2$Ph | | | 4.57 (d, J = 11.3 Hz, 1H) | 4.68 (d, J = 11.2 Hz, 1H) |
| CH$_2$Ph | | | 4.64 (d, J = 11.3 Hz, 1H) | 4.71 (d, J = 11.2 Hz, 1H) |
| CH$_2$Ph | 4.73 (d, J = 12.4 Hz, 1H) | 4.73 (d, J = 12.1 Hz, 1H) | 4.76 (d, J = 10.7 Hz, 1H) | 4.75 (d, J = 10.7 Hz, 1H) |
| CH$_2$Ph | 4.78 (d, J = 12.4 Hz, 1H) | 4.78 (d, J = 12.1 Hz, 1H) | 4.82 (d, J = 10.7 Hz, 1H) | 4.78 (d, J = 10.7 Hz, 1H) |
| CH$_2$Ph | 4.96 (d, J = 10.4 Hz, 1H) | 4.96 (d, J = 10.6 Hz, 1H) | 4.92 (d, J = 11.0 Hz, 1H) | 4.85 (d, J = 10.8 Hz, 1H) |
| Aryl | 7.31-7.42 (m, 15H) | 7.29-7.42 (m, 15H) | 7.19-7.29 (m, 15H) | 7.17-7.28 (m, 15H) |
| MeC=O | 2.04 (s, 3H) | 2.04 (s, 3H) | 1.96 (s, 3H) | 1.96 (s, 3H) |
| MeC=O | 2.07 (s, 3H) | 2.07 (s, 3H) | 2.08 (s, 3H) | 1.98 (s, 3H) |

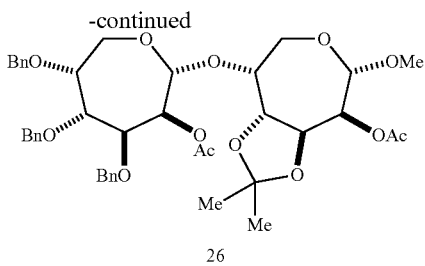

26

Thioglycoside 24 (160 mg, 0.27 mmol) and methyl glycoside 16 (85 mg, 0.30 mmol) were dissolved in $CH_2Cl_2$ (0.10 M, 2.7 mL). 4 Å MS (400 mg, powdered) were then added to the solution. The solution was cooled to −40° C. Then NIS (76 mg, 0.34 mmol) and AgOTf (21 mg, 0.08 mmol) were simultaneously added to the solution. The reaction was allowed to warm to −30° C., at which point the reaction became magenta in color. Upon the color change, TLC indicated the completion of the reaction. The reaction was quenched by the addition of $Et_3N$ (1.0 mL), which caused an immediate color change to yellow. The mixture was filtered through celite, and the volatiles were evaporated under reduced pressure. Chromatography (4:1 hexanes:EtOAc) gave disaccharide 26 as white crystalline needles (130 mg, 63%). mp 76-79° C.; $[\alpha]_D^{23}$=+44.6 (c 2.50, $CHCl_3$); $^1H$ NMR (400 MHz, $CDCl_3$) δ 7.32 (m, 13H), 7.16 (m, 2H), 5.58 (d, J=7.6 Hz, 1H), 5.42 (t, J=4.8 Hz, 1H), 5.25 (d, J=7.2 Hz, 1H), 4.72 (d, J=11.6 Hz, 1H), 4.66 (d, J=12.4 Hz, 1H), 4.56 (d, J=12.0 Hz, 1H), 4.49 (d, J=12.0 Hz, 1H), 4.46 (m, 1H), 4.31 (m, 2H), 4.22 (dd, J=2.4, 9.2 Hz, 1H), 4.17 (dd, J=2.0, 12.0 Hz, 1H), 4.12 (dd, J=3.2, 13.6 Hz, 1H), 3.82 (m, 3H), 3.69 (dd, J=3.2, 13.6 Hz, 1H), 3.56 (m, 1H), 3.38 (s, 3H), 2.11 (s, 3H), 1.96 (s, 3H) 1.45 (s, 3H), 1.34 (s, 3H); $^{13}C$ NMR (100 MHz, $CDCl_3$) δ 169.9, 169.7, 138.4, 138.4, 137.9, 128.6, 128.5, 128.3, 128.1, 128.1, 127.9, 127.8, 109.8, 107.9, 100.1, 77.1, 76.8, 74.3, 74.2, 73.5, 73.2, 72.9, 71.8, 71.4, 71.4, 70.7, 60.2, 56.3, 26.9, 26.5, 21.4, 21.2; IR (KBr) 2926, 2856, 1747, 1371, 1232, 1086, 1028, 739, 698 $cm^{-1}$; HRMS (ESI) [M+$NH_4^+$] Calcd. for $C_{41}H_{54}O_{13}N_1$ 768.35897, found 768.35737.

Slow recrystallization of compound 26 from a mixture of hexanes and ether provided crystals suitable for structural characterization by X-ray crystallography, resulting in the thermal ellipsoid shown in FIG. 1:

TABLE 5

Crystal data and structure refinement for compound 26

| | |
|---|---|
| Identification code | B103329 |
| Empirical formula | C41.25 H50 O13.13 |
| Formula weight | 755.81 |
| Temperature | 173(2) K |
| Wavelength | 1.54178 Å |
| Crystal system | Monoclinic |
| Space group | C2 |
| Unit cell dimensions | a = 39.015(3) Å  α = 90°. |
| | b = 9.2033(9) Å  β = 101.259(6)°. |
| | c = 23.6697(19) Å  γ = 90°. |
| Volume | 8335.4(13) Å$^3$ |
| Z | 8 |
| Density (calculated) | 1.205 Mg/m$^3$ |
| Absorption coefficient | 0.742 mm$^{-1}$ |
| F(000) | 3220 |
| Crystal size | 0.66 × 0.06 × 0.03 mm$^3$ |
| Theta range for data collection | 2.31 to 66.10°. |
| Index ranges | −44 <= h <= 45, −10 <= k <= 6, −26 <= l <= 23 |
| Reflections collected | 13811 |
| Independent reflections | 8386 [R(int) = 0.0794] |

TABLE 5-continued

Crystal data and structure refinement for compound 26

| | |
|---|---|
| Completeness to theta = 66.10° | 82.9% |
| Absorption correction | Semi-empirical from equivalents |
| Max. and min. transmission | 0.9781 and 0.6402 |
| Refinement method | Full-matrix least-squares on F2 |
| Data/restraints/parameters | 8386/1/984 |
| Goodness-of-fit on F2 | 1.114 |
| Final R indices [I > 2sigma(I)] | R1 = 0.0935, wR2 = 0.2368 |
| R indices (all data) | R1 = 0.1392, wR2 = 0.2752 |
| Absolute structure parameter | −0.2(4) |
| Extinction coefficient | 0.00047(8) |
| Largest diff. peak and hole | 0.667 and −0.364 e · Å$^{-3}$ |

TABLE 6

Atomic coordinates (×10$^4$) and equivalent isotropic displacement parameters (Å$^2$ × 10$^3$) for compound 26. U(eq): One third of the trace of the orthogonalized U$^{ij}$ tensor

| | x | y | z | U(eq) |
|---|---|---|---|---|
| C(1) | 7152(2) | 6024(10) | 9105(4) | 43(2) |
| C(2) | 7410(2) | 7089(9) | 9468(4) | 38(2) |
| C(3) | 7255(2) | 8582(9) | 9531(3) | 36(2) |
| C(4) | 6921(2) | 8611(11) | 9782(3) | 43(2) |
| C(5) | 6607(2) | 7945(10) | 9372(4) | 43(2) |
| C(6) | 6577(2) | 6302(11) | 9360(4) | 48(2) |
| C(7) | 6237(2) | 4564(10) | 8689(4) | 43(2) |
| C(8) | 6205(2) | 4307(10) | 8057(4) | 41(2) |
| C(9) | 5595(2) | 4784(10) | 7631(3) | 42(2) |
| C(10) | 5400(2) | 5498(10) | 8056(4) | 41(2) |
| C(11) | 5626(2) | 5715(10) | 8637(3) | 44(2) |
| C(12) | 5873(2) | 4443(11) | 8847(3) | 43(2) |
| C(13) | 5561(2) | 4975(12) | 9557(4) | 57(3) |
| C(14) | 5606(3) | 5818(16) | 10102(4) | 73(3) |
| C(15) | 5323(2) | 3669(14) | 9547(5) | 62(3) |
| C(16) | 4797(2) | 5038(11) | 8130(5) | 54(2) |
| C(17) | 4545(3) | 3883(14) | 8218(5) | 65(3) |
| C(18) | 5527(3) | 4380(20) | 6626(4) | 87(5) |
| C(19) | 7987(2) | 7996(12) | 9428(4) | 50(2) |
| C(20) | 8258(2) | 7745(13) | 9070(4) | 55(2) |
| C(21) | 8603(3) | 7404(16) | 9307(8) | 100(5) |
| C(22) | 8834(3) | 7073(17) | 8842(7) | 87(4) |
| C(23) | 8714(5) | 7300(20) | 8302(8) | 103(5) |
| C(24) | 8394(5) | 7750(20) | 8093(7) | 102(5) |
| C(25) | 8154(4) | 7960(20) | 8454(5) | 93(4) |
| C(26) | 7212(3) | 10759(11) | 8953(4) | 57(3) |
| C(27) | 7135(2) | 11228(11) | 8328(4) | 48(2) |
| C(28) | 7396(4) | 11562(18) | 8019(7) | 101(5) |
| C(29) | 7302(5) | 11970(20) | 7423(7) | 118(6) |
| C(30) | 7003(5) | 12121(15) | 7161(5) | 87(4) |
| C(31) | 6710(4) | 11743(19) | 7473(6) | 98(5) |
| C(32) | 6796(3) | 11342(18) | 8042(5) | 82(4) |
| C(33) | 6925(4) | 8838(15) | 10813(5) | 83(4) |
| C(34) | 6753(4) | 8027(12) | 11234(4) | 52(2) |
| C(35) | 6778(4) | 8497(16) | 11779(5) | 92(4) |
| C(36) | 6614(5) | 7802(19) | 12172(5) | 98(5) |
| C(37) | 6426(4) | 6622(18) | 12017(6) | 88(4) |
| C(38) | 6388(3) | 6169(19) | 11483(5) | 89(5) |
| C(39) | 6542(3) | 6861(15) | 11084(4) | 66(3) |
| C(40) | 6154(3) | 9744(15) | 9364(5) | 64(3) |
| C(41) | 5810(3) | 9930(20) | 9551(6) | 99(5) |
| C(1B) | 3310(3) | 826(12) | 6626(4) | 54(2) |
| C(2B) | 3043(2) | 1754(10) | 6202(4) | 45(2) |
| C(3B) | 3168(2) | 3282(10) | 6121(3) | 40(2) |
| C(4B) | 3521(2) | 3369(10) | 5937(3) | 40(2) |
| C(5B) | 3823(2) | 2877(10) | 6424(4) | 41(2) |
| C(6B) | 3880(2) | 1239(11) | 6444(4) | 47(2) |
| C(7B) | 4238(2) | −414(10) | 7122(4) | 45(2) |
| C(8B) | 4260(2) | −655(11) | 7769(4) | 52(2) |
| C(9B) | 4853(2) | −207(11) | 8217(4) | 48(2) |
| C(10B) | 5068(2) | 485(9) | 7809(3) | 37(2) |
| C(11B) | 4839(2) | 729(10) | 7209(3) | 42(2) |
| C(12B) | 4591(2) | −524(10) | 6974(3) | 41(2) |
| C(13B) | 4901(3) | 55(14) | 6283(4) | 64(3) |
| C(14B) | 4837(4) | 1135(19) | 5760(5) | 91(4) |

TABLE 6-continued

Atomic coordinates (×10⁴) and equivalent isotropic displacement parameters (Å² × 10³) for compound 26. U(eq): One third of the trace of the orthogonalized $U^{ij}$ tensor

|  | x | y | z | U(eq) |
|---|---|---|---|---|
| C(15B) | 5147(4) | −1228(17) | 6227(7) | 100(5) |
| C(16B) | 4874(3) | −580(20) | 9186(5) | 109(6) |
| C(17B) | 5664(2) | 30(11) | 7741(4) | 49(2) |
| C(18B) | 5907(3) | −1172(11) | 7667(5) | 58(3) |
| C(19B) | 2473(3) | 787(17) | 6272(6) | 83(4) |
| C(20B) | 2174(2) | 1115(13) | 6594(6) | 110(6) |
| C(21B) | 1847(3) | 560(15) | 6351(7) | 169(10) |
| C(22B) | 1565(2) | 791(18) | 6618(9) | 222(18) |
| C(23B) | 1609(4) | 1580(20) | 7129(9) | 300(30) |
| C(24B) | 1936(5) | 2133(19) | 7372(7) | 320(30) |
| C(25B) | 2219(3) | 1902(17) | 7104(6) | 169(12) |
| C(26B) | 2908(3) | 5028(12) | 6683(4) | 55(3) |
| C(27B) | 2829(2) | 6115(11) | 6203(4) | 47(2) |
| C(28B) | 2486(3) | 6244(13) | 5869(4) | 60(3) |
| C(29B) | 2408(4) | 7238(14) | 5408(4) | 72(5) |
| C(30B) | 2670(4) | 8018(15) | 5253(5) | 90(5) |
| C(31B) | 3014(4) | 7937(14) | 5587(5) | 80(3) |
| C(32B) | 3084(3) | 6952(11) | 6049(4) | 61(3) |
| C(33B) | 3719(7) | 2960(30) | 5073(6) | 203(15) |
| C(34B) | 3736(4) | 1786(18) | 4627(6) | 91(4) |
| C(35B) | 3495(4) | 550(20) | 4552(6) | 104(5) |
| C(36B) | 3501(5) | −440(20) | 4091(8) | 118(6) |
| C(37B) | 3723(6) | −270(30) | 3702(8) | 140(8) |
| C(38B) | 3962(5) | 980(30) | 3754(8) | 140(8) |
| C(39B) | 3979(5) | 1920(30) | 4210(7) | 130(7) |
| C(40B) | 4234(3) | 4842(13) | 6569(4) | 59(3) |
| C(41B) | 4576(3) | 5330(17) | 6475(6) | 84(4) |
| C(1S) | 4189(10) | 7000(50) | 4987(16) | 56(9) |
| C(2S) | 3815(8) | 6120(40) | 4948(12) | 35(7) |
| O(1) | 6901(1) | 5539(7) | 9440(3) | 49(2) |
| O(2) | 6375(1) | 6000(7) | 8797(2) | 44(1) |
| O(3) | 5947(1) | 5282(7) | 7715(2) | 44(1) |
| O(4) | 5431(2) | 5226(9) | 7067(3) | 57(2) |
| O(5) | 5118(1) | 4461(7) | 8102(3) | 47(2) |
| O(6) | 4737(2) | 6294(10) | 8065(5) | 90(3) |
| O(7) | 5428(2) | 5921(8) | 9076(3) | 53(2) |
| O(8) | 5902(2) | 4546(8) | 9472(2) | 50(2) |
| O(9) | 7691(1) | 7106(7) | 9176(2) | 46(1) |
| O(10) | 7182(2) | 9218(7) | 8965(2) | 42(1) |
| O(11) | 6974(2) | 7893(8) | 10334(3) | 52(2) |
| O(12) | 6284(2) | 8391(8) | 9551(3) | 56(2) |
| O(13) | 6307(2) | 10568(10) | 9104(4) | 80(2) |
| O(1B) | 3580(2) | 384(7) | 6348(3) | 53(2) |
| O(2B) | 4085(2) | 1015(7) | 7007(2) | 49(2) |
| O(3B) | 4502(1) | 321(7) | 8102(2) | 44(1) |
| O(4B) | 5013(2) | 246(11) | 8772(2) | 72(2) |
| O(5B) | 5347(1) | −554(7) | 7776(2) | 45(1) |
| O(6B) | 5724(2) | 1263(8) | 7773(4) | 76(2) |
| O(7B) | 5060(2) | 875(8) | 6784(2) | 56(2) |
| O(8B) | 4573(2) | −426(8) | 6369(3) | 55(2) |
| O(9B) | 2724(2) | 1908(8) | 6423(3) | 58(2) |
| O(10B) | 3202(1) | 4119(7) | 6635(2) | 44(2) |
| O(11B) | 3506(2) | 2580(8) | 5416(2) | 55(2) |
| O(12B) | 4148(1) | 3487(7) | 6347(3) | 49(2) |
| O(13B) | 4036(2) | 5536(10) | 6800(4) | 80(2) |
| O(1S) | 4402(8) | 6080(40) | 4937(12) | 71(8) |

TABLE 7

Bond lengths [Å] and angles [°] for compound 26.

| C(1)—C(2) | 1.541(12) |
|---|---|
| C(2)—O(9) | 1.406(10) |
| C(2)—C(3) | 1.519(12) |
| C(3)—O(10) | 1.439(10) |
| C(3)—C(4) | 1.533(12) |
| C(4)—O(11) | 1.442(10) |
| C(4)—C(5) | 1.535(12) |
| C(5)—O(12) | 1.462(11) |
| C(5)—C(6) | 1.516(14) |
| C(6)—O(1) | 1.426(11) |

TABLE 7-continued

Bond lengths [Å] and angles [°] for compound 26.

| C(6)—O(2) | 1.436(10) |
|---|---|
| C(7)—O(2) | 1.431(11) |
| C(7)—C(8) | 1.495(12) |
| C(7)—C(12) | 1.541(13) |
| C(8)—O(3) | 1.468(10) |
| C(9)—O(3) | 1.422(10) |
| C(9)—O(4) | 1.422(10) |
| C(9)—C(10) | 1.525(12) |
| C(10)—O(5) | 1.476(11) |
| C(10)—C(11) | 1.495(11) |
| C(11)—O(7) | 1.424(10) |
| C(11)—C(12) | 1.535(13) |
| C(12)—O(8) | 1.465(10) |
| C(13)—O(8) | 1.440(12) |
| C(13)—O(7) | 1.446(12) |
| C(13)—C(14) | 1.487(15) |
| C(13)—C(15) | 1.514(16) |
| C(16)—O(6) | 1.183(14) |
| C(16)—O(5) | 1.375(12) |
| C(16)—C(17) | 1.489(15) |
| C(18)—O(4) | 1.409(15) |
| C(19)—O(9) | 1.447(11) |
| C(19)—C(20) | 1.494(13) |
| C(20)—C(21) | 1.389(15) |
| C(20)—C(25) | 1.450(16) |
| C(21)—C(22) | 1.58(2) |
| C(22)—C(23) | 1.290(18) |
| C(23)—C(24) | 1.32(2) |
| C(24)—C(25) | 1.40(2) |
| C(26)—O(10) | 1.424(12) |
| C(26)—C(27) | 1.514(13) |
| C(27)—C(32) | 1.366(14) |
| C(27)—C(28) | 1.401(19) |
| C(28)—C(29) | 1.44(2) |
| C(29)—C(30) | 1.22(2) |
| C(30)—C(31) | 1.52(2) |
| C(31)—C(32) | 1.374(17) |
| C(33)—O(11) | 1.471(14) |
| C(33)—C(34) | 1.503(15) |
| C(34)—C(35) | 1.346(14) |
| C(34)—C(39) | 1.357(16) |
| C(35)—C(36) | 1.385(19) |
| C(36)—C(37) | 1.32(2) |
| C(37)—C(38) | 1.313(18) |
| C(38)—C(39) | 1.369(16) |
| C(40)—O(13) | 1.206(15) |
| C(40)—O(12) | 1.385(15) |
| C(40)—C(41) | 1.500(18) |
| C(1B)—O(1B) | 1.407(12) |
| C(1B)—C(2B) | 1.554(13) |
| C(2B)—O(9B) | 1.448(11) |
| C(2B)—C(3B) | 1.514(13) |
| C(3B)—O(10B) | 1.423(10) |
| C(3B)—C(4B) | 1.525(12) |
| C(4B)—O(11B) | 1.422(11) |
| C(4B)—C(5B) | 1.546(11) |
| C(5B)—O(12B) | 1.431(11) |
| C(5B)—C(6B) | 1.523(13) |
| C(6B)—O(1B) | 1.391(11) |
| C(6B)—O(2B) | 1.429(10) |
| C(7B)—O(2B) | 1.447(11) |
| C(7B)—C(12B) | 1.492(13) |
| C(7B)—C(8B) | 1.534(13) |
| C(8B)—O(3B) | 1.425(11) |
| C(9B)—O(4B) | 1.405(10) |
| C(9B)—O(3B) | 1.426(10) |
| C(9B)—C(10B) | 1.536(13) |
| C(10B)—O(5B) | 1.461(10) |
| C(10B)—C(11B) | 1.539(11) |
| C(11B)—O(7B) | 1.455(10) |
| C(11B)—C(12B) | 1.537(12) |
| C(12B)—O(8B) | 1.423(10) |
| C(13B)—O(8B) | 1.409(14) |
| C(13B)—O(7B) | 1.440(12) |
| C(13B)—C(15B) | 1.541(19) |
| C(13B)—C(14B) | 1.569(18) |
| C(16B)—O(4B) | 1.427(17) |
| C(17B)—O(6B) | 1.159(13) |

TABLE 7-continued

Bond lengths [Å] and angles [°] for compound 26.

| | |
|---|---|
| C(17B)—O(5B) | 1.369(11) |
| C(17B)—C(18B) | 1.487(15) |
| C(19B)—O(9B) | 1.421(15) |
| C(19B)—C(20B) | 1.542(17) |
| C(20B)—C(21B) | 1.3900 |
| C(20B)—C(25B) | 1.3900 |
| C(21B)—C(22B) | 1.3900 |
| C(22B)—C(23B) | 1.3900 |
| C(23B)—C(24B) | 1.3900 |
| C(24B)—C(25B) | 1.3900 |
| C(26B)—O(10B) | 1.444(11) |
| C(26B)—C(27B) | 1.500(14) |
| C(27B)—C(32B) | 1.364(15) |
| C(27B)—C(28B) | 1.421(12) |
| C(28B)—C(29B) | 1.410(16) |
| C(29B)—C(30B) | 1.36(2) |
| C(30B)—C(31B) | 1.422(18) |
| C(31B)—C(32B) | 1.406(16) |
| C(33B)—O(11B) | 1.319(17) |
| C(33B)—C(34B) | 1.52(3) |
| C(34B)—C(35B) | 1.47(2) |
| C(34B)—C(39B) | 1.50(2) |
| C(35B)—C(36B) | 1.43(2) |
| C(36B)—C(37B) | 1.39(3) |
| C(37B)—C(38B) | 1.47(3) |
| C(38B)—C(39B) | 1.37(3) |
| C(40B)—O(13B) | 1.211(13) |
| C(40B)—O(12B) | 1.370(13) |
| C(40B)—C(41B) | 1.467(15) |
| C(1S)—O(1S) | 1.21(5) |
| C(1S)—C(2S) | 1.65(5) |
| O(1)—C(1)—C(2) | 109.1(7) |
| O(9)—C(2)—C(3) | 113.6(7) |
| O(9)—C(2)—C(1) | 102.7(6) |
| C(3)—C(2)—C(1) | 113.7(7) |
| O(10)—C(3)—C(2) | 106.7(6) |
| O(10)—C(3)—C(4) | 108.9(6) |
| C(2)—C(3)—C(4) | 115.9(7) |
| O(11)—C(4)—C(3) | 111.1(6) |
| O(11)—C(4)—C(5) | 110.2(7) |
| C(3)—C(4)—C(5) | 112.5(7) |
| O(12)—O(5)—C(6) | 102.6(7) |
| O(12)—C(5)—C(4) | 109.4(7) |
| C(6)—C(5)—C(4) | 117.4(7) |
| O(1)—C(6)—O(2) | 109.9(7) |
| O(1)—C(6)—C(5) | 115.2(7) |
| O(2)—C(6)—C(5) | 103.7(7) |
| O(2)—C(7)—C(8) | 106.3(7) |
| O(2)—C(7)—C(12) | 110.9(7) |
| C(8)—C(7)—C(12) | 109.3(6) |
| O(3)—C(8)—C(7) | 111.6(7) |
| O(3)—C(9)—O(4) | 106.6(6) |
| O(3)—C(9)—C(10) | 111.2(7) |
| O(4)—C(9)—C(10) | 107.7(7) |
| O(5)—C(10)—C(11) | 109.4(7) |
| O(5)—C(10)—C(9) | 104.3(7) |
| C(11)—C(10)—C(9) | 112.6(7) |
| O(7)—C(11)—C(10) | 112.5(7) |
| O(7)—C(11)—C(12) | 105.1(7) |
| C(10)—C(11)—C(12) | 114.5(7) |
| O(8)—C(12)—C(11) | 101.4(7) |
| O(8)—C(12)—C(7) | 110.2(6) |
| C(11)—C(12)—C(7) | 114.5(7) |
| O(8)—C(13)—O(7) | 104.7(7) |
| O(8)—C(13)—C(14) | 107.8(8) |
| O(7)—C(13)—C(14) | 109.4(10) |
| O(8)—C(13)—C(15) | 111.1(9) |
| O(7)—C(13)—C(15) | 110.0(8) |
| C(14)—C(13)—C(15) | 113.4(9) |
| O(6)—C(16)—O(5) | 122.0(9) |
| O(6)—C(16)—C(17) | 126.6(10) |
| O(5)—C(16)—C(17) | 111.3(9) |
| O(9)—C(19)—C(20) | 106.0(7) |
| C(21)—C(20)—C(25) | 119.6(11) |
| C(21)—C(20)—C(19) | 122.9(11) |
| C(25)—C(20)—C(19) | 117.4(9) |
| C(20)—C(21)—C(22) | 113.8(13) |
| C(23)—C(22)—C(21) | 120.7(12) |
| C(22)—C(23)—C(24) | 123.9(16) |
| C(23)—C(24)—C(25) | 120.8(16) |
| C(24)—C(25)—C(20) | 120.5(14) |
| O(10)—C(26)—C(27) | 107.6(7) |
| C(32)—C(27)—C(28) | 117.3(10) |
| C(32)—C(27)—C(26) | 119.6(9) |
| C(28)—C(27)—C(26) | 123.1(10) |
| C(27)—C(28)—C(29) | 119.8(14) |
| C(30)—C(29)—C(28) | 124.5(16) |
| C(29)—C(30)—C(31) | 117.6(13) |
| C(32)—C(31)—C(30) | 118.6(12) |
| C(27)—C(32)—C(31) | 122.1(12) |
| O(11)—C(33)—C(34) | 111.1(9) |
| C(35)—C(34)—C(39) | 115.5(10) |
| C(35)—C(34)—C(33) | 121.2(10) |
| C(39)—C(34)—C(33) | 123.1(9) |
| C(34)—C(35)—C(36) | 122.7(13) |
| C(37)—C(36)—C(35) | 119.8(11) |
| C(38)—C(37)—C(36) | 118.7(12) |
| C(37)—C(38)—C(39) | 122.3(13) |
| C(34)—C(39)—C(38) | 120.8(10) |
| O(13)—C(40)—O(12) | 122.6(9) |
| O(13)—C(40)—C(41) | 129.6(13) |
| O(12)—C(40)—C(41) | 107.8(13) |
| O(1B)—C(1B)—C(2B) | 109.0(7) |
| O(9B)—C(2B)—C(3B) | 106.0(7) |
| O(9B)—C(2B)—C(1B) | 109.6(7) |
| C(3B)—C(2B)—C(1B) | 113.6(7) |
| O(10B)—C(3B)—C(2B) | 111.9(7) |
| O(10B)—C(3B)—C(4B) | 106.1(7) |
| C(2B)—C(3B)—C(4B) | 114.6(7) |
| O(11B)—C(4B)—C(3B) | 109.6(7) |
| O(11B)—C(4B)—C(5B) | 113.2(7) |
| C(3B)—C(4B)—C(5B) | 111.7(7) |
| O(12B)—C(5B)—C(6B) | 105.4(7) |
| O(12B)—C(5B)—C(4B) | 110.9(7) |
| C(6B)—C(5B)—C(4B) | 113.5(7) |
| O(1B)—C(6B)—O(2B) | 111.9(8) |
| O(1B)—C(6B)—C(5B) | 116.3(7) |
| O(2B)—C(6B)—C(5B) | 103.0(7) |
| O(2B)—C(7B)—C(12B) | 112.4(7) |
| O(2B)—C(7B)—C(8B) | 105.1(7) |
| C(12B)—C(7B)—C(8B) | 110.4(7) |
| O(3B)—C(8B)—C(7B) | 111.4(8) |
| O(4B)—C(9B)—O(3B) | 108.2(7) |
| O(4B)—C(9B)—C(10B) | 105.5(7) |
| O(3B)—C(9B)—C(10B) | 111.1(7) |
| O(5B)—C(10B)—C(9B) | 105.4(7) |
| O(5B)—C(10B)—C(11B) | 110.5(6) |
| C(9B)—C(10B)—C(11B) | 110.5(6) |
| O(7B)—C(11B)—C(12B) | 103.6(7) |
| O(7B)—C(11B)—C(10B) | 109.6(7) |
| C(12B)—C(11B)—C(10B) | 115.7(7) |
| O(8B)—C(12B)—C(7B) | 111.3(6) |
| O(8B)—C(12B)—C(11B) | 102.8(7) |
| C(7B)—C(12B)—C(11B) | 114.2(7) |
| O(8B)—C(13B)—O(7B) | 107.6(8) |
| O(8B)—C(13B)—C(15B) | 111.7(11) |
| O(7B)—C(13B)—C(15B) | 107.3(9) |
| O(8B)—C(13B)—C(14B) | 107.7(9) |
| O(7B)—C(13B)—C(14B) | 107.2(11) |
| C(15B)—C(13B)—C(14B) | 115.1(11) |
| O(6B)—C(17B)—O(5B) | 123.6(9) |
| O(6B)—C(17B)—C(18B) | 127.7(10) |
| O(5B)—C(17B)—C(18B) | 108.6(9) |
| O(9B)—C(19B)—C(20B) | 106.5(11) |
| C(21B)—C(20B)—C(25B) | 120.0 |
| C(21B)—C(20B)—C(19B) | 116.4(9) |
| C(25B)—C(20B)—C(19B) | 123.6(9) |
| C(20B)—C(21B)—C(22B) | 120.0 |
| C(23B)—C(22B)—C(21B) | 120.0 |
| C(22B)—C(23B)—C(24B) | 120.0 |
| C(23B)—C(24B)—C(25B) | 120.0 |
| C(24B)—C(25B)—C(20B) | 120.0 |
| O(10B)—C(26B)—C(27B) | 112.0(8) |
| C(32B)—C(27B)—C(28B) | 117.6(9) |
| C(32B)—C(27B)—C(26B) | 121.7(8) |
| C(28B)—C(27B)—C(26B) | 120.6(10) |

TABLE 7-continued

Bond lengths [Å] and angles [°] for compound 26.

| | |
|---|---|
| C(29B)—C(28B)—C(27B) | 121.4(11) |
| C(30B)—C(29B)—C(28B) | 119.5(11) |
| C(29B)—C(30B)—C(31B) | 120.1(12) |
| C(32B)—C(31B)—C(30B) | 119.0(13) |
| C(27B)—C(32B)—C(31B) | 122.1(10) |
| O(11B)—C(33B)—C(34B) | 110.7(14) |
| C(35B)—C(34B)—C(39B) | 117.1(15) |
| C(35B)—C(34B)—C(33B) | 121.5(13) |
| C(39B)—C(34B)—C(33B) | 121.1(15) |
| C(36B)—C(35B)—C(34B) | 118.9(15) |
| C(37B)—C(36B)—C(35B) | 122.7(18) |
| C(36B)—C(37B)—C(38B) | 119.9(18) |
| C(39B)—C(38B)—C(37B) | 119.3(17) |
| C(38B)—C(39B)—C(34B) | 121.8(19) |
| O(13B)—C(40B)—O(12B) | 121.5(9) |
| O(13B)—C(40B)—C(41B) | 126.0(11) |
| O(12B)—C(40B)—C(41B) | 112.5(10) |
| O(1S)—C(1S)—C(2S) | 106(4) |
| C(6)—O(1)—C(1) | 116.9(7) |
| C(7)—O(2)—C(6) | 117.7(7) |
| C(9)—O(3)—C(8) | 114.8(6) |
| C(18)—O(4)—C(9) | 113.7(9) |
| C(16)—O(5)—C(10) | 117.0(7) |
| C(11)—O(7)—C(13) | 109.5(7) |
| C(13)—O(8)—C(12) | 105.5(6) |
| C(2)—O(9)—C(19) | 116.2(6) |
| C(26)—O(10)—C(3) | 115.0(6) |
| C(4)—O(11)—C(33) | 114.2(8) |
| C(40)—O(12)—C(5) | 116.4(8) |
| C(6B)—O(1B)—C(1B) | 116.2(7) |
| C(6B)—O(2B)—C(7B) | 116.2(7) |
| C(8B)—O(3B)—C(9B) | 113.4(7) |
| C(9B)—O(4B)—C(16B) | 108.9(10) |
| C(17B)—O(5B)—C(10B) | 116.0(7) |
| C(13B)—O(7B)—C(11B) | 107.6(7) |
| C(13B)—O(8B)—C(12B) | 107.3(6) |
| C(19B)—O(9B)—C(2B) | 116.0(9) |
| C(3B)—O(10B)—C(26B) | 116.0(6) |
| C(33B)—O(11B)—C(4B) | 118.2(9) |
| C(40B)—O(12B)—C(5B) | 117.7(7) |

TABLE 8

Anisotropic displacement parameters ($Å^2 \times 10^3$) for compound 26. The anisotropic displacement factor exponent takes the form:
$-2\Pi^2[h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| C(1) | 43(4) | 39(5) | 52(5) | −2(4) | 17(4) | 2(4) |
| C(2) | 39(4) | 31(5) | 47(4) | 8(4) | 12(3) | −1(4) |
| C(3) | 35(4) | 32(4) | 43(4) | −2(4) | 13(3) | −1(4) |
| C(4) | 46(5) | 40(5) | 42(5) | 9(4) | 10(3) | −4(4) |
| C(5) | 28(4) | 38(5) | 65(5) | 0(5) | 9(4) | 2(4) |
| C(6) | 43(5) | 48(6) | 54(5) | −8(5) | 9(4) | 3(5) |
| C(7) | 34(4) | 30(5) | 65(5) | −1(4) | 10(4) | −5(4) |
| C(8) | 31(4) | 30(4) | 65(5) | 5(4) | 16(3) | 6(4) |
| C(9) | 30(4) | 39(5) | 61(5) | 5(4) | 19(4) | −2(4) |
| C(10) | 35(4) | 32(5) | 59(5) | 5(4) | 13(4) | −2(4) |
| C(11) | 45(5) | 38(5) | 53(5) | −9(4) | 23(4) | −8(4) |
| C(12) | 42(5) | 42(5) | 50(5) | −4(4) | 19(4) | −3(4) |
| C(13) | 59(6) | 53(6) | 67(6) | −9(5) | 32(5) | −6(5) |
| C(14) | 86(7) | 81(9) | 60(6) | −23(6) | 34(5) | 1(7) |
| C(15) | 54(6) | 65(7) | 76(6) | −3(6) | 35(5) | −4(6) |
| C(16) | 37(5) | 36(6) | 95(7) | −4(5) | 23(4) | −4(5) |
| C(17) | 47(5) | 62(7) | 94(7) | 3(6) | 30(5) | −9(5) |
| C(18) | 69(7) | 150(14) | 45(5) | −23(7) | 16(5) | −8(8) |
| C(19) | 42(5) | 61(6) | 49(5) | −10(5) | 14(4) | −13(5) |
| C(20) | 42(5) | 61(6) | 65(6) | −11(5) | 16(4) | −5(5) |
| C(21) | 52(6) | 73(9) | 180(13) | 43(10) | 34(8) | 9(7) |
| C(22) | 52(6) | 90(10) | 125(11) | 33(9) | 29(7) | −13(7) |
| C(23) | 98(11) | 90(11) | 127(13) | −11(10) | 34(9) | 17(10) |
| C(24) | 124(13) | 95(11) | 101(10) | −26(9) | 60(9) | −26(10) |
| C(25) | 101(9) | 111(12) | 73(7) | −26(8) | 33(7) | −14(9) |
| C(26) | 88(7) | 40(5) | 40(5) | 0(4) | 3(4) | −11(5) |
| C(27) | 54(5) | 39(5) | 53(5) | 1(4) | 16(4) | −9(5) |
| C(28) | 111(11) | 74(10) | 117(11) | 2(9) | 18(9) | 3(9) |
| C(29) | 150(16) | 123(15) | 97(11) | 53(11) | 61(10) | 20(13) |
| C(30) | 138(13) | 60(8) | 63(7) | 17(6) | 21(8) | 45(9) |
| C(31) | 101(10) | 102(12) | 91(9) | 25(8) | 12(8) | 42(9) |
| C(32) | 73(7) | 101(11) | 77(7) | −4(8) | 28(6) | 4(8) |
| C(33) | 135(11) | 67(8) | 60(6) | −13(6) | 51(6) | −42(8) |
| C(34) | 72(6) | 48(6) | 41(5) | 2(5) | 21(4) | −1(5) |
| C(35) | 151(12) | 68(8) | 63(7) | −32(7) | 37(7) | −35(9) |
| C(36) | 164(14) | 102(11) | 42(6) | −1(7) | 51(7) | −7(11) |
| C(37) | 90(9) | 82(10) | 106(11) | 10(8) | 56(7) | −16(8) |
| C(38) | 91(9) | 122(12) | 58(7) | −10(7) | 28(6) | −53(9) |
| C(39) | 77(7) | 82(9) | 39(5) | 5(5) | 12(4) | −17(7) |
| C(40) | 46(6) | 67(8) | 77(7) | −15(7) | 6(5) | 23(6) |
| C(41) | 59(7) | 126(13) | 108(9) | −30(9) | 6(6) | 38(8) |
| C(1B) | 63(6) | 49(6) | 52(5) | 9(5) | 14(4) | −1(5) |

TABLE 8-continued

Anisotropic displacement parameters ($A^2 \times 10^3$) for compound 26. The anisotropic displacement factor exponent takes the form:
$-2\Pi^2[h^2a^{*2}U^{11} + \ldots + 2 h k a^* b^* U^{12}]$

|  | $U^{11}$ | $U^{22}$ | $U^{33}$ | $U^{23}$ | $U^{13}$ | $U^{12}$ |
|---|---|---|---|---|---|---|
| C(2B) | 41(5) | 39(5) | 53(5) | 1(4) | 3(4) | 1(4) |
| C(3B) | 47(5) | 38(5) | 37(4) | 5(4) | 8(3) | 11(4) |
| C(4B) | 38(4) | 37(5) | 48(5) | 3(4) | 13(3) | 12(4) |
| C(5B) | 39(5) | 37(5) | 46(5) | −5(4) | 6(3) | 2(4) |
| C(6B) | 54(5) | 38(5) | 44(5) | −6(4) | 1(4) | 0(5) |
| C(7B) | 42(5) | 26(4) | 67(6) | 1(4) | 8(4) | −2(4) |
| C(8B) | 40(5) | 40(5) | 74(6) | 3(5) | 10(4) | 0(4) |
| C(9B) | 45(5) | 49(6) | 51(5) | −3(5) | 8(4) | 2(5) |
| C(10B) | 35(4) | 27(4) | 50(5) | −5(4) | 11(3) | −1(4) |
| C(11B) | 51(5) | 33(5) | 46(5) | 5(4) | 17(4) | −5(4) |
| C(12B) | 45(5) | 36(5) | 44(5) | −8(4) | 9(3) | −5(4) |
| C(13B) | 74(7) | 63(7) | 57(6) | −5(6) | 16(5) | −2(6) |
| C(14B) | 105(9) | 108(11) | 58(6) | 17(7) | 11(6) | −3(9) |
| C(15B) | 77(8) | 79(9) | 152(12) | −44(9) | 38(8) | 6(8) |
| C(16B) | 81(8) | 200(20) | 51(6) | 35(9) | 12(5) | 17(10) |
| C(17B) | 42(5) | 37(6) | 74(6) | 8(5) | 24(4) | 3(5) |
| C(18B) | 54(5) | 37(5) | 90(7) | 10(5) | 29(5) | 7(5) |
| C(19B) | 58(6) | 82(9) | 106(9) | 27(8) | 9(6) | −11(7) |
| C(20B) | 43(6) | 91(11) | 203(16) | 80(12) | 37(8) | 2(7) |
| C(21B) | 62(9) | 115(15) | 340(30) | 92(19) | 65(12) | 19(10) |
| C(22B) | 61(9) | 150(20) | 480(50) | 160(30) | 108(17) | 38(12) |
| C(23B) | 260(40) | 220(40) | 510(60) | 280(40) | 310(40) | 160(30) |
| C(24B) | 340(40) | 280(40) | 450(50) | 270(40) | 360(50) | 200(40) |
| C(25B) | 159(19) | 210(30) | 171(18) | 63(19) | 110(16) | 80(20) |
| C(26B) | 62(6) | 55(6) | 45(5) | −8(5) | 3(4) | 18(5) |
| C(27B) | 42(5) | 39(5) | 58(5) | −2(4) | 6(4) | 14(5) |
| C(28B) | 63(6) | 61(7) | 52(5) | −6(5) | 1(4) | 12(6) |
| C(29B) | 100(9) | 51(7) | 53(6) | −11(6) | −15(6) | −4(7) |
| C(30B) | 121(11) | 54(7) | 79(8) | 2(7) | −22(8) | 24(9) |
| C(31B) | 107(9) | 44(6) | 88(8) | 4(6) | 17(7) | −4(7) |
| C(32B) | 78(7) | 36(5) | 66(6) | −6(5) | 3(5) | −1(6) |
| C(33B) | 310(30) | 260(30) | 65(8) | −87(13) | 95(13) | −220(30) |
| C(34B) | 89(9) | 94(11) | 97(9) | −8(8) | 37(7) | 3(9) |
| C(35B) | 105(10) | 114(13) | 103(9) | −31(10) | 42(8) | −31(10) |
| C(36B) | 125(13) | 92(12) | 138(13) | −40(11) | 29(11) | −14(10) |
| C(37B) | 146(16) | 150(20) | 139(15) | −45(14) | 53(13) | −16(16) |
| C(38B) | 164(17) | 150(19) | 133(14) | −51(14) | 93(13) | −22(17) |
| C(39B) | 123(13) | 152(19) | 127(13) | −33(13) | 56(10) | −21(13) |
| C(40B) | 48(5) | 60(7) | 66(6) | −18(6) | 7(5) | −1(5) |
| C(41B) | 52(6) | 95(10) | 114(9) | −37(8) | 36(6) | −29(7) |
| O(1) | 41(3) | 40(4) | 68(4) | 9(3) | 14(3) | 0(3) |
| O(2) | 38(3) | 41(4) | 54(3) | −4(3) | 11(2) | −9(3) |
| O(3) | 45(3) | 37(3) | 54(3) | −4(3) | 16(2) | −7(3) |
| O(4) | 53(4) | 67(5) | 51(3) | 3(4) | 9(3) | −7(4) |
| O(5) | 35(3) | 30(3) | 79(4) | −1(3) | 17(3) | −6(3) |
| O(6) | 53(4) | 44(5) | 178(9) | 5(5) | 33(5) | 6(4) |
| O(7) | 52(3) | 55(4) | 61(4) | −1(3) | 32(3) | 11(3) |
| O(8) | 46(3) | 56(4) | 54(3) | −2(3) | 23(3) | −3(3) |
| O(9) | 42(3) | 45(4) | 54(3) | −6(3) | 18(3) | −3(3) |
| O(10) | 57(3) | 35(3) | 33(3) | 2(3) | 7(2) | −7(3) |
| O(11) | 64(4) | 58(4) | 38(3) | 4(3) | 19(3) | 8(3) |
| O(12) | 46(3) | 57(4) | 67(4) | −16(3) | 15(3) | 4(3) |
| O(13) | 79(5) | 68(6) | 95(6) | 22(5) | 22(4) | 35(5) |
| O(1B) | 42(3) | 39(4) | 72(4) | −6(3) | −1(3) | 3(3) |
| O(2B) | 52(3) | 37(3) | 51(3) | −2(3) | −4(3) | 12(3) |
| O(3B) | 37(3) | 41(3) | 54(3) | −2(3) | 7(2) | 1(3) |
| O(4B) | 54(4) | 120(7) | 42(3) | −10(4) | 11(3) | −7(5) |
| O(5B) | 37(3) | 32(3) | 66(4) | 1(3) | 11(2) | 1(3) |
| O(6B) | 51(4) | 30(4) | 149(7) | −1(4) | 23(4) | −9(3) |
| O(7B) | 65(4) | 61(4) | 45(3) | −5(3) | 19(3) | −17(4) |
| O(8B) | 51(4) | 54(4) | 58(4) | −3(3) | 8(3) | −1(3) |
| O(9B) | 43(3) | 56(4) | 81(4) | 5(4) | 25(3) | −2(3) |
| O(10B) | 42(3) | 48(4) | 40(3) | −2(3) | 5(2) | 6(3) |
| O(11B) | 64(4) | 61(4) | 41(3) | −3(3) | 15(3) | 6(4) |
| O(12B) | 38(3) | 43(4) | 63(4) | −10(3) | 8(3) | −5(3) |
| O(13B) | 74(5) | 67(5) | 102(5) | −39(5) | 28(4) | −18(5) |

TABLE 9

Hydrogen coordinates (×10⁴) and isotropic displacement parameters ($Å^2 \times 10^3$) for compound 26.

| | x | y | z | U(eq) |
|---|---|---|---|---|
| H(1A) | 7029 | 6512 | 8749 | 52 |
| H(1B) | 7281 | 5180 | 8992 | 52 |
| H(2) | 7491 | 6663 | 9860 | 46 |
| H(3) | 7436 | 9188 | 9782 | 43 |
| H(4) | 6865 | 9652 | 9844 | 51 |
| H(5) | 6604 | 8306 | 8973 | 52 |
| H(6) | 6444 | 5981 | 9658 | 58 |
| H(7) | 6399 | 3838 | 8913 | 51 |
| H(8A) | 6435 | 4461 | 7951 | 49 |
| H(8B) | 6135 | 3286 | 7967 | 49 |
| H(9) | 5589 | 3702 | 7666 | 50 |
| H(10) | 5298 | 6447 | 7899 | 50 |
| H(11) | 5771 | 6604 | 8621 | 52 |
| H(12) | 5760 | 3502 | 8702 | 52 |
| H(14A) | 5658 | 5152 | 10431 | 110 |
| H(14B) | 5391 | 6356 | 10116 | 110 |
| H(14C) | 5801 | 6503 | 10120 | 110 |
| H(15A) | 5292 | 3196 | 9170 | 93 |
| H(15B) | 5096 | 3985 | 9618 | 93 |
| H(15C) | 5429 | 2980 | 9847 | 93 |
| H(17A) | 4370 | 4293 | 8418 | 98 |
| H(17B) | 4671 | 3098 | 8451 | 98 |
| H(17C) | 4429 | 3497 | 7844 | 98 |
| H(18A) | 5780 | 4465 | 6644 | 131 |
| H(18B) | 5402 | 4728 | 6251 | 131 |
| H(18C) | 5467 | 3362 | 6676 | 131 |
| H(19A) | 8077 | 7708 | 9833 | 60 |
| H(19B) | 7920 | 9034 | 9419 | 60 |
| H(21) | 8691 | 7372 | 9710 | 120 |
| H(22) | 9064 | 6701 | 8962 | 105 |
| H(23) | 8866 | 7141 | 8040 | 124 |
| H(24) | 8325 | 7926 | 7691 | 122 |
| H(25) | 7922 | 8257 | 8294 | 111 |
| H(26A) | 7451 | 11062 | 9139 | 68 |
| H(26B) | 7044 | 11214 | 9163 | 68 |
| H(28) | 7635 | 11517 | 8203 | 122 |
| H(29) | 7486 | 12138 | 7220 | 142 |
| H(30) | 6955 | 12461 | 6775 | 104 |
| H(31) | 6473 | 11784 | 7280 | 118 |
| H(32) | 6613 | 11137 | 8244 | 98 |
| H(33A) | 6778 | 9680 | 10659 | 100 |
| H(33B) | 7154 | 9211 | 11014 | 100 |
| H(35) | 6914 | 9338 | 11899 | 110 |
| H(36) | 6636 | 8173 | 12552 | 118 |
| H(37) | 6320 | 6112 | 12287 | 105 |
| H(38) | 6250 | 5331 | 11368 | 106 |
| H(39) | 6500 | 6521 | 10698 | 79 |
| H(41A) | 5779 | 10959 | 9640 | 149 |
| H(41B) | 5808 | 9343 | 9894 | 149 |
| H(41C) | 5620 | 9623 | 9240 | 149 |
| H(1B1) | 3408 | 1406 | 6972 | 65 |
| H(1B2) | 3192 | −37 | 6750 | 65 |
| H(2B) | 2989 | 1255 | 5820 | 54 |
| H(3B) | 2991 | 3766 | 5818 | 48 |
| H(4B) | 3563 | 4411 | 5853 | 48 |
| H(5B) | 3773 | 3209 | 6802 | 49 |
| H(6B) | 4024 | 974 | 6154 | 56 |
| H(7B) | 4079 | −1158 | 6900 | 54 |
| H(8B1) | 4026 | −511 | 7864 | 62 |
| H(8B2) | 4334 | −1668 | 7869 | 62 |
| H(9B) | 4856 | −1291 | 8187 | 58 |
| H(10B) | 5170 | 1428 | 7971 | 45 |
| H(11B) | 4700 | 1640 | 7215 | 51 |
| H(12B) | 4701 | −1470 | 7118 | 50 |
| H(14D) | 4720 | 621 | 5412 | 136 |
| H(14E) | 5062 | 1518 | 5699 | 136 |
| H(14F) | 4689 | 1939 | 5841 | 136 |
| H(15D) | 5241 | −1622 | 6610 | 150 |
| H(15E) | 5339 | −889 | 6048 | 150 |
| H(15F) | 5015 | −1987 | 5986 | 150 |
| H(16A) | 4619 | −602 | 9076 | 164 |
| H(16B) | 4942 | −127 | 9566 | 164 |
| H(16C) | 4966 | −1572 | 9199 | 164 |
| H(18D) | 6093 | −795 | 7485 | 87 |
| H(18E) | 5777 | −1931 | 7424 | 87 |

TABLE 9-continued

Hydrogen coordinates (×10⁴) and isotropic displacement parameters ($Å^2 \times 10^3$) for compound 26.

| | x | y | z | U(eq) |
|---|---|---|---|---|
| H(18F) | 6009 | −1581 | 8045 | 87 |
| H(19C) | 2578 | −173 | 6389 | 99 |
| H(19D) | 2384 | 779 | 5851 | 99 |
| H(21B) | 1817 | 22 | 6002 | 202 |
| H(22B) | 1342 | 411 | 6452 | 267 |
| H(23B) | 1416 | 1735 | 7311 | 357 |
| H(24B) | 1967 | 2670 | 7721 | 383 |
| H(25B) | 2442 | 2282 | 7271 | 202 |
| H(26C) | 2958 | 5549 | 7056 | 66 |
| H(26D) | 2700 | 4409 | 6679 | 66 |
| H(28B) | 2304 | 5648 | 5958 | 72 |
| H(29B) | 2174 | 7361 | 5208 | 87 |
| H(30B) | 2623 | 8618 | 4920 | 108 |
| H(31B) | 3195 | 8541 | 5500 | 96 |
| H(32B) | 3317 | 6867 | 6261 | 73 |
| H(33C) | 3956 | 3134 | 5304 | 243 |
| H(33D) | 3636 | 3884 | 4875 | 243 |
| H(35B) | 3337 | 410 | 4806 | 125 |
| H(36B) | 3347 | −1249 | 4047 | 141 |
| H(37B) | 3721 | −961 | 3403 | 168 |
| H(38B) | 4105 | 1131 | 3477 | 168 |
| H(39B) | 4148 | 2670 | 4262 | 156 |
| H(41D) | 4621 | 6321 | 6623 | 126 |
| H(41E) | 4578 | 5318 | 6061 | 126 |
| H(41F) | 4758 | 4679 | 6676 | 126 |

TABLE 10

Torsion angles [°] for compound 26.

| | |
|---|---|
| O(1)—C(1)—C(2)—O(9) | 162.3(6) |
| O(1)—C(1)—C(2)—C(3) | −74.5(9) |
| O(9)—C(2)—C(3)—O(10) | 51.6(8) |
| C(1)—C(2)—C(3)—O(10) | −65.4(8) |
| O(9)—C(2)—C(3)—C(4) | 173.1(6) |
| C(1)—C(2)—C(3)—C(4) | 56.1(9) |
| O(10)—C(3)—C(4)—O(11) | 176.0(7) |
| C(2)—C(3)—C(4)—O(11) | 55.7(9) |
| O(10)—C(3)—C(4)—C(5) | 52.0(9) |
| C(2)—C(3)—C(4)—C(5) | −68.3(9) |
| O(11)—C(4)—C(5)—O(12) | 72.4(9) |
| C(3)—C(4)—C(5)—O(12) | −163.0(7) |
| O(11)—C(4)—C(5)—C(6) | −43.9(11) |
| C(3)—C(4)—C(5)—C(6) | 80.7(10) |
| O(12)—C(5)—C(6)—O(1) | −154.6(7) |
| C(4)—C(5)—C(6)—O(1) | −34.7(12) |
| O(12)—C(5)—C(6)—O(2) | 85.3(8) |
| C(4)—C(5)—C(6)—O(2) | −154.8(7) |
| O(2)—C(7)—C(8)—O(3) | −65.2(8) |
| C(12)—C(7)—C(8)—O(3) | 54.5(9) |
| O(3)—C(9)—C(10)—O(5) | −155.2(6) |
| O(4)—C(9)—C(10)—O(5) | 88.4(8) |
| O(3)—C(9)—C(10)—C(11) | −36.7(10) |
| O(4)—C(9)—C(10)—C(11) | −153.1(7) |
| O(5)—C(10)—C(11)—O(7) | −45.2(10) |
| C(9)—C(10)—C(11)—O(7) | −160.6(7) |
| O(5)—C(10)—C(11)—C(12) | 74.7(9) |
| C(9)—C(10)—C(11)—C(12) | −40.7(10) |
| O(7)—C(11)—C(12)—O(8) | −25.9(8) |
| C(10)—C(11)—C(12)—O(8) | −149.9(7) |
| O(7)—C(11)—C(12)—C(7) | −144.6(7) |
| C(10)—C(11)—C(12)—C(7) | 91.4(9) O(2) |
| C(7)—C(12)—O(8) | −68.8(9) |
| C(8)—C(7)—C(12)—O(8) | 174.3(7) |
| O(2)—C(7)—C(12)—C(11) | 44.7(9) |
| C(8)—C(7)—C(12)—C(11) | −72.1(9) |
| O(9)—C(19)—C(20)—C(21) | −130.3(11) |
| O(9)—C(19)—C(20)—C(25) | 53.8(13) |
| C(25)—C(20)—C(21)—C(22) | −8.4(18) |
| C(19)—C(20)—C(21)—C(22) | 175.7(11) |
| C(20)—C(21)—C(22)—C(23) | 9(2) |
| C(21)—C(22)—C(23)—C(24) | −3(3) |

TABLE 10-continued

Torsion angles [°] for compound 26.

| Atoms | Angle |
|---|---|
| C(22)—C(23)—C(24)—C(25) | −2(3) |
| C(23)—C(24)—C(25)—C(20) | 2(2) |
| C(21)—C(20)—C(25)—C(24) | 4(2) |
| C(19)—C(20)—C(25)—C(24) | −180.0(13) |
| O(10)—C(26)—C(27)—C(32) | 80.4(13) |
| O(10)—C(26)—C(27)—C(28) | −99.8(12) |
| C(32)—C(27)—C(28)—C(29) | −1(2) |
| C(26)—C(27)—C(28)—C(29) | 178.8(14) |
| C(27)—C(28)—C(29)—C(30) | 3(3) |
| C(28)—C(29)—C(30)—C(31) | −5(3) |
| C(29)—C(30)—C(31)—C(32) | 4(2) |
| C(28)—C(27)—C(32)—C(31) | 1(2) |
| C(26)—C(27)—C(32)—C(31) | −179.1(13) |
| C(30)—C(31)—C(32)—C(27) | −2(2) |
| O(11)—C(33)—C(34)—C(35) | 159.2(12) |
| O(11)—C(33)—C(34)—C(39) | −26.3(18) |
| C(39)—C(34)—C(35)—C(36) | 3(2) |
| C(33)—C(34)—C(35)—C(36) | 177.9(15) |
| C(34)—C(35)—C(36)—C(37) | 1(3) |
| C(35)—C(36)—C(37)—C(38) | −3(3) |
| C(36)—C(37)—C(38)—C(39) | 1(2) |
| C(35)—C(34)—C(39)—C(38) | −4.5(19) |
| C(33)—C(34)—C(39)—C(38) | −179.3(14) |
| C(37)—C(38)—C(39)—C(34) | 3(2) |
| O(1B)—C(1B)—C(2B)—O(9B) | 165.7(7) |
| O(1B)—C(1B)—C(2B)—C(3B) | −75.9(10) |
| O(9B)—C(2B)—O(3B)—O(10B) | 54.2(8) |
| C(1B)—C(2B)—C(3B)—O(10B) | −66.2(10) |
| O(9B)—C(2B)—C(3B)—C(4B) | 175.1(6) |
| C(1B)—C(2B)—C(3B)—C(4B) | 54.6(10) |
| O(10B)—C(3B)—C(4B)—O(11B) | −178.8(7) |
| C(2B)—C(3B)—C(4B)—O(11B) | 57.2(9) |
| O(10B)—C(3B)—C(4B)—C(5B) | 55.0(9) |
| C(2B)—C(3B)—C(4B)—C(5B) | −69.0(9) |
| O(11B)—C(4B)—C(5B)—O(12B) | 79.1(9) |
| C(3B)—C(4B)—C(5B)—O(12B) | −156.7(7) |
| O(11B)—C(4B)—C(5B)—C(6B) | −39.3(11) |
| C(3B)—C(4B)—C(5B)—C(6B) | 85.0(10) |
| O(12B)—C(5B)—C(6B)—O(1B) | −161.8(7) |
| C(4B)—C(5B)—C(6B)—O(1B) | −40.4(11) |
| O(12B)—C(5B)—C(6B)—O(2B) | 75.5(8) |
| C(4B)—C(5B)—C(6B)—O(2B) | −163.0(7) |
| O(2B)—C(7B)—C(8B)—O(3B) | −66.4(9) |
| C(12B)—C(7B)—C(8B)—O(3B) | 55.1(10) |
| O(4B)—C(9B)—C(10B)—O(5B) | 88.3(8) |
| O(3B)—C(9B)—C(10B)—O(5B) | −154.7(6) |
| O(4B)—C(9B)—C(10B)—C(11B) | −152.3(7) |
| O(3B)—C(9B)—O(10B)—C(11B) | −35.2(10) |
| O(5B)—C(10B)—C(11B)—O(7B) | −43.3(9) |
| C(9B)—C(10B)—C(11B)—O(7B) | −159.6(7) |
| O(5B)—C(10B)—C(11B)—C(12B) | 73.5(9) |
| C(9B)—C(10B)—C(11B)—C(12B) | −42.9(10) |
| O(2B)—C(7B)—C(12B)—O(8B) | −67.9(9) |
| C(8B)—C(7B)—C(12B)—O(8B) | 175.0(7) |
| O(2B)—C(7B)—C(12B)—C(11B) | 47.9(9) |
| C(8B)—C(7B)—C(12B)—C(11B) | −69.1(9) |
| O(7B)—C(11B)—C(12B)—O(8B) | −28.4(8) |
| C(10B)—C(11B)—C(12B)—O(8B) | −148.4(7) |
| O(7B)—C(11B)—C(12B)—C(7B) | −149.1(7) |
| C(10B)—C(11B)—C(12B)—C(7B) | 90.9(9) |
| O(9B)—C(19B)—C(20B)—C(21B) | 154.9(8) |
| O(9B)—C(19B)—C(20B)—C(25B) | −26.0(13) |
| C(25B)—C(20B)—C(21B)—C(22B) | 0.0 |
| C(19B)—C(20B)—C(21B)—C(22B) | 179.2(10) |
| C(20B)—C(21B)—C(22B)—C(23B) | 0.0 |
| C(21B)—C(22B)—C(23B)—C(24B) | 0.0 |
| C(22B)—C(23B)—C(24B)—C(25B) | 0.0 |
| C(23B)—C(24B)—C(25B)—C(20B) | 0.0 |
| C(21B)—C(20B)—C(25B)—C(24B) | 0.0 |
| C(19B)—C(20B)—C(25B)—C(24B) | −179.1(11) |
| O(10B)—C(26B)—C(27B)—C(32B) | −48.3(12) |
| O(10B)—C(26B)—C(27B)—C(28B) | 128.0(9) |
| C(32B)—C(27B)—C(28B)—C(29B) | −2.2(15) |
| C(26B)—C(27B)—C(28B)—C(29B) | −178.7(9) |
| C(27B)—C(28B)—C(29B)—C(30B) | 4.7(17) |
| C(28B)—C(29B)—C(30B)—C(31B) | −6.1(19) |
| C(29B)—C(30B)—C(31B)—C(32B) | 5.3(19) |
| C(28B)—C(27B)—C(32B)—C(31B) | 1.4(15) |
| C(26B)—C(27B)—C(32B)—C(31B) | 177.8(10) |
| C(30B)—C(31B)—C(32B)—C(27B) | −2.9(17) |
| O(11B)—C(33B)—C(34B)—C(35B) | 10(3) |
| O(11B)—C(33B)—C(34B)—C(39B) | −175.9(18) |
| C(39B)—C(34B)—C(35B)—C(36B) | −1(2) |
| C(33B)—C(34B)—C(35B)—C(36B) | 174.0(19) |
| C(34B)—C(35B)—C(36B)—C(37B) | −1(3) |
| C(35B)—C(36B)—C(37B)—C(38B) | −1(3) |
| C(36B)—C(37B)—C(38B)—C(39B) | 4(4) |
| C(37B)—C(38B)—C(39B)—C(34B) | −6(3) |
| C(35B)—C(34B)—C(39B)—C(38B) | 4(3) |
| C(33B)—C(34B)—C(39B)—C(38B) | −171(2) |
| O(2)—C(6)—O(1)—C(1) | 69.5(9) |
| C(5)—C(6)—O(1)—C(1) | −47.2(10) |
| C(2)—C(1)—O(1)—C(6) | 95.2(8) |
| C(8)—C(7)—O(2)—C(6) | −152.0(7) |
| C(12)—C(7)—O(2)—C(6) | 89.3(8) |
| O(1)—C(6)—O(2)—C(7) | 69.2(9) |
| C(5)—C(6)—O(2)—C(7) | −167.1(7) |
| O(4)—C(9)—O(3)—C(8) | −144.3(7) |
| C(10)—C(9)—O(3)—C(8) | 98.5(8) |
| C(7)—C(8)—O(3)—C(9) | −85.0(8) |
| O(3)—C(9)—O(4)—C(18) | 75.5(10) |
| C(10)—C(9)—O(4)—C(18) | −165.2(7) |
| O(6)—C(16)—O(5)—C(10) | 7.0(15) |
| C(17)—C(16)—O(5)—C(10) | −175.9(8) |
| C(11)—C(10)—O(5)—C(16) | 99.1(9) |
| C(9)—C(10)—O(5)—C(16) | −140.2(8) |
| O(10)—C(11)—O(7)—C(13) | 131.0(8) |
| C(12)—C(11)—O(7)—C(13) | 5.8(9) |
| O(8)—C(13)—O(7)—C(11) | 17.2(9) |
| C(14)—C(13)—O(7)—C(11) | 132.6(8) |
| C(15)—C(13)—O(7)—C(11) | −102.2(8) |
| O(7)—C(13)—O(8)—C(12) | −34.5(9) |
| C(14)—C(13)—O(8)—C(12) | −150.9(9) |
| C(15)—C(13)—O(8)—C(12) | 84.2(9) |
| C(11)—C(12)—O(8)—C(13) | 37.0(9) |
| C(7)—C(12)—O(8)—C(13) | 158.7(8) |
| C(3)—C(2)—O(9)—C(19) | 58.6(9) |
| C(1)—C(2)—O(9)—C(19) | −178.2(7) |
| C(20)—C(19)—O(9)—C(2) | 175.7(7) |
| C(27)—C(26)—O(10)—C(3) | 178.7(7) |
| C(2)—C(3)—O(10)—C(26) | −148.7(8) |
| C(4)—C(3)—O(10)—C(26) | 85.5(9) |
| C(3)—C(4)—O(11)—C(33) | 118.9(9) |
| C(5)—C(4)—O(11)—C(33) | −115.8(9) |
| C(34)—C(33)—O(11)—C(4) | 142.7(10) |
| O(13)—C(40)—O(12)—C(5) | −5.2(14) |
| C(41)—C(40)—O(12)—C(5) | 175.4(8) |
| C(6)—C(5)—O(12)—C(40) | −151.9(8) |
| C(4)—C(5)—O(12)—C(40) | 82.8(9) |
| O(2B)—C(6B)—O(1B)—C(1B) | 74.4(9) |
| C(5B)—C(6B)—O(1B)—C(1B) | −43.4(10) |
| C(2B)—C(1B)—O(1B)—C(6B) | 95.9(9) |
| O(1B)—C(6B)—O(2B)—C(7B) | 65.3(10) |
| C(5B)—C(6B)—O(2B)—C(7B) | −169.1(7) |
| C(12B)—C(7B)—O(2B)—C(6B) | 90.0(9) |
| C(8B)—C(7B)—O(2B)—C(6B) | −149.8(7) |
| C(7B)—C(8B)—O(3B)—C(9B) | −87.3(9) |
| O(4B)—C(9B)—O(3B)—C(8B) | −144.2(8) |
| C(10B)—C(9B)—O(3B)—C(8B) | 100.4(9) |
| O(3B)—C(9B)—O(4B)—C(16B) | 72.6(12) |
| C(10B)—C(9B)—O(4B)—C(16B) | −168.4(10) |
| O(6B)—C(17B)—O(5B)—C(10B) | 5.0(14) |
| C(18B)—C(17B)—O(5B)—C(10B) | −175.8(7) |
| C(9B)—C(10B)—O(5B)—C(17B) | −143.5(7) |
| C(11B)—C(10B)—O(5B)—C(17B) | 97.0(8) |
| O(8B)—C(13B)—O(7B)—C(11B) | 7.0(11) |
| C(15B)—C(13B)—O(7B)—C(11B) | −113.4(10) |
| C(14B)—C(13B)—O(7B)—C(11B) | 122.5(9) |
| C(12B)—C(11B)—O(7B)—C(13B) | 13.3(9) |
| C(10B)—C(11B)—O(7B)—C(13B) | 137.4(8) |
| O(7B)—C(13B)—O(8B)—C(12B) | −26.4(11) |
| C(15B)—C(13B)—O(8B)—C(12B) | 91.1(10) |
| C(14B)—C(13B)—O(8B)—C(12B) | −141.6(9) |
| C(7B)—C(12B)—O(8B)—C(13B) | 156.3(8) |
| C(11B)—C(12B)—O(8B)—C(13B) | 33.7 |
| C(20B)—C(19B)—O(9B)—C(2B) | 175.4(8) |

TABLE 10-continued

Torsion angles [°] for compound 26.

| | |
|---|---|
| C(3B)—C(2B)—O(9B)—C(19B) | 149.7(8) |
| C(1B)—C(2B)—O(9B)—C(19B) | −87.3(10) |
| C(2B)—C(3B)—O(10B)—C(26B) | −95.7(9) |
| C(4B)—C(3B)—O(10B)—C(26B) | 138.6(8) |
| C(27B)—C(26B)—O(10B)—C(3B) | −59.6(10) |
| C(34B)—C(33B)—O(11B)—C(4B) | 165.2(13) |
| C(3B)—C(4B)—O(11B)—C(33B) | 153.7(17) |
| C(5B)—C(4B)—O(11B)—C(33B) | −80.9(19) |
| O(13B)—C(40B)—O(12B)—C(5B) | −3.4(13) |
| C(41B)—C(40B)—O(12B)—C(5B) | 178.7(8) |
| C(6B)—C(5B)—O(12B)—C(40B) | −150.4(7) |
| C(4B)—C(5B)—O(12B)—C(40B) | 86.4(9) |

Example 4

D. Iterative Glycosylation Synthesis of D-Mannopyranosyl Di- and Trisaccharides

1. Synthesis of Disaccharide 27

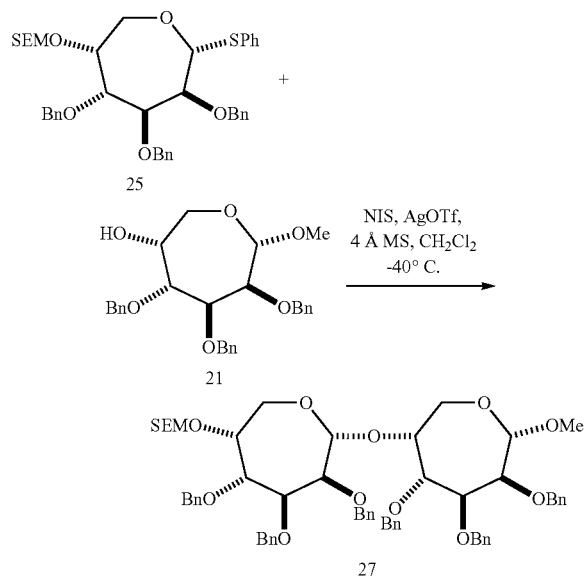

Thioglycoside 25 (190 mg, 0.28 mmol) and methyl glycoside alcohol 21 were dissolved in CH$_2$Cl$_2$ (0.10 M, 2.8 mL). 4 Å MS (400 mg, powdered) were then added to the solution. The solution was cooled to −40° C. Then NIS (79 mg, 0.35 mmol) and AgOTf (21 mg, 0.08 mmol) were simultaneously added to the solution. The reaction was allowed to warm to −38° C., at which point the reaction became magenta in color. Upon the color change, TLC indicated the completion of the reaction. The reaction was quenched by the addition of Et$_3$N (1.0 mL), which caused an immediate color change to yellow. The mixture was filtered through celite, and the volatiles were evaporated under reduced pressure. Chromatography (4:1 hexanes:EtOAc) afforded disaccharide 27 as a colorless oil (230 mg, 80%).

[α]$_D^{23}$=+13.2 (c 1.20, CHCl$_3$); $^1$H NMR (400 MHz, CDCl$_3$) δ 7.33-7.18 (m, 28H), 7.05 (m, 2H), 4.89 (d, J=6.8 Hz, 1H), 4.79 (d, J=12.4 Hz, 1H), 4.79 (d, J=12.4 Hz, 1H), 4.75-4.55 (m, 9H), 4.49 (d, J=12.0 Hz, 1H), 4.43 (d, J=11.6 Hz, 1H), 4.39-4.27 (m, 3H), 4.18 (m, 1H), 4.07 (m, 5H), 3.82-3.71 (m, 4H), 3.63 (m, 3H), 3.50 (m, 1H), 3.43 (s, 3H), 0.966 (dd, J=6.4, 9.6 Hz, 2H), 0.041 (s, 9H); $^{13}$C NMR (100 MHz, CDCl$_3$) δ 138.9, 138.9, 138.7, 138.7, 138.6, 128.6, 128.5, 128.5, 128.4, 128.4, 128.3, 128.0, 127.9, 127.9, 127.6, 127.5, 103.5, 101.8, 94.1, 80.2, 78.4, 77.7, 77.4, 76.1, 75.8, 75.4, 73.9, 73.8, 73.7, 73.6, 73.2, 72.8, 65.5, 61.4, 66.4, 55.3, 18.3, −1.16; IR (KBr) 3030, 2951, 1454, 1093, 1066, 735, 698 cm$^{-1}$; HRMS (ESI) [M+NH$_4^+$] Calcd. for C$_{61}$H$_{78}$O$_{12}$N$_1$Si$_1$ 1044.52878, found 1044.53162.

2. Synthesis of Disaccharide Alcohol 28

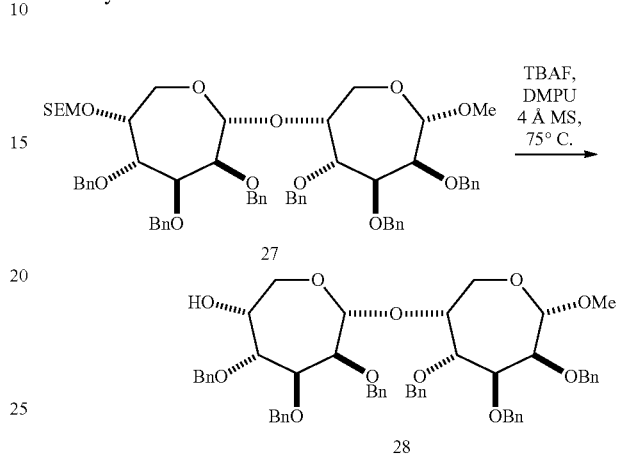

Disaccharide 27 (230 mg, 0.23 mmol) was dissolved in DMPU (0.23 M, 1.0 mL) and freshly activated 4 Å MS (200 mg, powdered) were added. Then TBAF (1.0 M in THF, 1.1 mL, 1.1 mmol) was added all at once. The reaction was stirred for 24 hours at 75° C. Then the reaction was diluted with EtOAc (100 mL) and quenched by the addition of H$_2$O (50 mL). The aqueous layer was extracted with EtOAc (2×50 mL). The organic layers were combined and dried with MgSO$_4$. After filtration and evaporation of the volatiles under reduced pressure, chromatography (4:1→2:1 hexanes:EtOAc) afforded disaccharide alcohol 28 as a colorless oil (180 mg, 87%).

[α]$_D^{23}$=+3.4 (c 1.00, CHCl$_3$); $^1$H NMR (400 MHz, CDCl$_3$) δ 7.36-7.19 (m, 26H), 7.07 (m, 4H), 4.91 (d, J=6.4 Hz, 1H), 4.83 (d, J=12.4 Hz, 1H), 4.75 (d, J=12.4 Hz, 1H), 4.67 (m, 3H), 4.64-4.42 (m, 3H), 4.41 (d, J=11.6 Hz, 1H), 4.35 (d, J=12.0 Hz, 1H), 4.29 (m, 2H), 4.22 (d, J=11.2 Hz, 1H), 4.18 (dt, J=3.2, 9.6 Hz, 1H), 4.07-3.96 (m, 4H), 3.91 (dd, J=6.0, 14.4 Hz, 1H), 3.82 (d, J=6.4 Hz, 1H), 3.76 (m, 3H), 3.67 (m, 1H), 3.58 (dd, J=3.2, 12.0 Hz, 1H), 3.43 (s, 3H), 2.25 (d, J=10.8 Hz, 1H); $^{13}$C NMR (100 MHz, CDCl$_3$) δ 138.9, 138.7, 138.6, 138.6, 138.3, 137.5, 128.8, 128.6, 128.5, 128.4, 128.4, 128.3, 128.1, 127.9, 127.8, 127.7, 127.6, 127.5, 103.6, 101.7, 80.1, 79.6, 78.3, 77.8, 76.7, 75.9, 75.7, 73.7, 73.7, 73.6, 73.5, 73.2, 72.9, 69.0, 62.3, 61.4, 55.3; IR (KBr) 3467, 3030, 2895, 1496, 1454, 1092, 737, 698 cm$^{-1}$; HRMS (ESI) [M+H] Calcd. for C$_{55}$H$_{61}$O$_{11}$ 897.42084, found 897.41925.

3. Synthesis of Trisaccharide 29

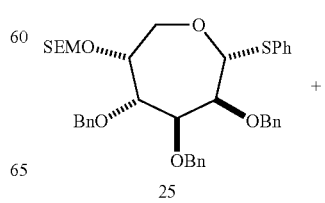

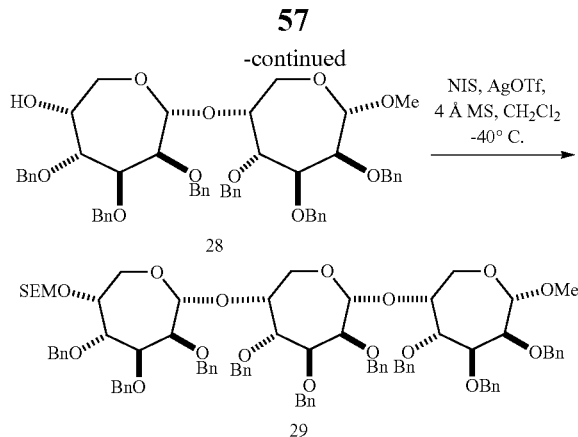

Thioglycoside 25 (71 mg, 0.11 mmol) and disaccharide alcohol 28 (93 mg, 0.10 mol) were dissolved in CH$_2$Cl$_2$ (0.10 M, 1.1 mL). 4 Å MS (200 mg, powdered) were then added to the solution. The solution was cooled to −40° C. Then NIS (31 mg, 0.14 mmol) and AgOTf (8 mg, 0.03 mmol) were simultaneously added to the solution. The reaction was allowed to warm to −38° C., at which point the reaction became magenta in color. Upon the color change, TLC indicated the completion of the reaction. The reaction was quenched by the addition of Et$_3$N (1.0 mL), which caused an immediate color change to yellow. The mixture was filtered through celite, and the volatiles were evaporated under reduced pressure. Chromatography (4:1 hexanes:EtOAc) gave trisaccharide 29 as a colorless oil (110 mg, 75%).

$[\alpha]_D^{23}$=+9.7 (c 0.50, CHCl$_3$); $^1$H NMR (400 MHz, CDCl$_3$) δ 7.32-7.17 (m, 41H), 7.04 (m, 4H), 4.88 (t, J=7.2 Hz, 2H), 4.78 (d, J=12.0 Hz, 1H), 4.73-4.54 (m, 13H), 4.51-4.34 (m, 5H), 4.27 (m, 2H), 4.16 (m, 2H), 4.04 (m, 6H), 3.78 (m, 6H), 3.62 (m, 4H), 3.52 (m, 1H), 3.43 (s, 3H), 1.27 (m, 2H), 0.958 (m, 2H), 0.036 (s, 9H); $^{13}$C NMR (100 MHz, CDCl$_3$) δ 138.9, 138.9, 138.8, 138.7, 138.6, 138.6, 128.5, 128.4, 128.4, 128.4, 128.3, 128.3, 128.3, 128.1, 127.9, 127.8, 127.8, 127.7, 127.7, 127.5, 127.5, 103.5, 101.7, 93.9, 80.2, 78.5, 77.8, 76.1, 75.8, 75.8, 75.3, 74.0, 73.9, 73.8, 73.7, 73.6, 73.5, 73.1, 72.8, 72.7, 65.5, 61.4, 60.4, 55.3, 29.9, 18.2, 14.4, −1.16; IR (KBr) 3030, 2895, 1496, 1454, 1248, 1092, 837, 733, 698 cm$^{-1}$; HRMS (ESI) [M+Na$^+$] Calcd. for C$_{88}$H$_{102}$O$_{17}$Na$_1$Si$_1$ 1481.67785, found 1481.68252.

4. Synthesis of Trisaccharide Alcohol 30

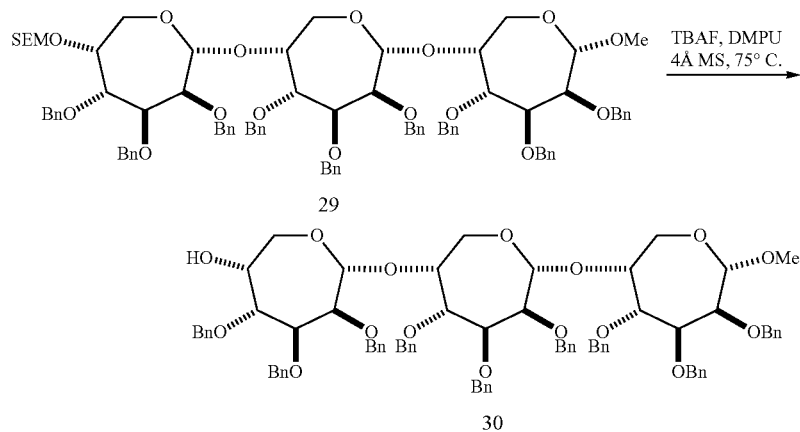

Trisaccharide 29 (110 mg, 0.08 mmol) was dissolved in DMPU (0.08 M, 1.0 mL) and freshly activated 4 Å MS (200 mg, powdered) were added. Then TBAF (1.0 M in THF, 0.40 mL, 0.40 mmol) was added all at once. The reaction was stirred for 3 hours at 75° C. Then the reaction was diluted with EtOAc (100 mL) and quenched by the addition of H$_2$O (50 mL). The aqueous layer was extracted with EtOAc (2×50 mL). The organic layers were combined and dried with MgSO$_4$. After filtration and evaporation of the volatiles under reduced pressure, chromatography (4:1→2:1 hexanes: EtOAc) afforded trisaccharide alcohol 30 as a colorless oil (78 mg, 74%).

$[\alpha]_D^{23}$=+10.8 (c 2.00, CHCl$_3$); $^1$H NMR (400 MHz, CDCl$_3$) δ 7.37-7.03 (m, 45H), 4.92 (d, J=6.8 Hz, 1H), 4.88 (d, J=6.8 Hz, 1H), 4.82 (d, J=12.4 Hz, 1H), 4.77-4.52 (m, 8H), 4.47-4.24 (m, 7H), 4.17 (m, 2H), 4.04 (m, 5H), 3.94 (m, 2H), 3.78 (m, 5H), 3.69 (m, 1H), 3.60 (m, 2H), 3.44 (s, 3H); $^{13}$C NMR (100 MHz, CDCl$_3$) δ 138.9, 138.9, 138.7, 138.7, 138.6, 138.4, 137.5, 128.8, 128.6, 128.5, 128.5, 128.4, 128.4, 128.3, 128.3, 128.1, 127.9, 127.9, 127.8, 127.7, 127.6, 127.5, 103.5, 101.8, 101.6, 80.2, 79.7, 78.5, 77.8, 75.9, 75.9, 75.6, 73.9, 73.8, 73.8, 73.7, 73.6, 73.2, 273.0, 72.7, 69.1, 62.3, 61.5, 60.6, 55.3; IR (KBr) 3479, 3030, 2893, 1496, 1454, 1336, 1244, 1207, 1092, 735, 698 cm$^{-1}$; HRMS (ESI) [M+Na$^+$] Calcd. for C$_{82}$H$_{88}$O$_{16}$Na$_1$ 1351.59646, found 1351.59487.

5. Synthesis of Methyl α-D-Mannoseptanoside 31

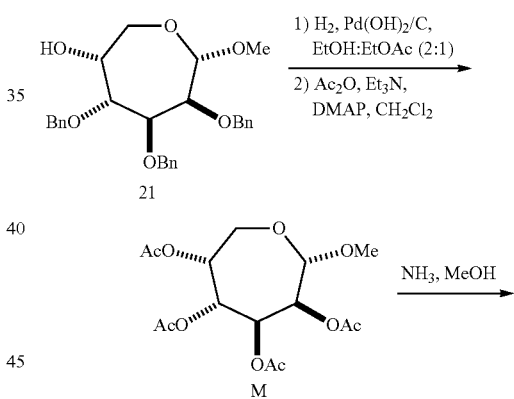

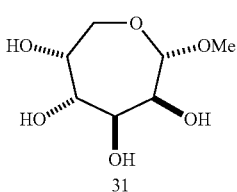

31

Methyl glycoside 21 (220 mg, 0.47 mmol) was dissolved in EtOH:EtOAc (2:1, 0.08 M, 4.0 mL). The solution was then purged with argon for approximately 10 minutes. Then 10% $Pd(OH)_2/C$ (20 mg) was added to the solution, and the reaction was placed under an atmosphere of $H_2$ (1 atm). The reaction was stirred for 2.5 hours, and then diluted with EtOH (4 mL). The mixture was then filtered though celite, and the volatiles were evaporated under reduced pressure. The crude mixture was then dissolved in $CH_2Cl_2$ (0.10 M, 3 mL), and $Ac_2O$ (0.15 mL, 1.5 mmol) and $Et_3N$ (0.28 mL, 2.0 mmol) were sequentially added. DMAP (10 mg) was then added. The reaction was stirred for 3 hours. The reaction was diluted with $CH_2Cl_2$ (25 mL) and quenched by the addition of $H_2O$ (20 mL). The aqueous layer was extracted with $CH_2Cl_2$ (1×50 mL). The organic extracts were combined and dried with $MgSO_4$. After filtration and evaporation of the volatiles under reduced pressure, chromatography (2:1 hexanes:EtOAc) gave tetraacetate M as a colorless syrup (136 mg, 80%).

$[\alpha]_D^{23}$=+58.6 (c 2.00, $CHCl_3$); $^1$H NMR (400 MHz, $CDCl_3$) δ 4.81 (dd, J=1.6, 6.8 Hz, 1H), 5.38 (m, 2H), 5.22 (m, 1H), 4.63 (d, J=6.4 Hz, 1H), 4.05 (dd, J=8.8, 13.2 Hz, 1H), 3.61 (dd, J=4.0, 12.4 Hz, 1H), 3.39 (s, 3H), 2.12 (s, 6H), 2.07 (s, 3H), 2.05 (s, 3H); $^{13}$C NMR (100 MHz, $CDCl_3$) δ 169.9, 169.9, 169.8, 100.9, 72.3, 70.2, 69.8, 68.6, 60.4, 55.8, 21.1, 20.9, 20.9; IR (KBr) 2964, 1749, 1371, 1227, 1051, 756 cm$^{-1}$; HRMS (ESI) [M+H] Calcd. for $C_{15}H_{23}O_{10}$ 363.12857, found 363.12888.

Peracetate M (136 mg, 0.38 mmol) was dissolved in MeOH (0.10 M, 3.0 mL). $NH_3$ (g) was then bubbled through the solution for 10 minutes. The flask was capped, and the reaction was stirred for 16 hours. Then the volatiles were evaporated under reduced pressure. The resulting colorless oil was placed on a high vacuum overnight to yield methyl mannoseptanoside 31 as a colorless syrup (74 mg, Quant.).

$[\alpha]_D^{23}$=+121.1 (c 1.00, MeOH); $^1$H NMR (400 MHz, $CD_3OD$) δ 4.30 (d, J=6.8 Hz, 1H), 3.93 (dd, J=1.2, 6.8 Hz, 1H), 3.87-3.70 (m, 4H), 3.26 (s, 3H), 3.24 (m, 2H); $^{13}$C NMR (100 MHz, $CD_3OD$) δ 105.9, 76.2, 72.6, 72.5, 70.8, 63.5, 55.7; IR (KBr) 3381, 2914, 1051 cm$^{-1}$; HRMS (APCI) [M+NH$_4^+$] Calcd. for $C_7H_{18}O_6N_1$ 212.11286, found 212.11261.

6. Synthesis of Mannoseptanosyl Disaccharide 32

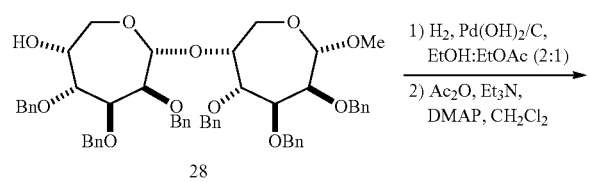

28

1) $H_2$, $Pd(OH)_2/C$, EtOH:EtOAc (2:1)
2) $Ac_2O$, $Et_3N$, DMAP, $CH_2Cl_2$

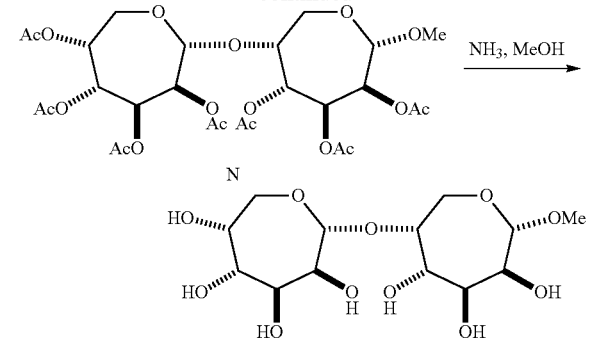

32

Disaccharide 28 (74 mg, 0.08 mmol) was dissolved in EtOH:EtOAc (2:1, 0.04 M, 2 mL). Argon was bubbled through the solution for 10 minutes. Then 10% $Pd(OH)_2/C$ (20 mg) was added to the solution, and the reaction was placed under an atmosphere of $H_2$ (1 atm).

The reaction was stirred for 2.5 hours, and then diluted with EtOH (3 mL). The mixture was then filtered though celite, and the volatiles were evaporated under reduced pressure. The crude mixture was then dissolved in $CH_2Cl_2$ (0.04 M, 2 mL), and $Ac_2O$ (0.07 mL, 0.8 mmol) and $Et_3N$ (0.12 mL, 0.90 mmol) were sequentially added. DMAP (10 mg) was then added. The reaction was stirred for 3 hours. The reaction was diluted with $CH_2Cl_2$ (50 mL) and quenched by the addition of $H_2O$ (50 mL). The aqueous layer was extracted with $CH_2Cl_2$ (1×50 mL). The organic extracts were combined and dried with $MgSO_4$. After filtration and evaporation of the volatiles under reduced pressure, chromatography (2:1→1:1 hexanes: EtOAc) gave peracetate N as a colorless oil (52 mg, Quant.).

$[\alpha]_D^{23}$=+83.3 (c 1.50, $CHCl_3$); $^1$H NMR (400 MHz, $CDCl_3$) δ 5.42 (m, 2H), 5.36 (m, 2H), 5.28 (m, 2H), 5.19 (m, 1H), 4.82 (d, J=6.8 Hz, 1H), 4.60 (d, J=6.4 Hz, 1H), 4.06 (m, 3H), 3.62 (dd, J=3.6, 12.4 Hz, 1H), 3.56 (m, 1H), 3.39 (s, 3H), 2.15 (s, 3H), 2.14 (s, 3H), 2.13 (s, 3H), 2.10 (s, 3H), 2.05 (s, 3H), 2.04 (s, 3H); $^{13}$C NMR (100 MHz, $CDCl_3$) δ 169.9, 169.9, 169.8, 169.7, 169.7, 100.7, 99.7, 73.6, 72.3, 71.3, 70.4, 70.2, 69.6, 68.0, 67.8, 61.4, 60.5, 55.6, 21.0, 21.0, 20.9, 20.9, 20.8; IR (KBr) 2937, 1753, 1371, 1223, 1049 cm$^{-1}$; HRMS (ESI) [M+NH$_4^+$] Calcd. for $C_{27}H_{42}O_{18}N_1$ 668.23964, found 668.23987.

Peracetate N (52 mg, 0.08 mmol) was dissolved in MeOH (0.02 M, 4.0 mL). $NH_3$ (g) was then bubbled through the solution for 10 minutes. The flask was capped, and the reaction was stirred for 16 hours. Then the volatiles were evaporated under reduced pressure. The resulting colorless oil was placed on a high vacuum overnight. Disaccharide 32 was obtained as a colorless syrup (26 mg, Quant.).

$[\alpha]_D^{23}$=+166.4 (c 0.75, MeOH); $^1$H NMR (400 MHz, $CD_3OD$) δ 4.57 (d, J=6.4 Hz, 1H), 4.32 (d, J=6.8 Hz, 1H), 3.98 (dd, J=1.2, 6.8 Hz, 1H), 3.92 (m, 2H), 3.87 (m, 3H), 3.80 (m, 4H), 3.31 (m, 1H), 3.26 (s, 3H), 3.19 (m, 2H); $^{13}$C NMR (100 MHz, $CD_3OD$) δ 105.6, 103.9, 76.7, 76.2, 75.9, 72.7, 72.5, 72.1, 70.9, 70.6, 63.6, 62.6, 55.8; IR (KBr) 3399, 2926, 1660, 1402, 1248, 1045 cm$^{-1}$; HRMS (ESI) [M+Na$^+$] Calcd. for $C_{13}H_{24}O_{11}Na_1$ 379.12108, found 379.12106.

7. Synthesis of Mannoseptanosyl Trisaccharide 33

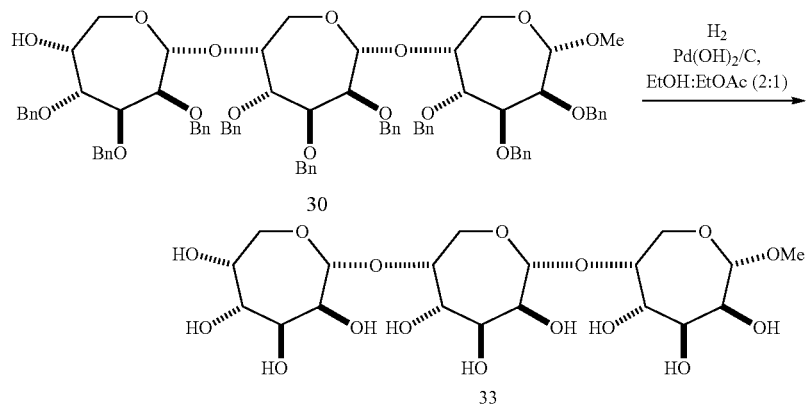

Trisaccharide 30 (40 mg, 0.03 mmol) was dissolved in EtOH EtOAc (2:1, 0.01 M, 3 mL). Argon was bubbled through the solution for 10 minutes. Then 10% Pd(OH)$_2$/C (20 mg) was added to the solution, and the reaction was placed under an atmosphere of H$_2$ (1 atm). The reaction was stirred for 2.5 hours, and then diluted with EtOH (3 mL). The mixture was then filtered though celite, and the volatiles were evaporated under reduced pressure to give trisaccharide 33 as a colorless syrup (15 mg, Quant.).

$[\alpha]_D^{23}$=+112.0 (c 1.00, MeOH); $^1$H NMR (400 MHz, CD$_3$OD) δ 4.67 (t, J=6.8 Hz, 2H), 4.42 (d, J=6.4 Hz, 1H), 4.09-3.84 (m, 18H), 3.42 (m, 1H), 3.36 (s, 3H); $^{13}$C NMR (100 MHz, CD$_3$OD) δ 105.6, 103.9, 103.6, 76.8, 76.7, 76.2, 75.9, 75.7, 72.6, 72.5, 72.1, 70.9, 70.6, 63.6, 62.8, 62.6, 55.8; IR (KBr) 3390, 2929, 1641, 1444, 1248, 1043 cm$^{-1}$; HRMS (ESI) [M+Na$^+$] Calcd. for C$_{19}$H$_{34}$O$_{16}$Na$_1$ 541.17391, found 541.17548.

Enzyme Inhibition Studies

PNP-Mannose Assay:

The catalytic activity of Jack Bean α-mannosidase was assayed by a discontinuous colorimetric assay, using p-nitrophenyl-α-D-mannopyranoside (PNP-Man). In a typical 100-μL reaction mixture, 0.5 to 30 mM PNP-Man in 10 mM sodium citrate buffer (pH 4.5) was preincubated at 25° C. for 10 minutes. The hydrolysis assay was initiated by addition of 2 μL of α-mannosidase (250 ng/μL). Over the 20-minute assay period, multiple aliquots (20 μL) were removed from the reaction mixture and immediately quenched in 980-μL of 1 M sodium carbonate buffer (pH 12). The product of the hydrolysis, p-nitrophenolate (PNP), was detected spectrophotometrically at 400 nm (ε=1.77×10$^4$ M$^{-1}$cm$^{-1}$) in a microtiterplate reader. All experiments were performed in triplicates and corrected for background. Observed turnover rates (k$_{cat}$) and apparent binding constants (K$_M$) were determined by fitting the data to the Michaelis-Menten equation, using non-linear regression analysis in the Origin? software. For the α-mannosidase inhibition studies with compounds 31, 32, and 33, the above reaction mixture was supplemented with the analogs at 0.75 mM and 6 mM, respectively. All experiments were done in triplicates and the resulting steady-state kinetics data were fitted to the modified Michaelis-Menten equation for competitive inhibition.

We claim:

1. A compound of formula (I):

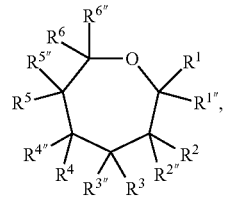

wherein R$^1$ and R$^{1'''}$ are each independently selected from the group consisting of: H, OH, alkoxy, C$_{1-10}$alkylcarbonyl, phosphoryl, phosphonate, phosphinate, phosphonoamidate, halo, CN, NO$_2$, N$_3$, NH$_2$, acylamino, amido, amidino, C$_{1-6}$alkyl, C$_{2-6}$alkenyl, C$_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, C$_{1-6}$alkyl-O—C$_{1-6}$alkyl, C$_{1-6}$alkyl-O-alkenyl, C$_{1-6}$alkyl-O-alkynyl, C$_{1-6}$alkyl-S—C$_{1-6}$alkyl, C$_{1-6}$alkyl-S-alkenyl, C$_{1-6}$alkyl-S-alkynyl, CONH$_2$, COOR, CH$_2$CN, CH$_2$N$_3$, and

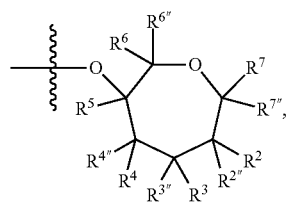

with the proviso that one of R$^1$ and R$^{1'''}$, but not both, is

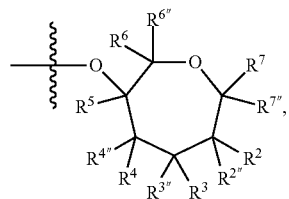

wherein R is selected from the group consisting of: H; $C_{1-6}$alkyl, $C_{2-6}$alkenyl, or $C_{2-6}$alkynyl, each of which is optionally substituted; CN, $N_3$, halo, OH, $CONH_2$, $NH_2$, and amidino;

wherein $R^7$ and $R^{7''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, $CH_2N_3$, and

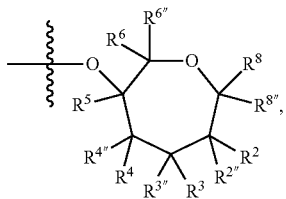

with the proviso that one of $R^7$ and $R^{7''}$, but not both, is alkoxy or

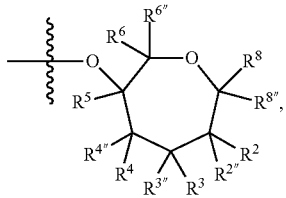

wherein $R^8$ and $R^{8''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$;

$R^2$-$R^5$ and $R^{2''}$-$R^{5''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$; and $R^6$ and $R^{6''}$ are independently selected from the group consisting of H and alkyl.

2. The compound according to claim 1, wherein $R^6$ and $R^{6''}$ are each H.

3. The compound according to claim 2, wherein $R^2$-$R^5$ and $R^{2''}$-$R^{5''}$ are each independently selected from the group consisting of: H, OH, $C_{1-6}$alkyl, or alkoxy.

4. The compound according to claim 3, wherein $R^2$-$R^5$ are OH; $R^{2''}$-$R^{5''}$ are H; $R^1$ is alkoxy; and $R^{1''}$ is H.

5. The compound according to claim 1, wherein $R^2$-$R^4$ are OH; $R^5$ is H; $R^6$ is H; $R^{2''}$-$R^{7''}$ are H; $R^{5''}$ is OH; and $R^7$ is alkoxy.

6. The compound according to claim 1, wherein $R^1$ is

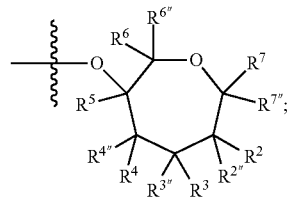

$R^{1''}$ is H; and $R^7$ is methoxy.

7. The compound according to claim 1, wherein $R^1$ is

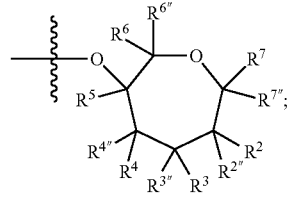

$R^{1''}$ is H; $R^2$-$R^4$ are OH; $R^5$ is H; $R^6$ is H; $R^{2''}$-$R^{7''}$ are H; $R^{5''}$ is OH; and $R^7$ is

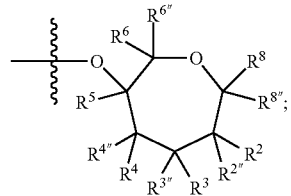

$R^8$ is alkoxy; and $R^{8''}$ is H.

8. The compound according to claim 7, wherein $R^8$ is methoxy.

9. A compound of formula (II):

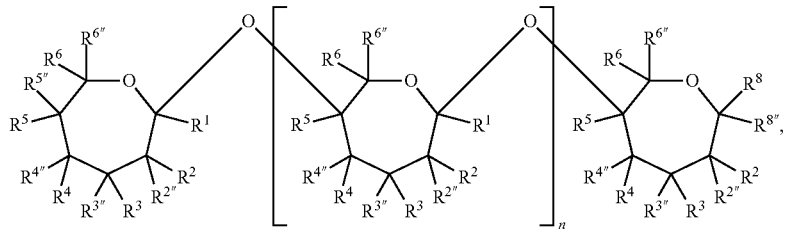

wherein:
- $R^1$ is independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$,
- R is selected from the group consisting of: H; $C_{1-6}$alkyl, $C_{2-6}$alkenyl, or $C_{2-6}$alkynyl, each of which is optionally substituted; CN, $N_3$, halo, OH, $CONH_2$, $NH_2$, and amidino;
- $R^8$ and $R^{8''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$;
- $R^2$-$R^5$ and $R^{2''}$-$R^{5''}$ are each independently selected from the group consisting of: H, OH, alkoxy, $C_{1-10}$alkylcarbonyl, phosphoryl, phosphonate, phosphinate, phosphonoamidate, halo, CN, $NO_2$, $N_3$, $NH_2$, acylamino, amido, amidino, $C_{1-6}$alkyl, $C_{2-6}$alkenyl, $C_{2-6}$alkynyl, carbonyl, thiocarbonyl, acyl, haloalkyl, haloalkenyl, haloalkynyl, cycloalkyl, sulfonyl, sulfoxido, sulfate, sulfonate, sulfamoyl, sulfonamide, $C_{1-6}$alkyl-O—$C_{1-6}$alkyl, $C_{1-6}$alkyl-O-alkenyl, $C_{1-6}$alkyl-O-alkynyl, $C_{1-6}$alkyl-S—$C_{1-6}$alkyl, $C_{1-6}$alkyl-S-alkenyl, $C_{1-6}$alkyl-S-alkynyl, $CONH_2$, COOR, $CH_2CN$, and $CH_2N_3$;
- $R^6$ and $R^{6''}$ are independently selected from the group consisting of H and alkyl; and
- n is 0 to 10,000.

* * * * *

UNITED STATES PATENT AND TRADEMARK OFFICE
CERTIFICATE OF CORRECTION

PATENT NO.         : 8,703,977 B2
APPLICATION NO.    : 13/141336
DATED              : April 22, 2014
INVENTOR(S)        : Matthew A. Boone and Frank E. MacDonald It is certified that error appears in the above-identified patent and that said Letters Patent is hereby corrected as shown below:

Specification, column 1, lines 3-4, immediately below the Title, please insert the following:

--ACKNOWLEDGEMENT

This invention was made with government support under Grant No. RO1 CA059703 awarded by the National Institutes of Health. The government has certain rights in the invention--

Signed and Sealed this
Twenty-fourth Day of November, 2015

Michelle K. Lee
*Director of the United States Patent and Trademark Office*